(12) United States Patent
Faller et al.

(10) Patent No.: US 10,004,528 B2
(45) Date of Patent: Jun. 26, 2018

(54) SLEEVE FEATURES FOR ULTRASONIC BLADE OF A SURGICAL INSTRUMENT

(71) Applicant: Ethicon Endo-Surgery, Inc., Cincinnati, OH (US)

(72) Inventors: Craig N. Faller, Batavia, OH (US); Cory G. Kimball, Hamilton, OH (US); David J. Cagle, Cincinnati, OH (US); Benjamin D. Dickerson, II, Cincinnati, OH (US); Kristen Denzinger, Cincinnati, OH (US); Jeffrey D. Messerly, Cincinnati, OH (US); Phillip H. Clauda, Cincinnati, OH (US); Ryan M. Asher, Cincinnati, OH (US); Frederick L. Estera, Cincinnati, OH (US); Omar J. Vakharia, Cincinnati, OH (US); William B. Weisenburgh, II, Maineville, OH (US); Richard W. Timm, Cincinnati, OH (US); Richard C. Smith, Milford, OH (US); Paul F. Riestenberg, North Bend, OH (US); Wells D. Haberstich, Loveland, OH (US); Gregory W. Johnson, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 319 days.

(21) Appl. No.: 14/552,681

(22) Filed: Nov. 25, 2014

(65) Prior Publication Data

US 2015/0148835 A1    May 28, 2015

Related U.S. Application Data

(60) Provisional application No. 61/908,920, filed on Nov. 26, 2013.

(51) Int. Cl.
*A61B 17/32* (2006.01)
*A61N 7/00* (2006.01)
(Continued)

(52) U.S. Cl.
CPC ........ *A61B 17/320092* (2013.01); *A61B 17/320068* (2013.01); *A61N 7/00* (2013.01);
(Continued)

(58) Field of Classification Search
CPC ......... A61B 2017/2829; A61B 2017/320084; A61B 2017/2825; A61B 2017/00353;
(Continued)

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

| CN | 101883529 A | 11/2010 |
| JP | 2014-000311 | 1/2014 |

(Continued)

OTHER PUBLICATIONS

U.S. Appl. No. 61/410,603, filed Nov. 5, 2010.
(Continued)

*Primary Examiner* — Anh Dang
(74) *Attorney, Agent, or Firm* — Frost Brown Todd LLC

(57) ABSTRACT

An apparatus comprises a body, a shaft assembly, and an end effector. The shaft assembly extends distally from the body. The end effector is located at a distal end of the shaft assembly. The end effector comprises an ultrasonic blade, a clamp arm, and a sleeve. The ultrasonic blade is configured to vibrate at an ultrasonic frequency. The clamp arm is configured to move toward the ultrasonic blade. The sleeve extends along at least part of the length of an outer portion of the ultrasonic blade or the clamp arm. The sleeve is configured to prevent tissue from contacting a portion of the ultrasonic blade or clamp arm covered by the sleeve.

13 Claims, 57 Drawing Sheets

(51) Int. Cl.
*A61B 18/00* (2006.01)
*A61B 18/14* (2006.01)
*A61B 17/00* (2006.01)
*A61B 17/28* (2006.01)
*A61B 90/00* (2016.01)

(52) U.S. Cl.
CPC . *A61B 18/1442* (2013.01); *A61B 2017/00353* (2013.01); *A61B 2017/2825* (2013.01); *A61B 2017/320076* (2013.01); *A61B 2017/320084* (2013.01); *A61B 2018/00011* (2013.01); *A61B 2018/0063* (2013.01); *A61B 2018/00107* (2013.01); *A61B 2090/0436* (2016.02); *A61B 2090/0472* (2016.02)

(58) Field of Classification Search
CPC .... A61B 2090/0472; A61B 2090/0436; A61B 2018/00011; A61B 17/320092; A61B 17/320068; A61B 18/1442
See application file for complete search history.

(56) References Cited

U.S. PATENT DOCUMENTS

| | | | |
|---|---|---|---|
| 5,980,510 | A | 11/1999 | Tsonton et al. |
| 6,056,735 | A | 5/2000 | Okada et al. |
| 6,193,709 | B1 | 2/2001 | Miyawaki et al. |
| 6,325,811 | B1 | 12/2001 | Messerly |
| 6,358,267 | B1 | 3/2002 | Murakami et al. |
| 6,500,176 | B1 | 12/2002 | Truckai et al. |
| 6,669,690 | B1 | 12/2003 | Okada et al. |
| 6,773,444 | B2 | 8/2004 | Messerly |
| 6,783,524 | B2 | 8/2004 | Anderson et al. |
| 6,958,070 | B2 | 10/2005 | Witt et al. |
| 7,066,936 | B2 | 6/2006 | Ryan |
| 7,074,219 | B2 | 7/2006 | Levine et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,223,267 | B2 | 5/2007 | Isola et al. |
| 7,235,073 | B2 | 6/2007 | Levine et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 7,563,269 | B2 | 7/2009 | Hashiguchi |
| 7,901,423 | B2 | 3/2011 | Stulen et al. |
| 8,328,834 | B2 | 12/2012 | Isaacs et al. |
| 8,348,880 | B2 | 1/2013 | Messerly et al. |
| 8,444,663 | B2 | 5/2013 | Houser et al. |
| 8,444,664 | B2 | 5/2013 | Balanev et al. |
| 8,461,744 | B2 | 6/2013 | Wiener et al. |
| 8,523,889 | B2 | 9/2013 | Stulen et al. |
| 8,535,257 | B1 | 9/2013 | Zelten et al. |
| 8,591,459 | B2 | 11/2013 | Clymer et al. |
| 8,591,536 | B2 | 11/2013 | Robertson |
| 8,623,027 | B2 | 1/2014 | Price et al. |
| 8,652,132 | B2 | 2/2014 | Tsuchiya et al. |
| 8,662,745 | B2 | 3/2014 | Misuchenko et al. |
| 8,685,020 | B2 | 4/2014 | Weizman et al. |
| 8,974,447 | B2 | 3/2015 | Kimball et al. |
| 8,986,302 | B2 | 3/2015 | Aldridge et al. |
| 9,005,199 | B2 | 4/2015 | Beckman et al. |
| 9,023,071 | B2 | 5/2015 | Miller et al. |
| 2005/0192611 | A1 | 9/2005 | Houser |
| 2005/0273126 | A1 | 12/2005 | Beaupre |
| 2006/0079874 | A1 | 4/2006 | Faller et al. |
| 2006/0265035 | A1 | 11/2006 | Yachi et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0030440 | A1* | 1/2009 | Mastri ............ A61B 17/29 606/169 |
| 2009/0036914 | A1 | 2/2009 | Houser |
| 2009/0143795 | A1* | 6/2009 | Robertson ...... A61B 17/320092 606/169 |
| 2010/0331873 | A1 | 12/2010 | Dannaher et al. |
| 2012/0112687 | A1 | 5/2012 | Houser et al. |
| 2012/0116265 | A1 | 5/2012 | Houser et al. |
| 2012/0116433 | A1* | 5/2012 | Houser .......... A61B 17/320092 606/169 |
| 2012/0296356 | A1* | 11/2012 | Balanev ........ A61B 17/320092 606/169 |
| 2013/0090576 | A1 | 4/2013 | Stulen et al. |
| 2013/0103065 | A1* | 4/2013 | Timm ............ A61B 17/320092 606/169 |
| 2013/0303949 | A1 | 11/2013 | Kawaguchi et al. |
| 2014/0005668 | A1 | 1/2014 | Rhee et al. |
| 2014/0005701 | A1 | 1/2014 | Olson et al. |
| 2014/0012297 | A1 | 1/2014 | Ross et al. |
| 2014/0012298 | A1 | 1/2014 | Cunningham et al. |
| 2014/0012299 | A1 | 1/2014 | Stoddard et al. |
| 2014/0114334 | A1 | 4/2014 | Olson et al. |
| 2014/0135804 | A1 | 5/2014 | Weisenburgh et al. |
| 2014/0163549 | A1 | 6/2014 | Yates et al. |
| 2014/0180002 | A1 | 6/2014 | Voic |
| 2015/0080924 | A1 | 3/2015 | Stulen et al. |
| 2015/0080925 | A1 | 3/2015 | Schulte et al. |
| 2015/0122530 | A1 | 5/2015 | Katsuda |
| 2015/0148832 | A1 | 5/2015 | Boudreaux et al. |
| 2015/0148833 | A1 | 5/2015 | Stokes et al. |
| 2015/0148834 | A1 | 5/2015 | Gee et al. |
| 2015/0148835 | A1 | 5/2015 | Faller et al. |

FOREIGN PATENT DOCUMENTS

| | | |
|---|---|---|
| WO | WO 2012/116957 | 9/2012 |
| WO | WO 2013/183715 | 12/2013 |
| WO | WO 2013/062103 | 4/2015 |
| WO | WO 2015/081038 A1 | 6/2015 |
| WO | WO 2015/081039 A1 | 6/2015 |
| WO | WO 2015/081040 A1 | 6/2015 |
| WO | WO 2015/081042 A1 | 6/2015 |
| WO | WO 2013/157571 A1 | 12/2015 |

OTHER PUBLICATIONS

U.S. Appl. No. 14/553,142, filed Nov. 25, 2014.
U.S. Appl. No. 14/553,329, filed Nov. 25, 2014.
U.S. Appl. No. 14/553,378, filed Nov. 25, 2014.
International Search Report and Written Opinion dated Jan. 30, 2015 for Application No. PCT/US2014/067221, 10 pgs.
International Search Report and Written Opinion dated Feb. 12, 2015 for Application No. PCT/US2014/067218, 9 pgs.
International Search Report and Written Opinion dated Feb. 12, 2015 for Application No. PCT/US2014/067219, 9 pgs.
International Search Report and Written Opinion dated Feb. 12, 2015 for Application No. PCT/US2014/067225, 9 pgs.
U.S. Appl. No. 14/552,530.
U.S. Appl. No. 14/552,552.
U.S. Appl. No. 14/552,614.
U.S. Appl. No. 14/553,142.
U.S. Appl. No. 14/553,329.
U.S. Appl. No. 14/553,378.
Search report dated Jan. 15, 2018 for Chinese Patent Application No. 201480073943.5.
Office Action dated Jan. 23, 2018 for Chinese Patent Application No. 201480073943.5.

* cited by examiner

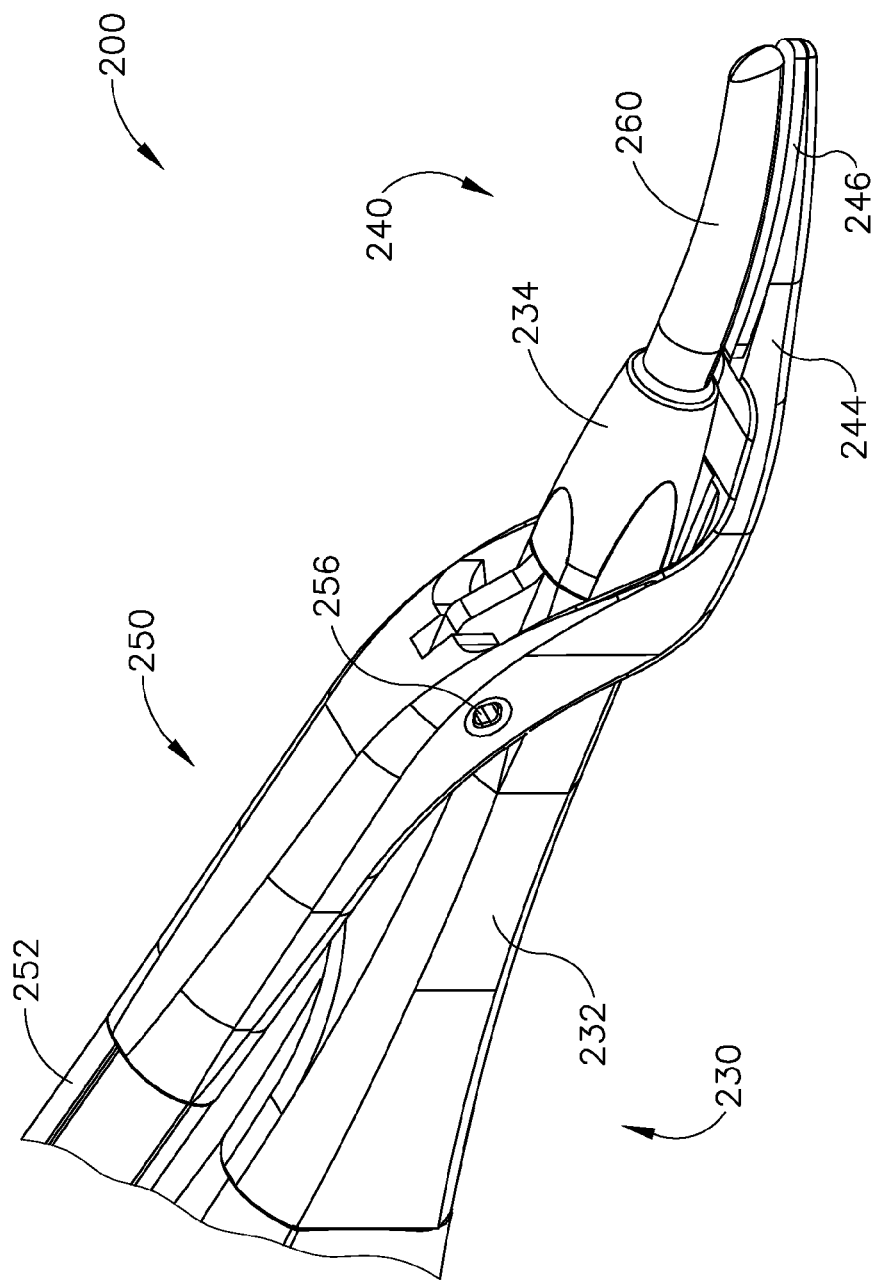

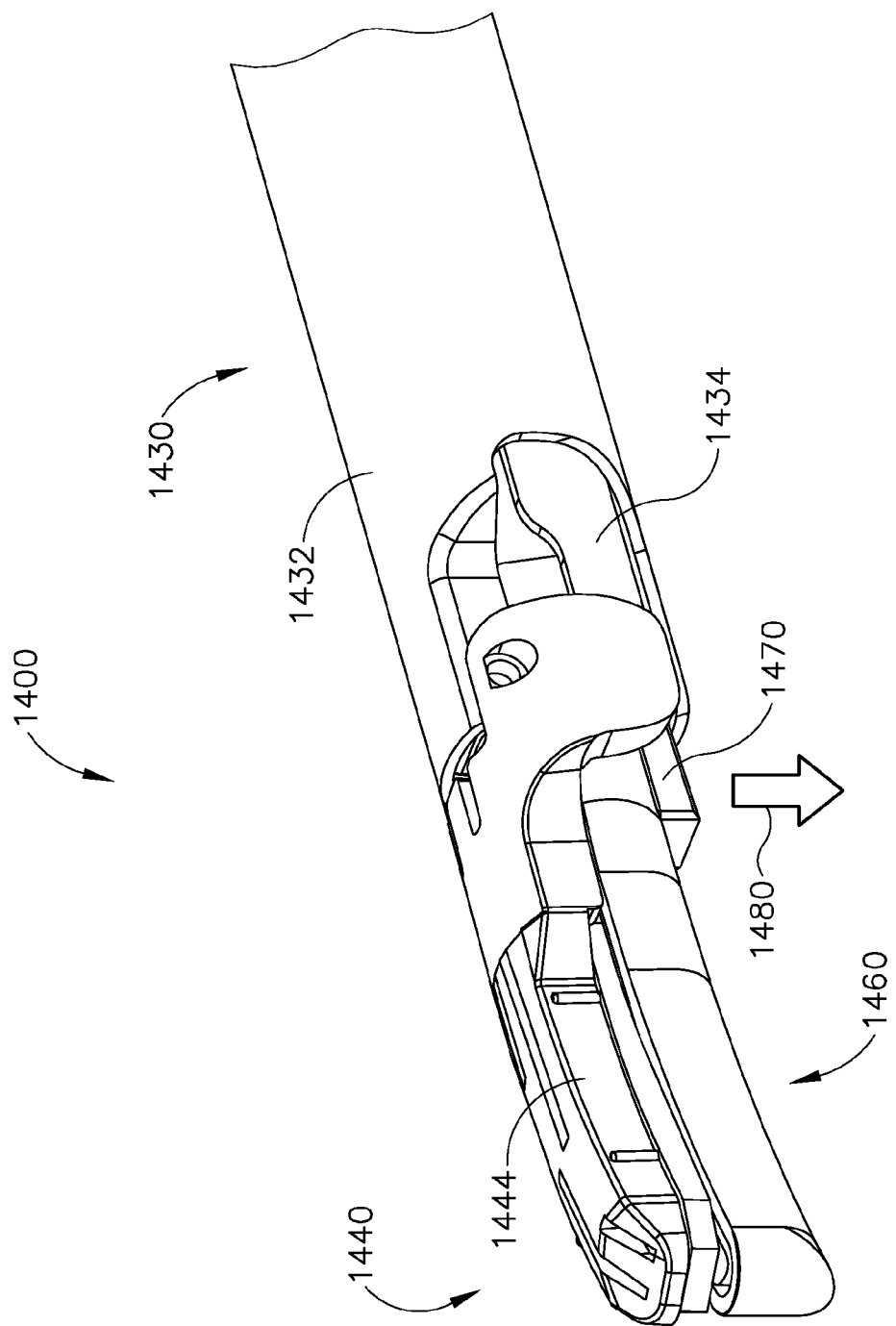

SLEEVE FEATURES FOR ULTRASONIC BLADE OF A SURGICAL INSTRUMENT

PRIORITY

This application claims priority to U.S. Provisional Patent App. No. 61/908,920, entitled "Heat Management for Ultrasonic Surgical Instrument," filed Nov. 26, 2013, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, now U.S. Pat. No. 9,393,037, issued Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7A depicts a detailed perspective view of an end effector of an exemplary alternative instrument that includes a removable blade sleeve;

FIG. 28B depicts a detailed perspective view of the end effector of FIG. 28A, with the blade sleeve deflected downwardly;

Figure 1:
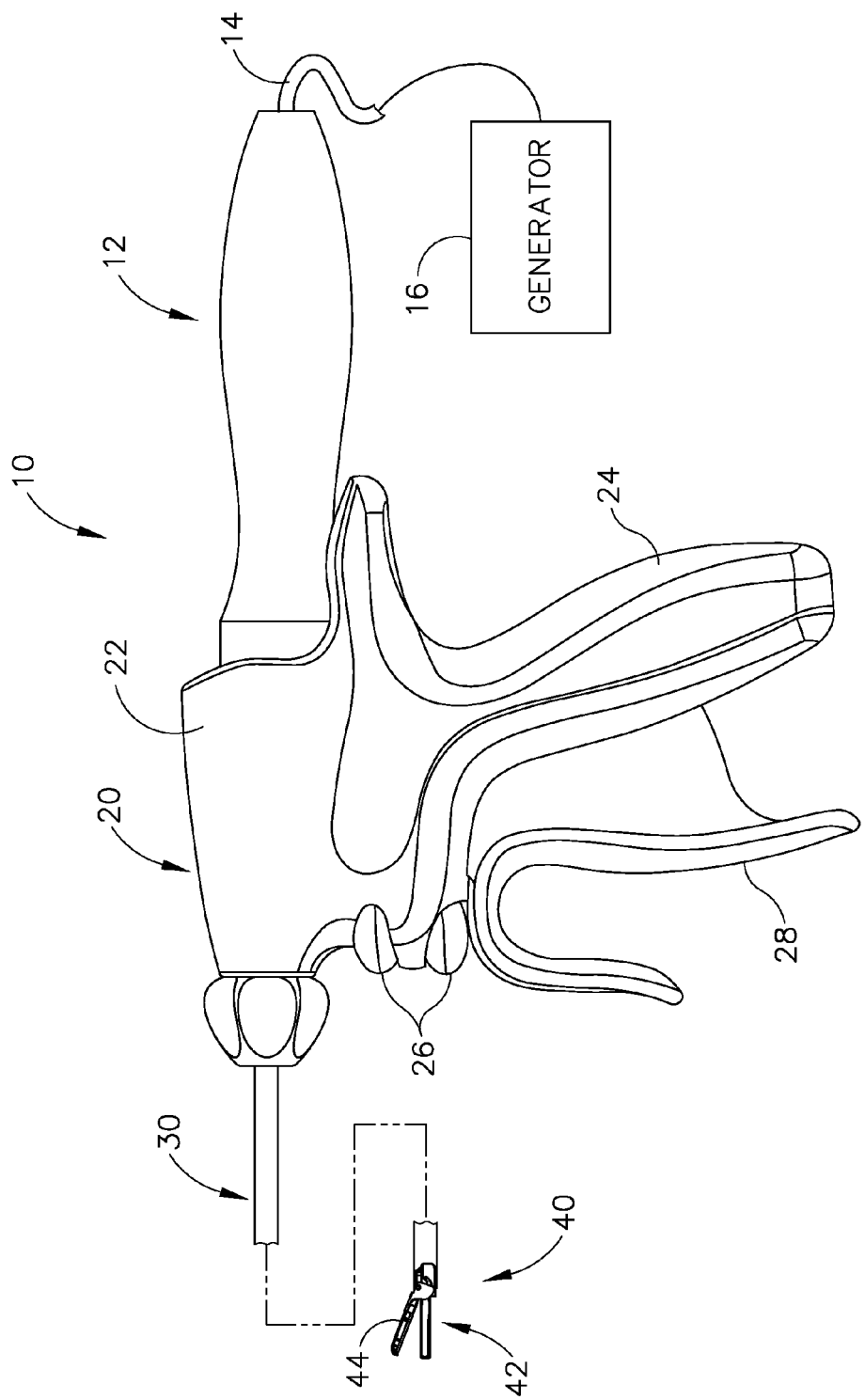
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6B illustrate exemplary ultrasonic surgical instruments (10, 100). At least part of each instrument (10, 100) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, now U.S. Pat. No. 8,623,027; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; U.S. Pub. No. 2014/0114334, now U.S. Pat. No. 9,095,367; U.S. Pat. App. No. 61/410,603; and/or U.S. patent application Ser. No. 14/028,717, published as U.S. Pub. No. 2015/0080924 on Mar. 19, 2015. The disclosures of each of the foregoing patents, publications, and applications are incorporated by reference herein. As described therein and as will be described in greater detail below, each instrument (10, 100) is operable to cut tissue and seal or weld tissue (e.g., a blood vessel, etc.) substantially simultaneously. It should also be understood that instruments (10, 100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (10, 100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (10, 100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
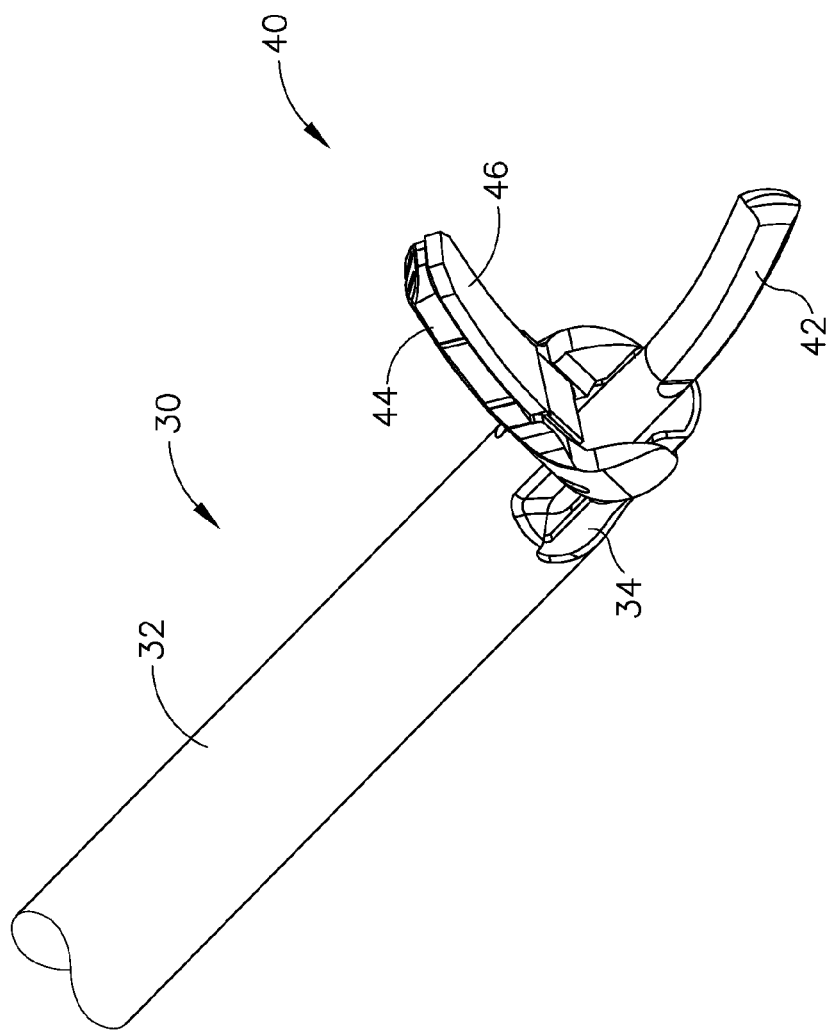
FIG. 2 depicts a perspective view of the end effector of the instrument of FIG. 1, in an open configuration.

A. Exemplary Ultrasonic Surgical Instrument for Minimally Invasive Surgical Procedures FIG. 1 illustrates an exemplary ultrasonic surgical instrument (10) that is configured to be used in minimally invasive surgical procedures (e.g., via a trocar or other small diameter access port, etc.). Instrument (10) of this example comprises a handle assembly (20), a shaft assembly (30), and an end effector (40). As shown in FIGS. 2-3B, shaft assembly (30) comprises an outer sheath (32), an inner tube (34) slidably disposed within outer sheath (32), and a waveguide (38) disposed within inner tube (34). As will be discussed in more detail below, longitudinal translation of inner tube (34) relative to outer sheath (32) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. In the present example, a resilient member biases trigger (28) away from pistol grip (24). Trigger (28) is pivotable toward pistol grip (24) to drive inner tube (34) proximally relative to outer sheath (32). When trigger (28) is thereafter released or driven away from pistol grip (24), inner tube (34) is driven distally relative to outer sheath (32). By way of example only, trigger (28) may be coupled with inner tube (34) in accordance with the teachings of various references cited herein. Other suitable ways in which trigger (28) may be coupled with inner tube (34) will be apparent to those of ordinary skill in the art in view of the teachings herein.

Figure 3A:
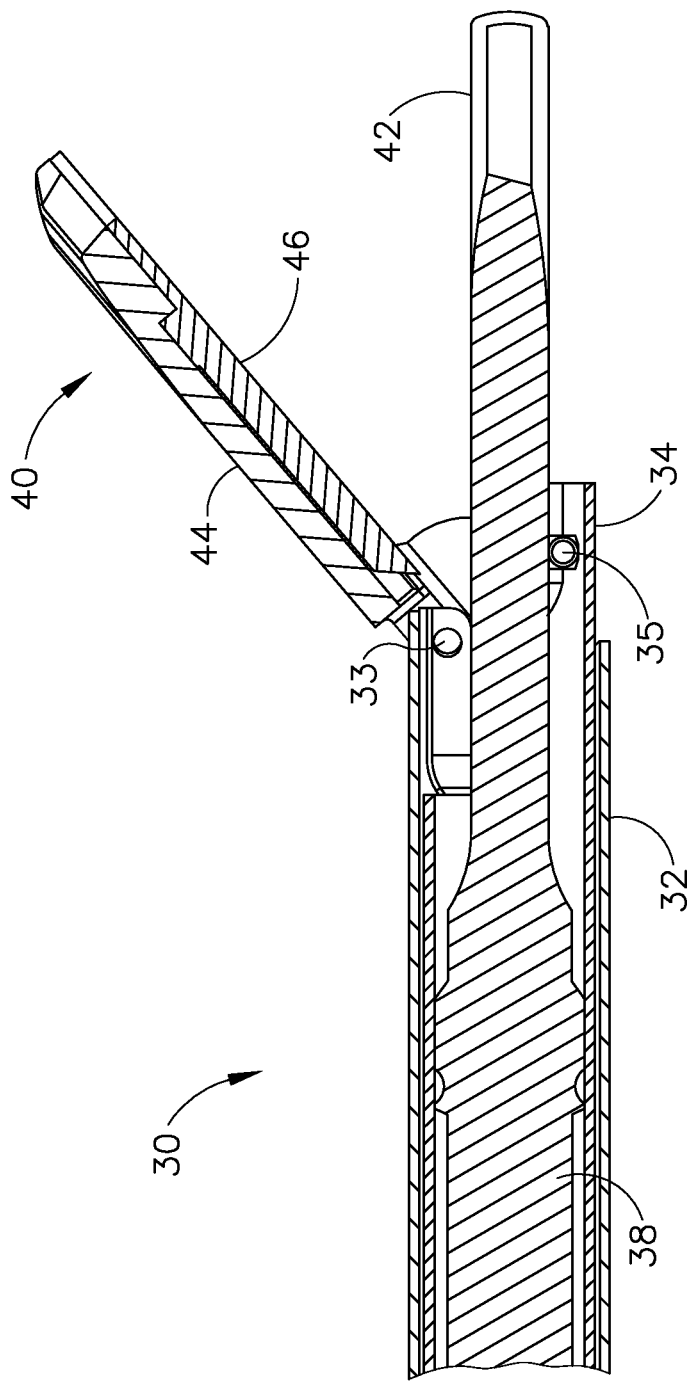
FIG. 3A depicts a side cross-sectional view of the end effector of FIG. 2, in the open configuration.
Figure 3B:
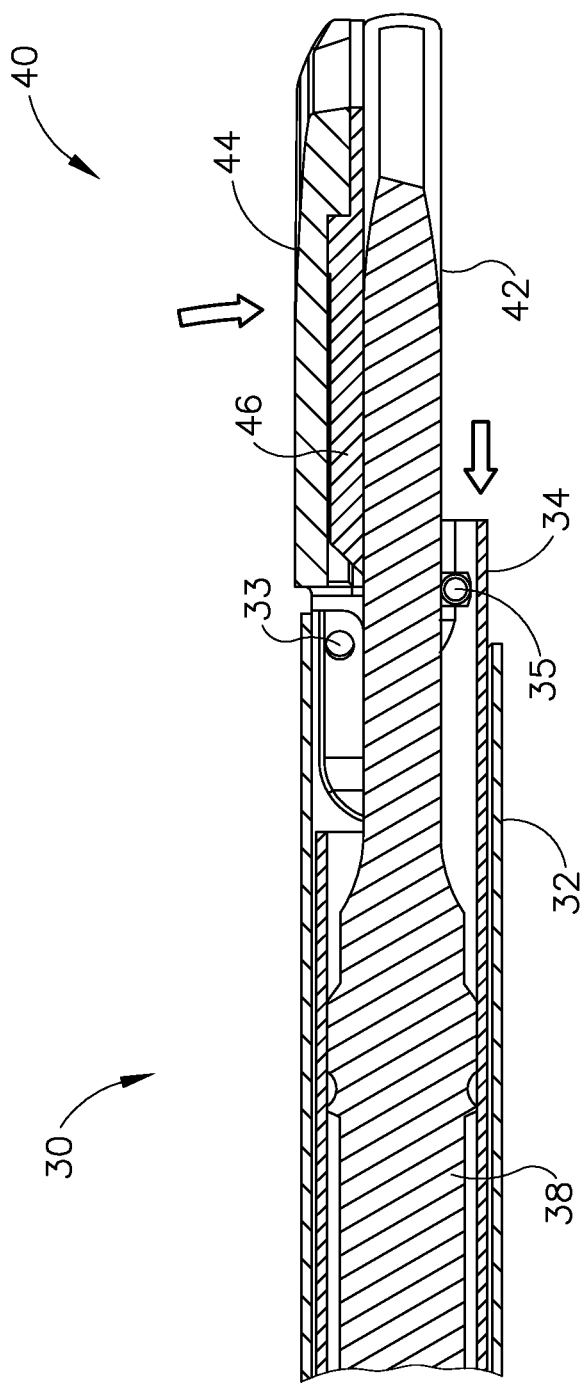
FIG. 3B depicts a side cross-sectional view of the end effector of FIG. 2, in a closed configuration.

As shown in FIGS. 2-3B, end effector (40) includes an ultrasonic blade (42) and a pivoting clamp arm (44). Clamp arm (44) includes a clamp pad (46) facing ultrasonic blade (42). Clamp arm (44) is pivotably coupled with a distal end of outer sheath (32) of shaft assembly (30), above ultrasonic blade (42), via a pin (33). A distal end of inner tube (34) is pivotably coupled with a proximal end of clamp arm (44), below ultrasonic blade (42), via another pin (35). Thus, longitudinal translation of inner tube (34) relative to outer sheath (32) causes clamp arm (44) to pivot about pin (33) toward and away from ultrasonic blade (42) to thereby clamp tissue between clamp pad (46) and ultrasonic blade (42) to transect and/or seal the tissue. In particular, as seen in the transition from FIG. 3A to FIG. 3B, proximal longitudinal translation of inner tube (34) relative to outer sheath (32) and handle assembly (20) causes clamp arm (44) to pivot toward ultrasonic blade (42); and distal longitudinal translation of inner tube (34) relative to outer sheath (32) and handle assembly (20) causes clamp arm (44) to pivot away from ultrasonic blade (42). It should therefore be understood that pivoting of trigger (28) toward pistol grip (24) will cause clamp arm (44) to pivot toward ultrasonic blade (42); and that pivoting of trigger (28) away from pistol grip (24) will cause clamp arm (44) to pivot away from ultrasonic blade (42).

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (38), which extends through shaft assembly (30) to reach ultrasonic blade (42). Waveguide (38) is secured within shaft assembly (30) via a pin (not shown), which passes through waveguide (38) and shaft assembly (30). This pin is located at a position along the length of waveguide (38) corresponding to a node associated with resonant ultrasonic vibrations communicated through waveguide (38). As noted above, when ultrasonic blade (42) is in an activated state (i.e., vibrating ultrasonically), ultrasonic blade (42) is operable to effectively cut through and seal tissue, particularly when the tissue is being clamped between clamp pad (46) and ultrasonic blade (42). It should be understood that waveguide (38) may be configured to amplify mechanical vibrations transmitted through waveguide (38). Furthermore, waveguide (38) may include features operable to control the gain of the longitudinal vibrations along waveguide (38) and/or features to tune waveguide (38) to the resonant frequency of the system.

In the present example, the distal end of ultrasonic blade (42) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (42), thereby providing oscillation of ultrasonic blade (42) at the resonant ultrasonic frequency. Thus, when tissue is secured between ultrasonic blade (42) and clamp pad (46), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and/or clamp pad (46) to also seal the tissue.

An operator may activate buttons (26) to selectively activate transducer assembly (12) to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub.

No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; and/or U.S. Pub. No. 2014/0114334, now U.S. Pat. No. 9,095,367. Additional merely illustrative variations for instrument (10) will be described in greater detail below. It should be understood that the below described variations may be readily applied to instrument (10) described above and any of the instruments referred to in any of the references that are cited herein, among others.

B. Exemplary Ultrasonic Surgical Instrument for Open Surgical Procedures

Figure 4:
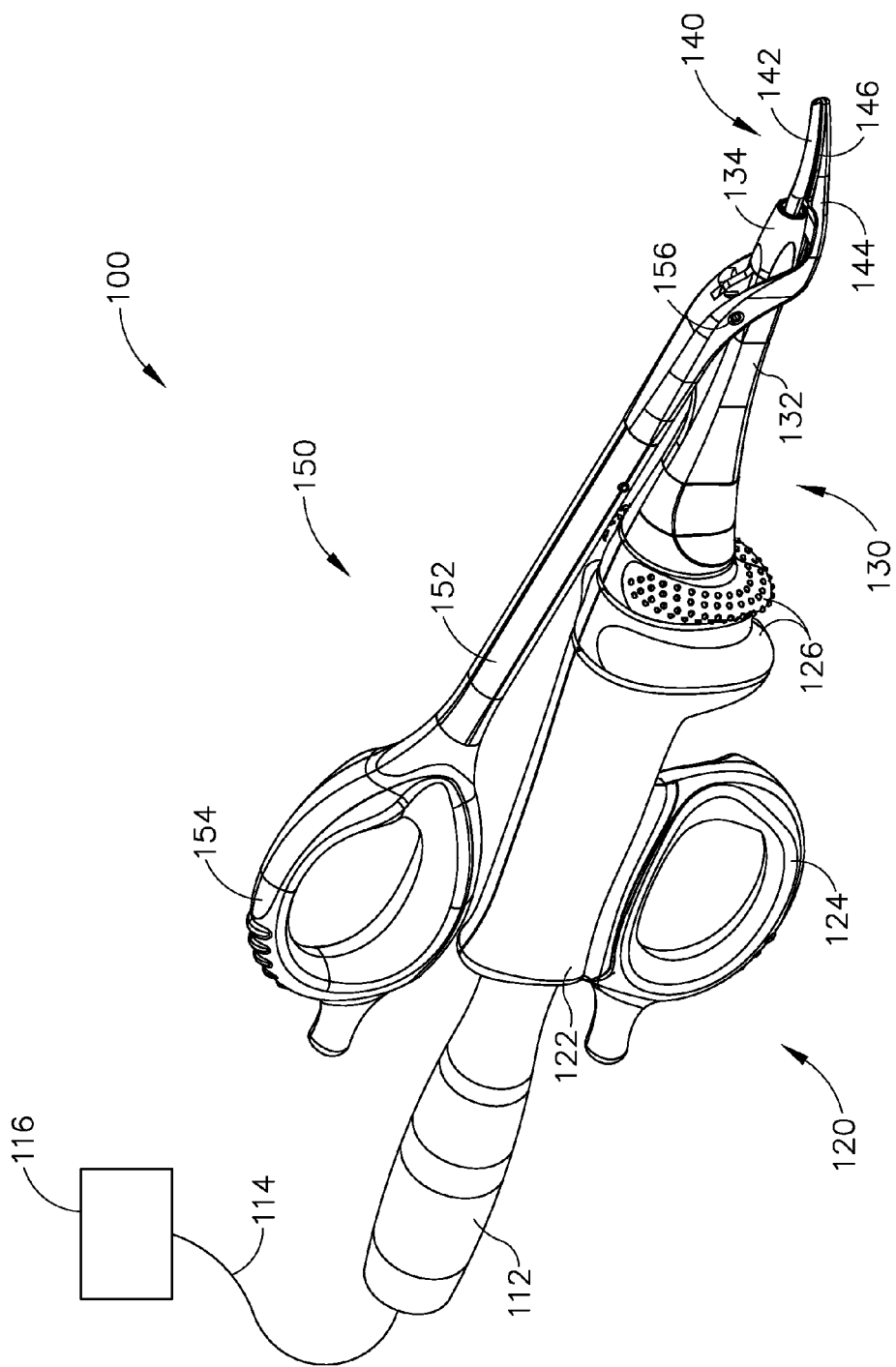
FIG. 4 depicts a perspective view of another exemplary surgical instrument.

FIG. 4 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm assembly (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 5:
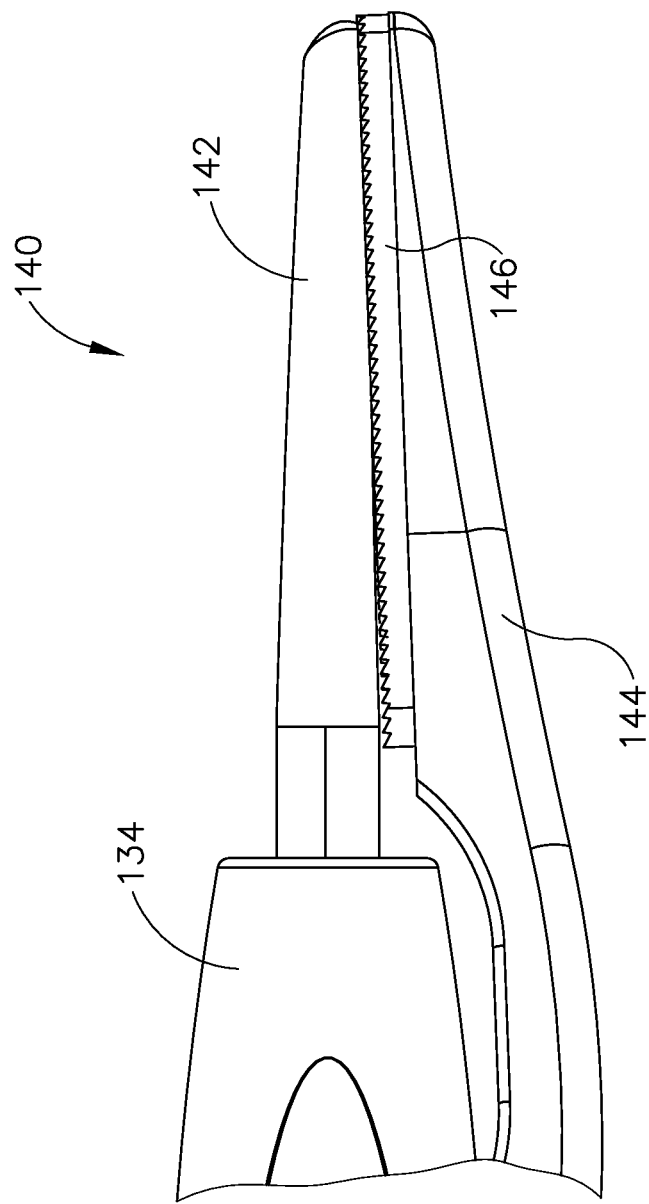
FIG. 5 depicts a side elevational view of the end effector of the instrument of FIG. 4, in a closed configuration.
Figure 6A:
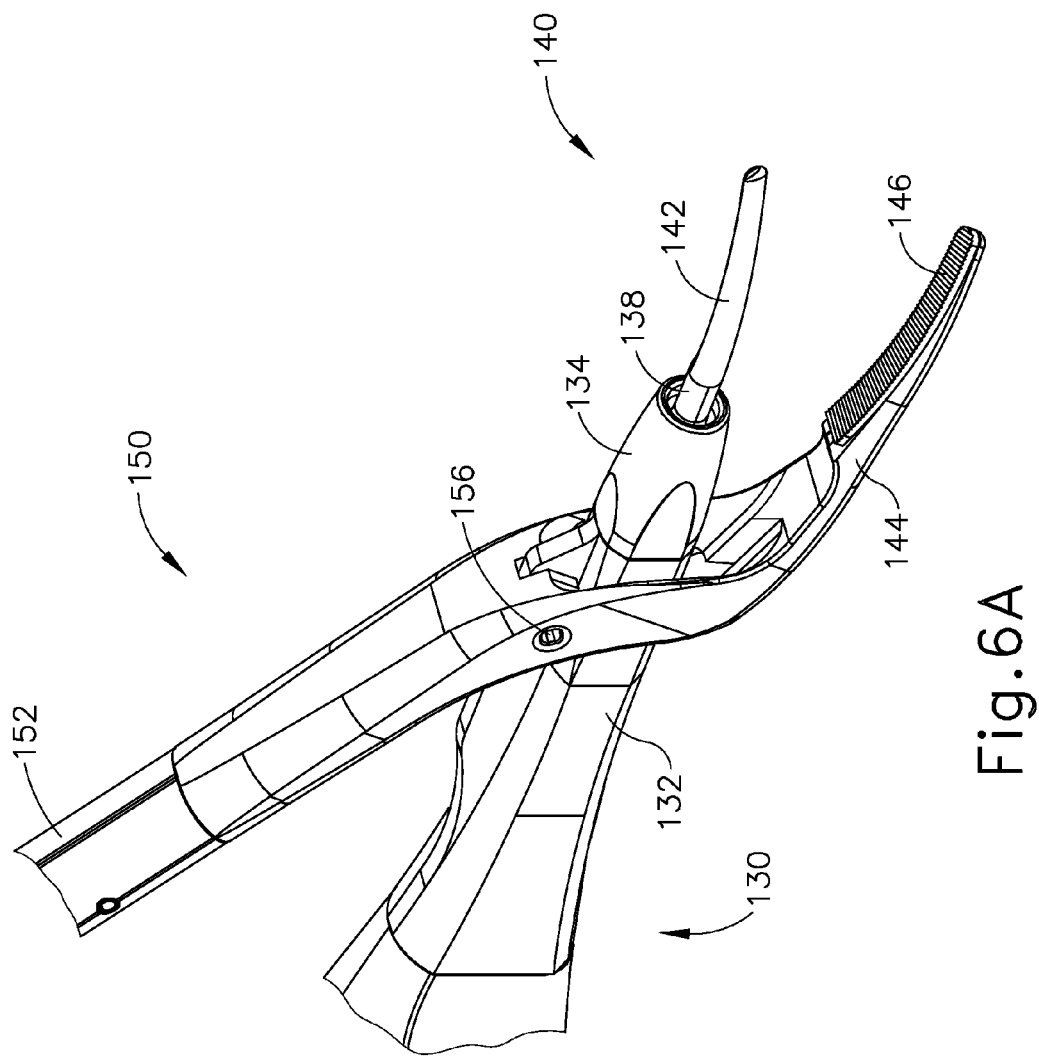
FIG. 6A depicts a perspective view of the end effector of FIG. 5, in an open configuration.
Figure 6B:
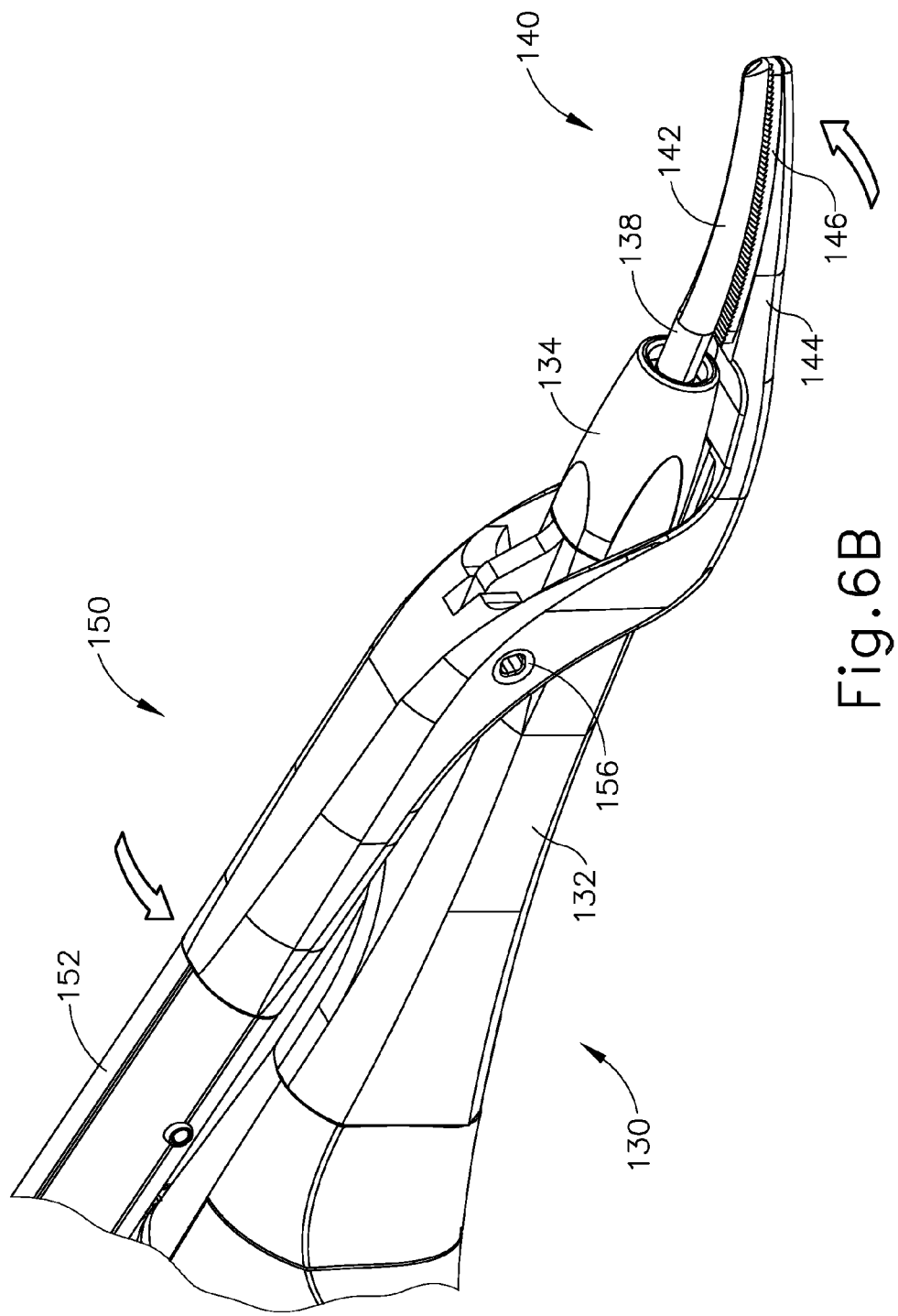
FIG. 6B depicts a perspective view of the end effector of FIG. 5, in a closed configuration.

Shaft assembly (130) comprises an outer sheath (132) extending distally from body (122). A cap (134) is secured to the distal end of sheath (132). As best seen in FIGS. 5-6B, end effector (140) comprises an ultrasonic blade (142) and a clamp arm (144). Ultrasonic blade (142) extends distally from cap (134). Of course, cap (134) is merely optional and may be omitted if desired. Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 6A-6B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 6A. By way of example only, such a resilient member may comprise a leaf spring, a torsion spring, and/or any other suitable kind of resilient member.

Referring back to FIG. 4, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (138) to reach ultrasonic blade (142), thereby providing oscillation of ultrasonic blade (142) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071; U.S. Pub. No. 2011/0015660, now U.S. Pat. No. 8,461,744; U.S. Pub. No. 2012/0112687, now U.S. Pat. No. 9,381,058; U.S. Pub. No. 2012/0116265, now abandoned; U.S. Pub. No. 2014/0005701, now U.S. Pat. No. 9,393,037; U.S. Pub. No. 2014/0114334, now U.S. Pat. No. 9,095,367; and/or U.S. patent application Ser. No. 14/031,665, published as U.S. Pub. No. 2015/0080925 on Mar. 19, 2015. Additional merely illustrative variations for instrument (100) will be described in greater detail below. It should be understood that the below described variations may be readily applied to instrument (100) described above and any of the instruments referred to in any of the references that are cited herein, among others.

II. Exemplary Features for Providing Heat Management in an Ultrasonic Surgical Instrument In some instances, one or more regions of instrument (10, 100) may heat up during extended operation of instrument (10, 100) in a surgical procedure. By way of example only, blade (42, 142), clamp arm (44, 144), and/or other portions of instrument (10, 100) may eventually heat up over time. Such heating may be caused by friction and/or other factors. To the extent that the heat is initially generated in one particular component of instrument (10, 100) (e.g., blade (42, 142) or clamp arm (44, 144), etc.), such heat may be gradually transmitted to other portions of instrument (10, 100). It may be desirable to minimize such heating and/or otherwise manage such heating in order to avoid having heated portions of instrument (10, 100) contact tissue that should not be heated. For instance, the operator may wish for end effector (40, 140) to be relatively cool when the operator wishes to use end effector (40, 140) to perform spreading blunt dissections and/or simple tissue grasping, etc. It may also be desirable to minimize heat and/or otherwise manage heat in a way that does not significantly increase the size or operability of instrument (10, 100). Several examples of how heating may be minimized and/or otherwise managed are described in greater detail below; while other examples will be apparent to those of ordinary skill in the art in view of the teachings herein.

In addition to the examples described below, it should be understood that one or more portions of instrument (10, 100) may include a thermal insulator or barrier coating (e.g., a thin coating of thermal insulator or barrier material with a very low thermal conductivity). An example of a thermal insulator or barrier coating is a nanocomposite (e.g., hydro-NM-oxide) in an acrylic resin suspension. An example of such a coating is NANSULATE® coating by Industrial Nanotech, Inc. of Naples, Fla. Additional merely illustrative examples of thermal insulator or barrier coatings include the following: EST 1711 by Ellison Surface Technologies, Inc. of Mason, Ohio; EST 1732 by Ellison Surface Technologies, Inc. of Mason, Ohio; EST 3030 by Ellison Surface Technologies, Inc. of Mason, Ohio; EST 1711+EST 3030 by Ellison Surface Technologies, Inc. of Mason, Ohio; Oxytech V by Techmetals, Inc. of Dayton, Ohio; Alumina Titania; Zirconium Oxide; Aluminum Oxide; and/or various other kinds of coatings, including combinations thereof.

A thermal insulator or barrier coating may be applied to various external surfaces of instrument (10, 100), such as regions of blade (42, 142) that are not intended to contact tissue, clamp arm (44, 144), clamp pad (46, 146), outer sheath (32, 132), cap (134), etc. In addition or in the alternative, such a coating may be applied to various internal surfaces of instrument (10, 100), such as surfaces in generator (16, 116), transducer assembly (12, 112), internal electronics components, etc. In addition to providing a thermal barrier or insulation, such a coating may serve as a corrosion barrier, fire block, etc. In the below examples that include various components that are added to or otherwise incorporated into variations of instrument (10, 100), the coating may also be applied to one or more regions of such components. Other suitable ways in which a thermal coating may be incorporated into instrument (10, 100) and variations thereof will be apparent to those of ordinary skill in the art in view of the teachings herein.

To the extent that any of the examples discussed below are shown and described in the context of a variation of one particular kind of instrument (10 or 100), it should be understood that the same teachings may be readily applied to the other kind of instrument (10 or 100). Each example described below should therefore not be viewed as only having applicability to either instrument (10) or instrument (100). Furthermore, it is contemplated that the teachings below may be readily applied to other kinds of instruments, not just variations of instruments (10, 100).

A. Exemplary Shield Features for Ultrasonic Blade

The examples described below include various sleeves or other shields that may extend around at least a portion of an ultrasonic blade such as blades (42, 142) described above. It should be understood that these sleeves or shields may act as heat shields that prevent tissue from being inadvertently burned by a hot blade (42, 142) as might otherwise occur through direct contact with the portion of blade (42, 142) being shielded by the sleeve/shield. The examples of sleeves or shields may thus serve as a barrier restricting contact between tissue and blades (42, 142). In addition to serving as a barrier, the sleeves or shields described herein may also provide a channel to collect and/or administer a cooling fluid adjacent to blade (42, 142). By way of example only, the sleeves or shields described herein may provide a gap between an inner surface of the sleeve or shield and an outer surface of blade (42, 142). In some instances, this gap may receive vapor that is emitted when an activated blade (42, 142) contacts tissue. The vapor received in the gap may cool blade (42, 142). In addition or in the alternative, a cooling fluid may be communicated to the gap from a fluid source that is proximal to blade (42, 142), and this communicated fluid may cool blade (42, 142).

Various ways in which vapor and/or cooling fluid may be provided in conjunction with a sleeve or shield are disclosed in U.S. Pub. No. 2015/0148832, entitled "Features to Apply Fluid to an Ultrasonic Blade of a Surgical Instrument," published May 28, 2015, the disclosure of which is incorporated by reference herein; U.S. Pub. No. 2016/0143658, entitled "Features to Drive Fluid toward an Ultrasonic Blade of a Surgical Instrument," published May 26, 2016, the disclosure of which is incorporated by reference herein; U.S. Pub. No. 2015/0148833, entitled "Shielding Features for Ultrasonic Blade of a Surgical Instrument," published May 25, 2015, the disclosure of which is incorporated by reference herein; U.S. Pub. No. 2016/0143657, entitled "Features for Communication of Fluid through Shaft Assembly of Ultrasonic Surgical Instrument," published May 26, 2016, the disclosure of which is incorporated by reference herein. Various suitable ways in which the teachings below may be readily combined with the teachings of those references will be apparent to those of ordinary skill in the art.

It should be understood that any of the sleeves or shields described below may comprise a temperature sensitive material. For instance, such a temperature sensitive material may be configured to change color and/or otherwise change in appearance in response to changes in temperature. In some such examples, the sleeve or shield may change color as the temperature of the blade (42, 142) that is adjacent to the sleeve or shield increases. The sleeve or shield may thus provide the operator with a visual indication of the thermal condition of blade (42, 142) and/or the rest of end effector (40, 140). Various suitable materials that may be used to provide such properties will be apparent to those of ordinary skill in the art in view of the teachings herein. By way of example only, such material may include Huntsman Ren-Shape 7820.

In some versions, one or more of the sleeves described below comprises Polybenzimidazole-Polyetherketoneketone (PBI-PEKK). As another merely illustrative example, one or more of the sleeves described below may comprise Perfluoroalkoxy (PFA). In addition or in the alternative, any of the sleeves described herein may comprise glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos Nano-Tool. Still other suitable materials that may be used to form the sleeves described below will be apparent to those of ordinary skill in the art in view of the teachings herein. Similarly, various suitable methods for forming sleeves (e.g., injection molding, SLA, etc.) will be apparent to those of ordinary skill in the art in view of the teachings herein.

1. Exemplary Instrument with Removable Blade Sleeve

Figure 7B:
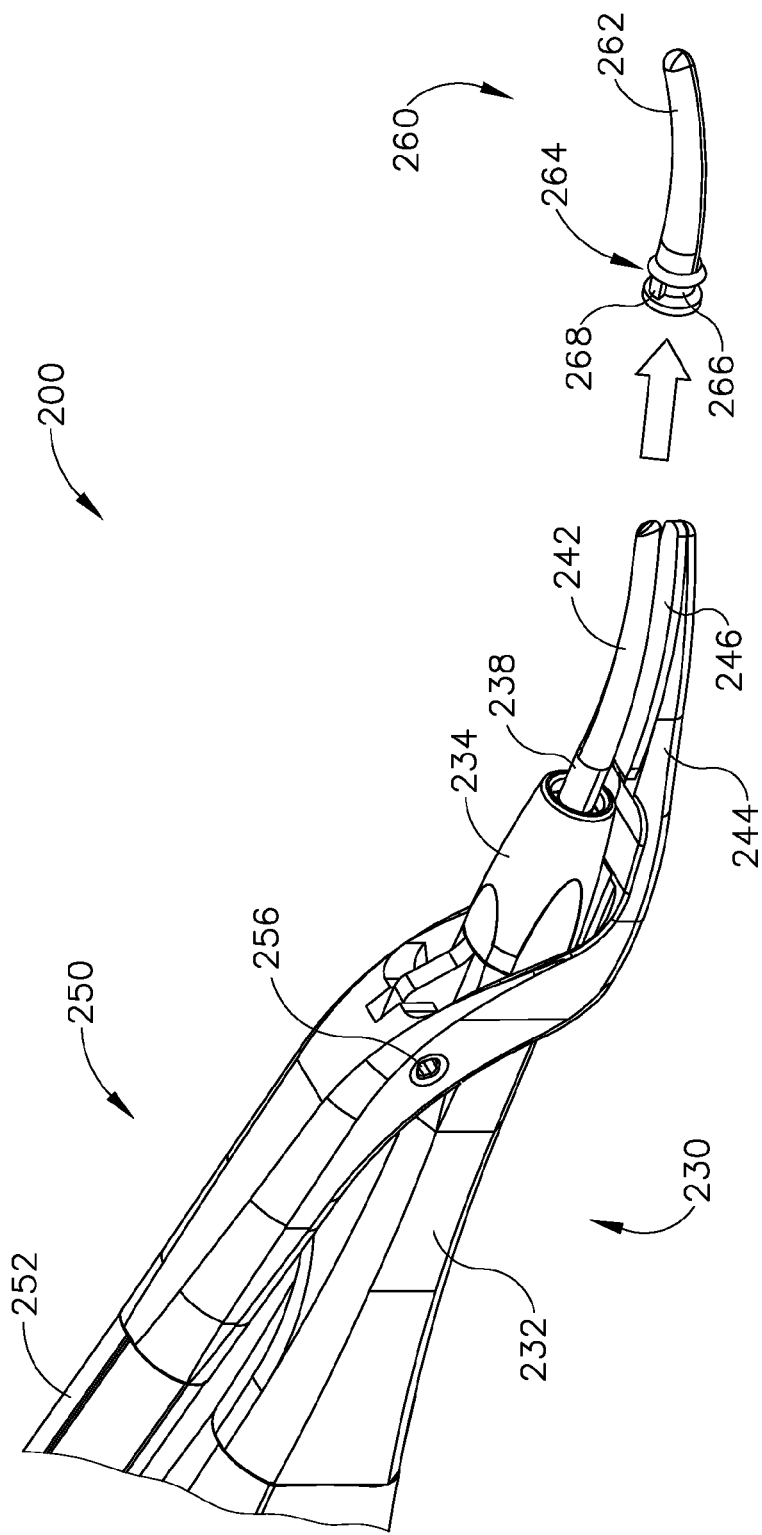
FIG. 7B depicts a detailed perspective view of the end effector of FIG. 7A, with the blade sleeve removed.
Figure 8:
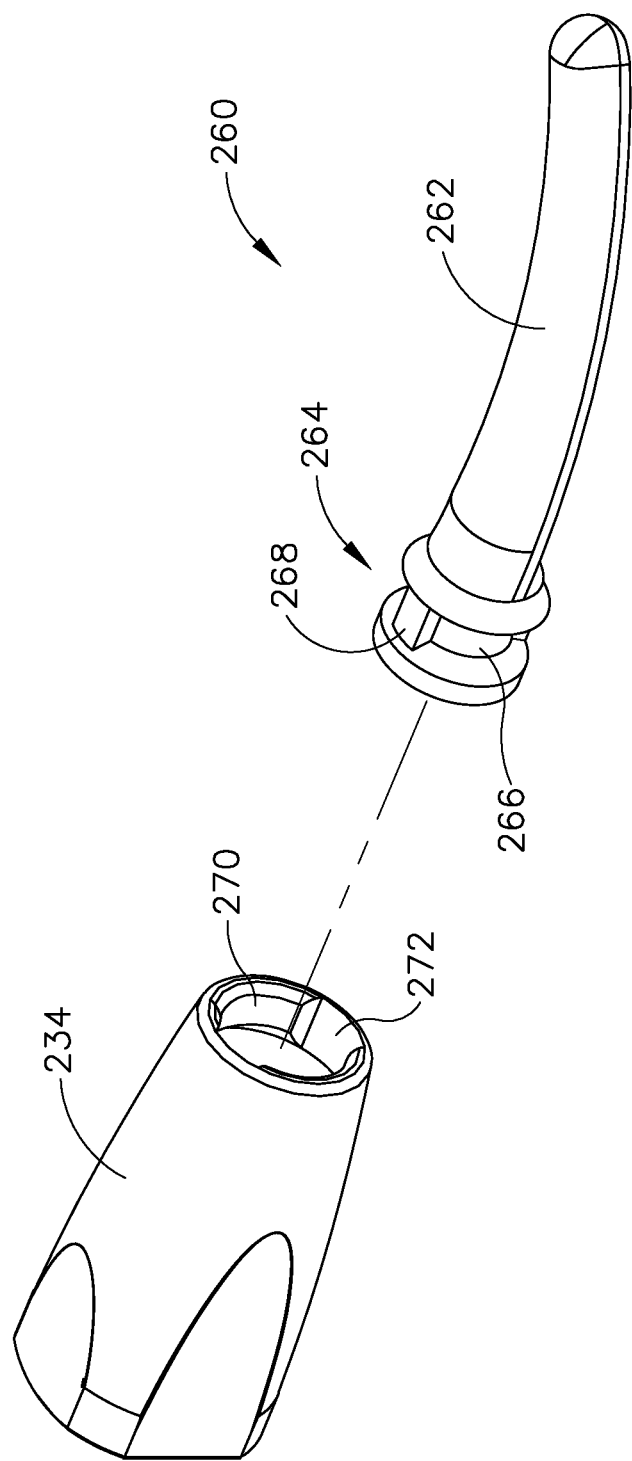
FIG. 8 depicts a detailed perspective view of the removable blade sleeve of FIG. 7A.

FIGS. 7A-8 show an exemplary instrument (200) that is equipped with a removable blade sleeve (260). Instrument (200) of this example is substantially the same as instrument (100) described above, except as otherwise noted herein. Although instrument (200) is shown as being substantially the same as instrument (100), it should be understood that the teachings herein may be readily incorporated with instrument (10), described above. Like with instrument (100), instrument (200) includes a shaft assembly (230), an end effector (240), and a clamp arm assembly (250). Shaft assembly (230) comprises an outer sheath (232), and a cap (234). Outer sheath (232) extends distally from body (not shown) and houses a waveguide (238). Cap (234) is secured to outer sheath (232) and selectively secures sleeve (260) to instrument (200), as will be described in greater detail below.

End effector (240) includes blade (242) and clamp arm (244). Clamp arm (244) is attached to a shank (252) of clamp arm assembly (250) and is pivotable about pin (256). As with instrument (100), clamp arm (244) includes a clamp pad (246), which compresses tissue against blade (242) when clamp arm assembly (250) is pivoted about pin (256) toward blade (242).

Sleeve (260) is configured to cover the outer portion of blade (242) to protect tissue from inadvertent contact with blade (242) and to further dissipate excess heat from blade (242). In this context, the "outer portion" of blade (242) includes the region of blade (242) that tissue will not be compressed against when clamp arm (244) is pivoted to a closed position. As will be described in greater detail below, sleeve (260) may be comprised of any suitable material such as rigid thermoplastic, silicon, and/or other material(s). Sleeve (260) includes a blade cover portion (262) and a cap portion (264). Blade cover portion (262) extends distally from cap portion (264) with a generally semi-circular shape providing exposure of the inner portion of blade (242). In this context, the "inner portion" of blade (242) includes the region of blade (242) that tissue will be compressed against when clamp arm (244) is pivoted to a closed position.

Thus, blade (242) is only partially covered by blade cover portion (262) such that tissue may still contact blade (242) directly when the tissue is clamped between blade (242) and clamp pad (246). As blade cover portion (262) extends distally, a slight longitudinal bend is formed. The shape of blade cover portion (262) generally corresponds to the shape of blade (242). In other examples, blade cover portion (262) may have a different shape corresponding to a differently shaped blade (242). Although blade cover portion (262) is shown as extending distally for the full length of blade (242), it should be understood that in other examples (such as those described below) blade cover portion (262) may extend distally for only a portion of the length of blade (242), if desired.

As can best be seen in FIGS. 7B and 8, cap portion (246) is generally circular in shape and may completely surround waveguide (238) and/or blade (242) when blade sleeve (260) is attached to cap (234). Cap portion (246) comprises a recessed portion (266) and a protruding poka-yoke feature (268). Recessed portion (266) and poka-yoke feature (268) engage a corresponding protruding portion (270) and recessed poka-yoke feature (272) that are integral to the internal diameter of cap (234). Thus, recessed portion (266) is operable to removably secure blade sleeve (260) to cap (234) via protruding portion (270) of cap (234). Moreover, poka-yoke features (268, 276) work cooperatively to ensure proper orientation of blade sleeve (260) relative to blade (242) and to further prevent rotation of blade sleeve (260) while instrument (200) is in use.

In an exemplary mode of operation, instrument (200) may be equipped with blade sleeve (260) and an operator may selectively remove blade sleeve (260) during a procedure to clean blade (242) or to use instrument (200) without blade sleeve (260). To further assist with cleaning of blade (242), blade (242) may be coated with a parylene coating, which may act as a non-stick finish on blade (242). It should be understood that the inner surfaces and edges of blade sleeve (260) may collectively serve as a wiper, wiping off coagulated blood, other debris, and/or fluids, etc. from blade (242) when blade sleeve (260) is removed from blade (242). After blade sleeve (260) is pulled off of blade (242), the same blade sleeve (260) or another blade sleeve (260) may be placed back on blade (242) for further use. Other suitable ways in which blade sleeve (260) may be used will be apparent to those of ordinary skill in the art in view of the teachings herein. It should be understood from the foregoing that, in the present example, blade sleeve (260) is translated along a longitudinal path in order to couple blade sleeve (260) with instrument (200) and decouple blade sleeve (260) from instrument (200).

2. Exemplary Instrument with Removable Cap and Blade Sleeve

Figure 9:
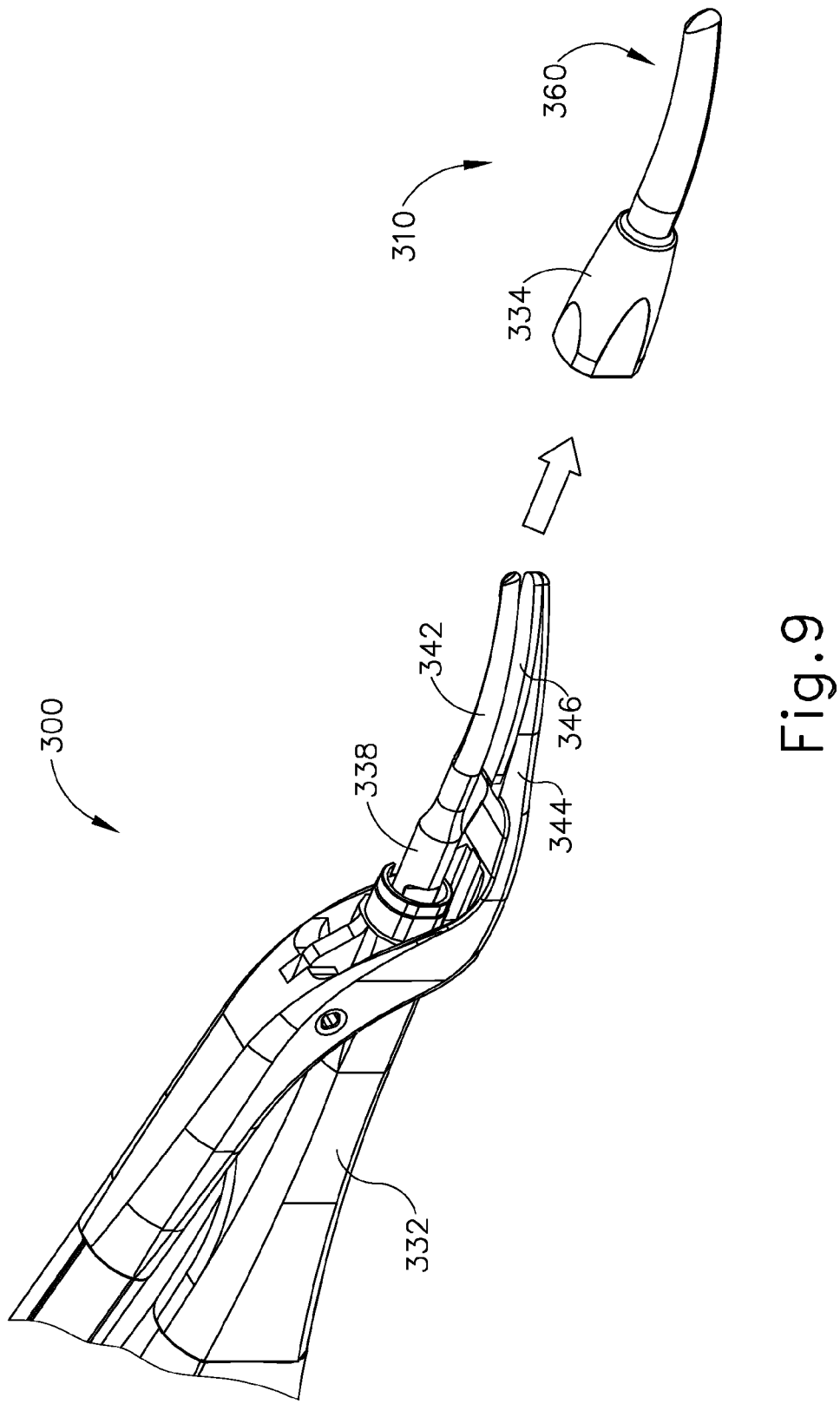
FIG. 9 depicts a detailed perspective view of an end effector of another exemplary alternative instrument that includes a removable cap and blade sleeve, with the cap and blade sleeve removed.

FIG. 9 shows an exemplary instrument (300) that is equipped with a removable assembly (310) that is formed by a cap (334) and a blade sleeve (360). Instrument (300) is substantially the same as instruments (100, 200) described above, except as otherwise noted herein. Although instrument (200) is shown as being substantially the same as instrument (100), it should be understood that the teachings herein may be readily incorporated with instrument (10), described above. Like with instrument (200), instrument (300) includes cap (334), which is attachable to an outer sheath (332) to partially shield a waveguide (338) extending through outer sheath (332). Instrument (300) similarly includes end effector (340), which includes a blade (342) and a clamp arm (344). Clamp arm (344) is pivotable such that tissue may be compressed between blade (342) and a clamp pad (346) of clamp arm (344).

Unlike instrument (200), cap (334) of instrument (300) is unitarily secured to sleeve (360) yet is selectively removable from outer sheath (332). Thus, the primary difference between instrument (200) and instrument (300) is that cap (334) is selectively removable from instrument (300) to remove sleeve (360). Cap (334) may be attachable to outer sheath (332) using any suitable features. For instance, in some examples cap (334) may utilize a similar protrusion and recess system as described above with respect to sleeve (260). Yet in other examples, an entirely different set of attachment features may be used such as those described in greater detail below. Other suitable attachment features that may be used will be apparent to those of ordinary skill in the art in view of the teachings herein.

In an exemplary mode of operation, instrument (300) may initially be equipped with assembly (310) and an operator may selectively remove assembly (310) during a procedure to clean blade (342) or to use instrument (300) without assembly (310). To further assist with cleaning of blade (342), blade (342) may be coated with a parylene coating, which may act as a non-stick finish on blade (342). It should be understood that the inner surfaces and edges of sleeve (360) may collectively serve as a wiper, wiping off coagulated blood, other debris, and/or fluids, etc. from blade (342) when sleeve (360) is removed from blade (342). Assembly (310) may also be cleaned in conjunction with cleaning of blade (342). Assembly (310) may also be similarly coated with a parylene coating to act as a non-stick finish. After assembly (310) has been removed from instrument (300), assembly (310) may be reattached to instrument (300). Alternatively, assembly (310) may be replaced with a new cap assembly (310) and the used assembly (310) may be discarded. It should be understood from the foregoing that, in the present example, assembly (310) is translated along a longitudinal path in order to couple assembly (310) with instrument (300) and decouple assembly (310) from instrument (300).

3. Exemplary Alternative Features for Attaching Sleeve

Although some examples for attaching blade sleeves (260, 360) to instruments (200, 300) are described above, it should be understood that blade sleeves (260, 360) may be attached to instruments (200, 300) in numerous other ways. Several suitable alternative means of attachment are described below. It should be understood that, while the examples described below may be described in connection with a certain instrument (10, 100), the examples may be readily applied to any other instrument (10, 100, 200, 300) described herein.

Figure 10:
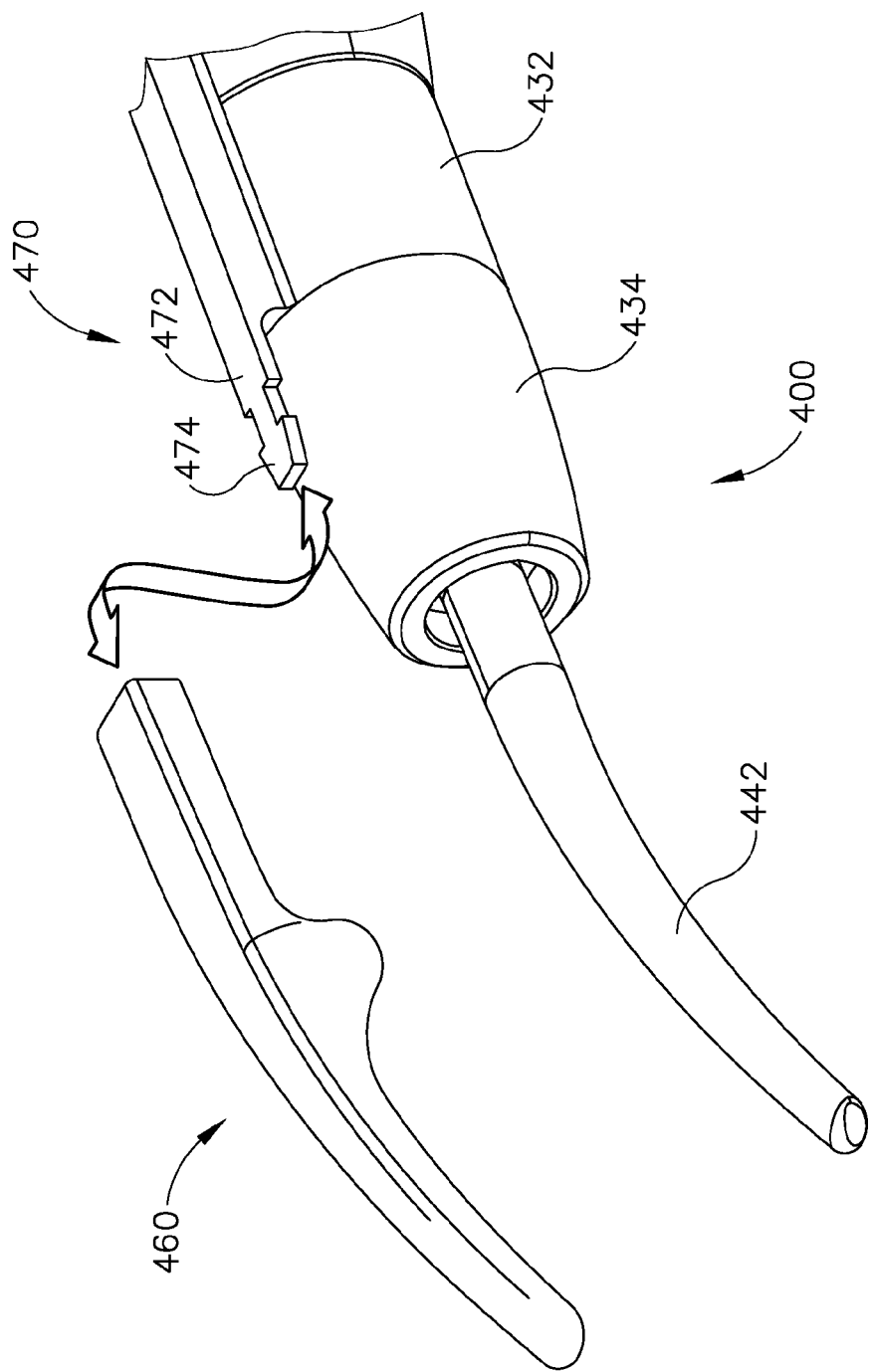
FIG. 10 depicts a detailed perspective view of an end effector of another exemplary alternative instrument that includes a removable blade sleeve, with the blade sleeve removed.

FIG. 10 shows an exemplary alternative end effector (400), which includes a selectively attachable blade sleeve (460) and a blade (442) protruding from a cap (434). It should be understood that end effector (400) may be readily incorporated into any instrument (10, 100, 300) described herein. Cap (434) is securely attached to an outer sheath (432). Blade sleeve (460) is selectively attachable to outer sheath (432) via an attachment rail (470). In particular, attachment rail (470) includes a distal attachment portion (472) extending outwardly above cap (434) such that attachment portion (472) is positioned above cap (434). Attachment portion (472) defines a snap fit barb member (474), which is configured to engage a corresponding member (not shown) inside of sleeve (460). In other words, attachment portion (472) is insertable into the proximal end of sleeve (460) where snap fit barb member (474) forms a snap fit with sleeve (460), thereby selectively attaching sleeve (460) to end effector (400). Sleeve (460) may thus be secured to end effector (400) by first properly positioning sleeve (460) in relation to blade (442) and then translating sleeve (460) along a longitudinal path to insert snap fit barb member (474) in the proximal end of sleeve (460). Other than having different attachment features, sleeve (460) may be otherwise configured and operable similar to blade sleeves (260, 360) described above.

Figure 11:
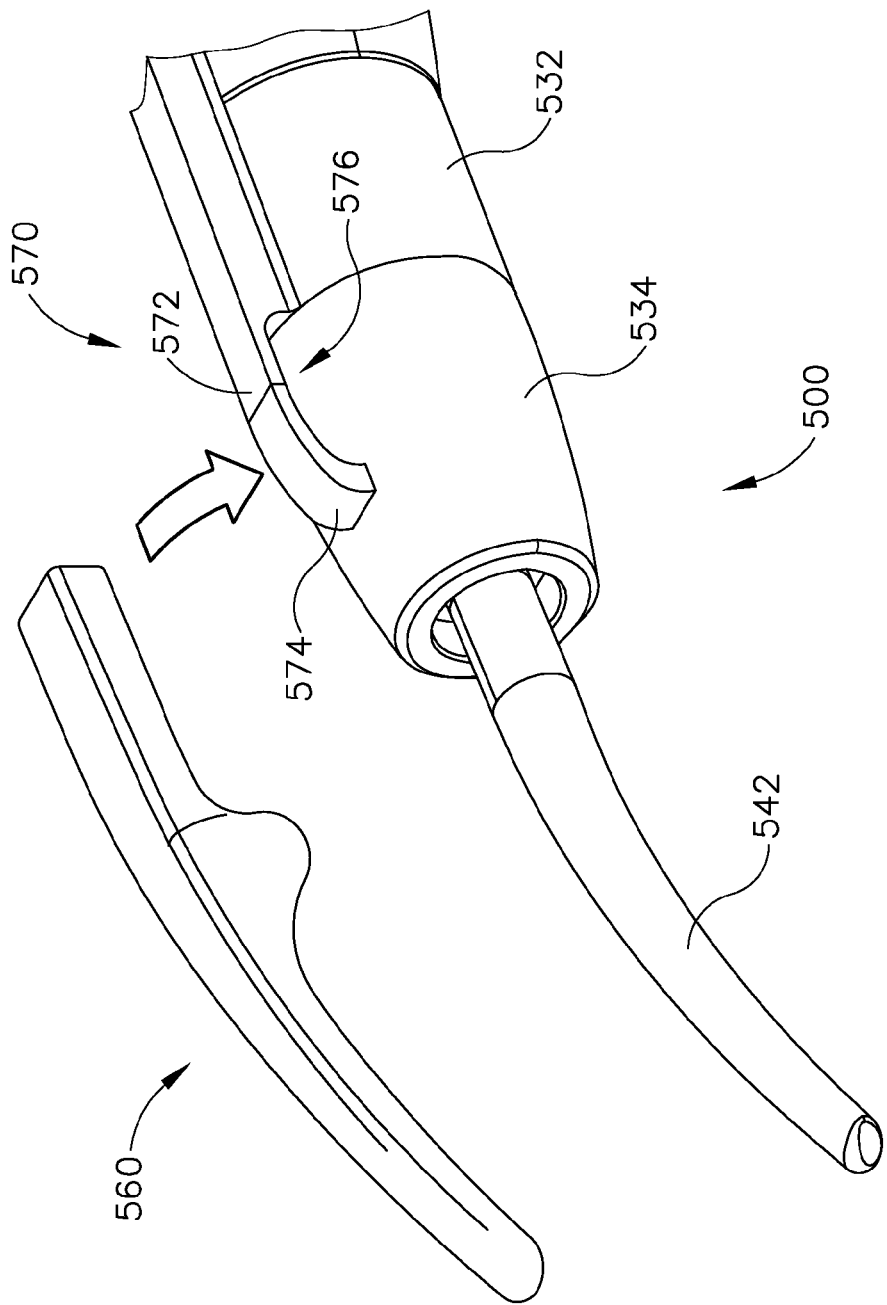
FIG. 11 depicts a detailed perspective view of an end effector of another exemplary alternative instrument that includes a removable blade sleeve, with the blade sleeve removed.
Figure 12:
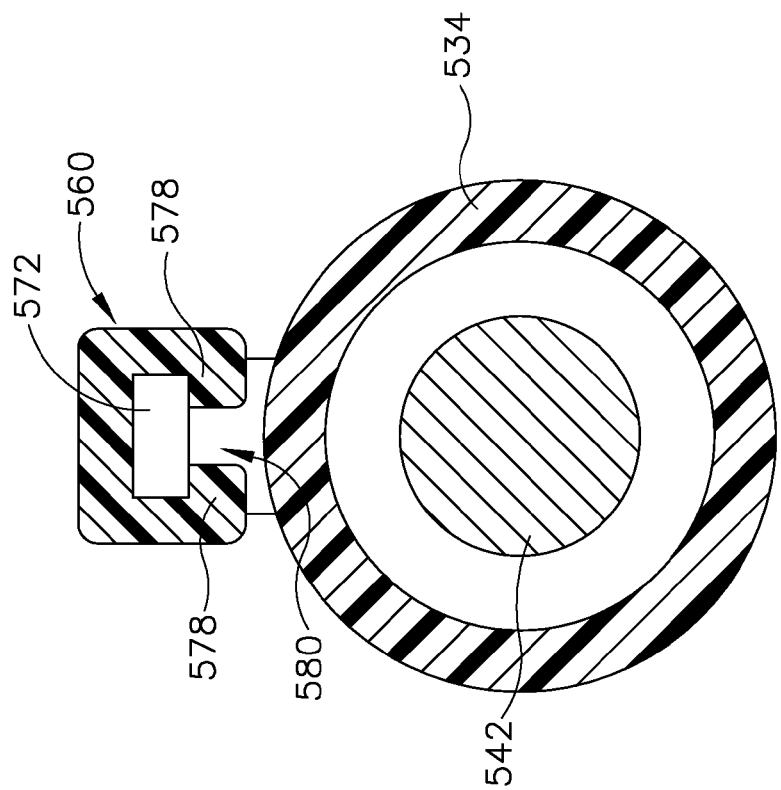
FIG. 12 depicts a cross-sectional end view of the end effector of FIG. 11, with the blade sleeve attached to the instrument.

FIGS. 11-12 show another exemplary end effector (500), which includes a selectively attachable blade sleeve (560) and a blade (542) protruding from a cap (534). It should be understood that end effector (500) may be readily incorporated into any instrument (10, 100, 300) described herein. Cap (534) is securely attached to an outer sheath (532). Blade sleeve (560) is selectively attachable to outer sheath (532) via an attachment rail (570). In particular, attachment rail (570) includes a distal attachment portion (572) extending outwardly above cap (534) such that attachment portion (572) is positioned above cap (534). Attachment portion (572) also includes a distal end (574), which curves downwardly away from the longitudinal axis of attachment rail (570) toward cap (534). Attachment portion (572) thus forms an opening (576) that may permit engagement of sleeve (560) with attachment portion (572).

As can be seen in FIG. 12, sleeve (560) includes two tabs (578), which together form a channel (580) in sleeve (560). Channel (580) is configured to receive attachment portion (572) such that sleeve (560) may be removably attached to instrument (500). Tabs (578) are comprised of a resiliently biased material to permit attachment member (572) to resiliently engage with sleeve (560). Tabs (578) may thus provide a snap fit with rail (570). Accordingly, sleeve (560) may be relatively securely fastened to instrument (500) via attachment portion (572) until an operator desires to remove sleeve (560) (e.g., for cleaning purposes, etc.). An operator may then apply a sufficient amount of force to overcome the resilient bias of tabs (578), thereby removing sleeve (560) from instrument (500). Sleeve (560) may thus be secured to end effector (500) and removed from end effector (500) by translating sleeve (560) along a path that is transverse to the longitudinal axis of sheath (532). Other than having different attachment features, sleeve (560) may be otherwise configured and operable similar to blade sleeves (260, 360) described above.

Figure 13:
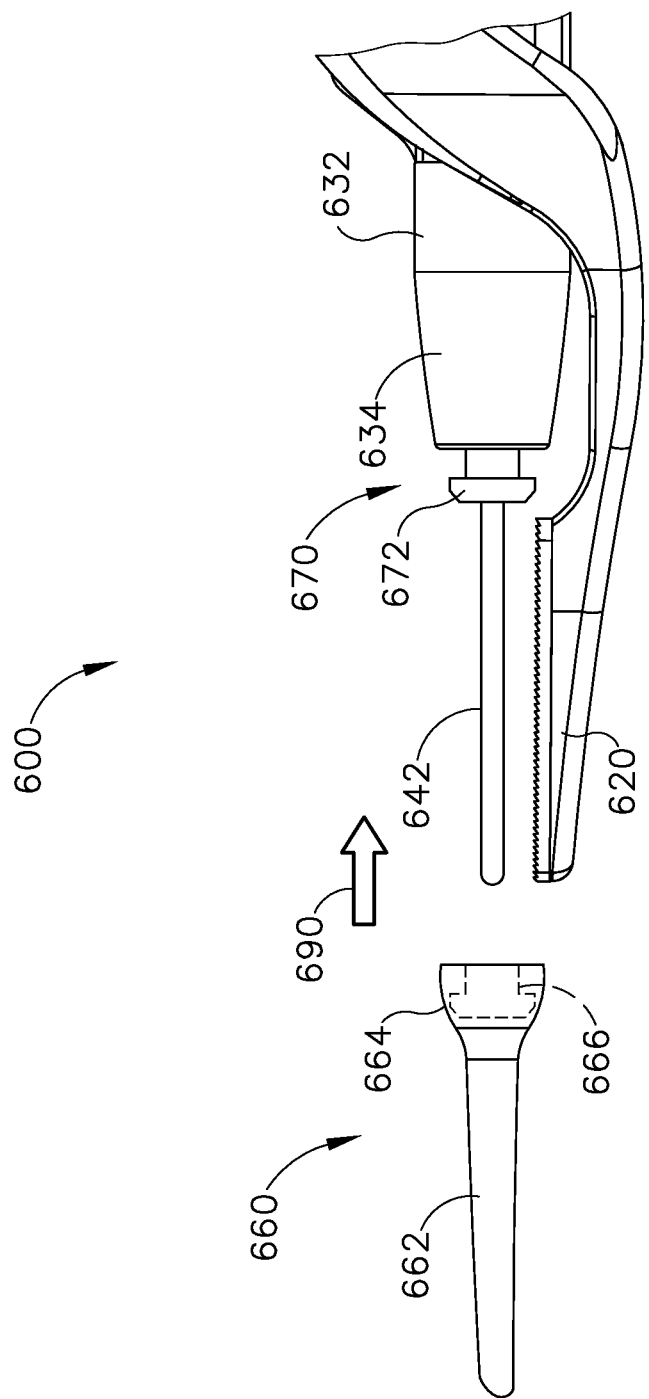
FIG. 13 depicts a side elevational view of an end effector of another exemplary alternative instrument that includes a removable blade sleeve, with the blade sleeve removed.

FIG. 13 shows another exemplary instrument (600), which includes a selectively attachable blade sleeve (660). Instrument (600) further comprises a clamp arm (620) and a blade (642) protruding from a cap (634). Cap (634) is securely attached to an outer sheath (632). Blade sleeve (660) is selectively attachable to cap (634) via an attachment member (670). In particular, attachment member (670) extends distally from cap (634) and includes a distal attachment portion (672). Attachment portion (672) extends outwardly from the perimeter of attachment member (670) forming a barb. As will be described in greater detail below, sleeve (660) is configured to selectively engage attachment portion (672) to thereby selectively attach sleeve (660) to instrument (600).

Sleeve (660) comprises a distal blade cover portion (662) and a proximal ferrule portion (664). Blade cover portion (662) is substantially the same as blade cover portion (262), described above such that it will not be described in greater detail here. Ferrule portion (664) includes an engagement feature (666) (shown in phantom), which is complementary to the shape of attachment member (670). In the present example, ferrule portion (664) is comprised of a resiliently biased or elastomeric material such that ferrule portion (664) is deformable to receive attachment member (670). In some versions, blade cover portion (662) is formed of a soft, flexible silicone material; while ferrule portion (664) is formed of a harder yet resilient plastic material. Portions (662, 664) may be removably coupled together, fixedly coupled together, or otherwise coupled together in any suitable fashion.

In an exemplary mode of operation, sleeve (660) is attachable to instrument (600) by a user applying a force to sleeve (660) in the longitudinal direction indicated by arrow (690) in FIG. 13. In particular, ferrule portion (664) of sleeve (660) is forced outwardly by the shape of attachment portion (672) of attachment member (670). Once ferrule portion (664) is fully engaged with attachment member (670), ferrule portion (664) returns to its original shape and is retained in place by engagement between engagement feature (666) of ferrule portion (664) and attachment portion (672) of attachment member (670). Sleeve (660) may later be selectively removed from instrument (600) by applying a similar force in a direction opposite of the arrow (690) in FIG. 13.

4. Exemplary Blade Sleeves of Variable Coverage of Blade

In some examples it may be desirable for blade sleeves (260, 360) to only partially cover blade (242, 342). For instance, in such examples blade sleeves (260, 360) may beneficially remove excess heat and protect against inadvertent contact with tissue, yet the shortened length relative to blade (242, 342) may beneficially allow for increased visibility of blade (242, 342) and/or increased exposed regions for intentional contact with tissue. It should be understood that while the blade sleeves described below may be discussed in the context of instruments similar to instrument (100), the blade sleeves may be readily combined with instruments (10, 200, 300, 400, 500, 600) discussed herein.

Figure 14:
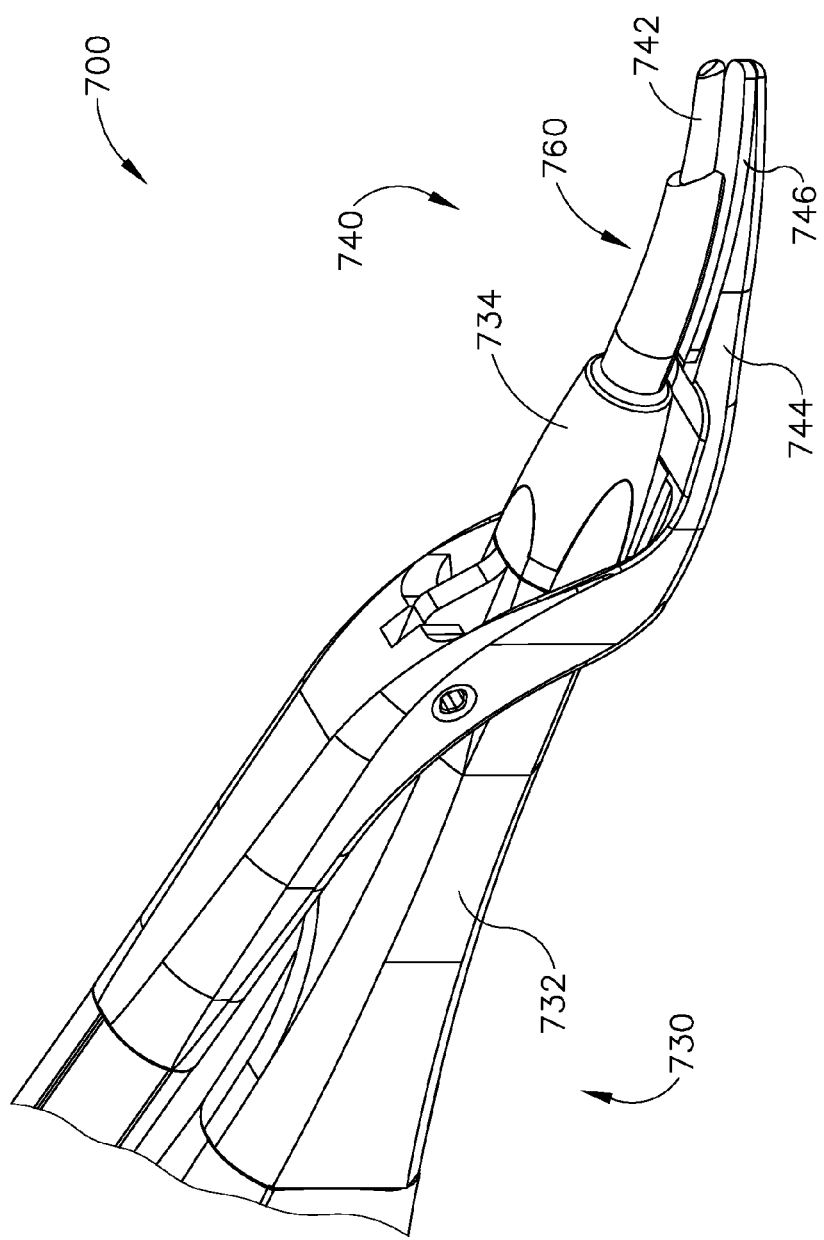
FIG. 14 depicts a detailed perspective view of an end effector of another exemplary alternative instrument that includes a blade sleeve partially covering a ultrasonic blade.

FIG. 14 shows an exemplary alternative instrument (700) having a shortened blade sleeve (760). Instrument (700) is substantially similar to instrument (100) described above except as otherwise noted below. In particular, instrument (700) includes a shaft assembly (730) and an end effector (740). Shaft assembly (730) comprises an outer sheath (732) and a cap (734) attached to outer sheath (732). Sleeve (760) extends distally from cap (734). End effector (740) comprises an ultrasonic blade (742) and a clamp arm (744), which is pivotable relative to blade (742) to clamp tissue between a clamp pad (746) of clamp arm (744) and blade (742).

Sleeve (760) is substantially the same as sleeves (260, 360) described above except sleeve (760) extends distally relative to blade (742) for only two thirds of the length of blade (742) instead of the full length of blade. Accordingly, the distal region of blade (742) may be at least partially visible during use of instrument (700). However, because sleeve (760) covers two thirds of the length of blade (742), sleeve (760) may still protect tissue from inadvertent contact with blade (742) and may remove excess heat from blade (742). By having sleeve (760) extend along only a portion of the length of blade (742), a back portion of the distal region of blade (742) is fully exposed, allowing that exposed back portion of the distal region of blade (742) to be used to perform back cutting and/or other procedures (e.g., uses where clamp arm (744) is not used to compress tissue against the front portion of blade (742), etc.).

Figure 15:
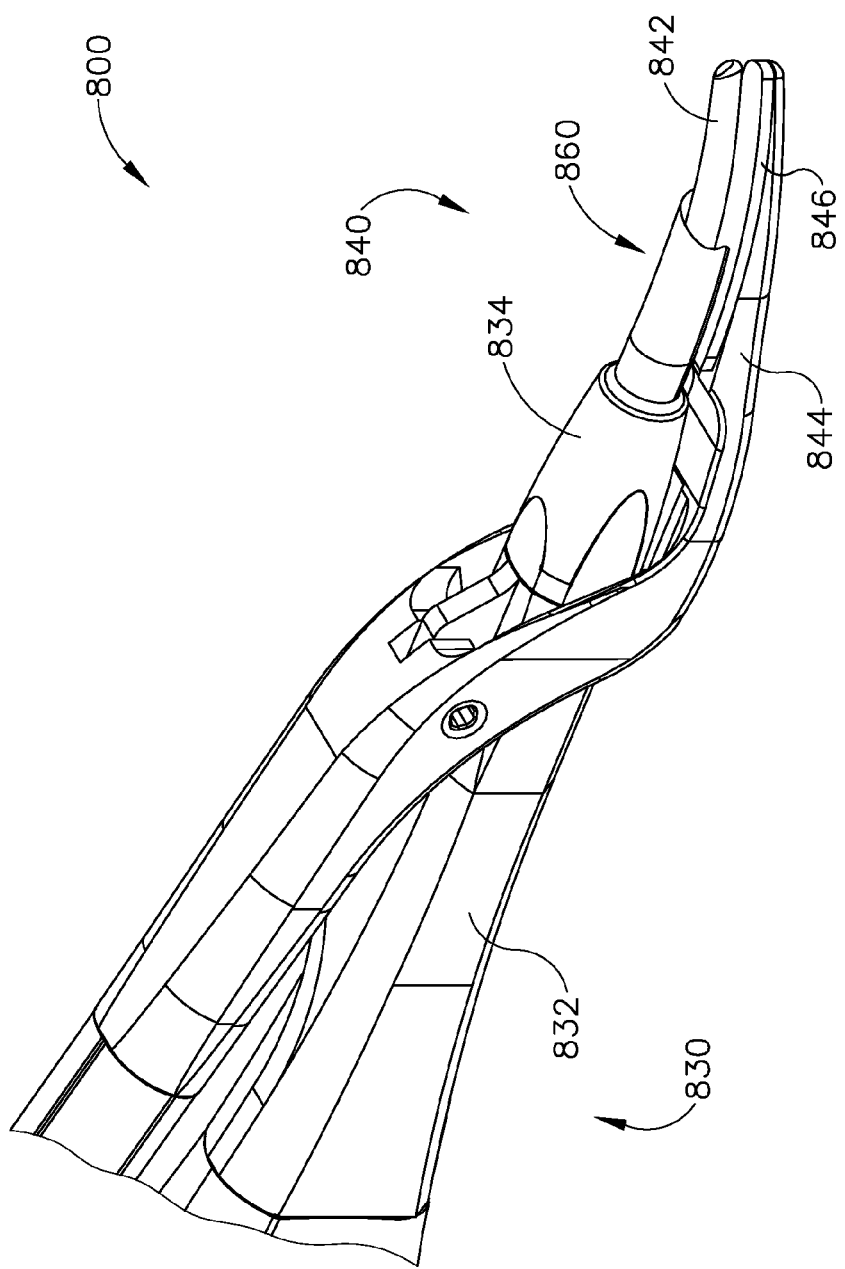
FIG. 15 depicts a detailed perspective view of an end effector of another exemplary alternative instrument that includes a blade sleeve partially covering a ultrasonic blade.

FIG. 15 shows an exemplary alternative instrument (800) having a shortened blade sleeve (860), which is similar to blade sleeve (760) described above. Instrument (800) is substantially similar to instrument (100) described above except as otherwise noted below. In particular, instrument (800) includes a shaft assembly (830) and an end effector (840). Shaft assembly (830) comprises an outer sheath (832) and a cap (834) attached to outer sheath (832). Sleeve (860) extends distally from cap (834). End effector (840) comprises an ultrasonic blade (842) and a clamp arm (844), which is pivotable relative to blade (842) to clamp tissue between a clamp pad (846) of clamp arm (844) and blade (842).

Sleeve (860) is substantially the same as sleeves (260, 360, 760) described above, except sleeve (860) extends distally relative to blade (842) for only one half of the length of blade (842) instead of the full length of blade. Accordingly, the distal region of blade (842) may be at least partially visible during use of instrument (800). However, because sleeve (860) covers one half of the length of blade (842), sleeve (860) may still protect tissue from inadvertent contact with blade (842) and may remove excess heat from blade (842). Again, by having sleeve (860) extend along only a portion of the length of blade (842), a back portion of the distal region of blade (842) is fully exposed, allowing that exposed back portion of the distal region of blade (842) to be used to perform back cutting and/or other procedures (e.g., uses where clamp arm (844) is not used to compress tissue against the front portion of blade (842), etc.). This same principle may be applied to any other sleeve or similar feature described herein.

Although sleeves (760, 860) described above are shown as covering two thirds and one half of the length of blades (742, 842), respectively, it should be understood that in other examples, sleeves (760, 860) may cover any suitable length of the blade from just over 0 percent to 100 percent. It should be further understood that, in some examples, sleeves (760, 860) may extend even further than the full length of blades (742, 842). In such examples, the additional length of sleeves (760, 860) may be used to support an electrode for the emission of RF electro surgical current, which may be used to cut and/or seal tissue. Additionally, clamp arm (744, 844) may extend for a similar length to support another opposing charged electrode (e.g., when a bi-polar system is used).

Versions employing RF energy to cut and/or seal tissue may be constructed and operable in accordance with at least some of the teachings of U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; and/or U.S. Pat. No. 7,381,209, entitled "Electrosurgical Instrument," issued Jun. 3, 2008, the disclosure of which is incorporated by reference herein.

5. Exemplary Blade Sleeve with Dissection Tip

In some examples it may be desirable for an instrument, similar to instruments (10, 100) described above, to include a passive blunt dissection tip. Such blunt dissection tips may be useful for manipulating tissue in preparation for cutting and sealing by an ultrasonic blade of the instrument. Although the example described below is discussed in the context of an instrument similar to instrument (100), it should be understood that the features or concepts described below may be readily combined with any of the other instruments described herein as will be apparent to those of ordinary skill in the art in view of the teachings herein.

Figure 16:
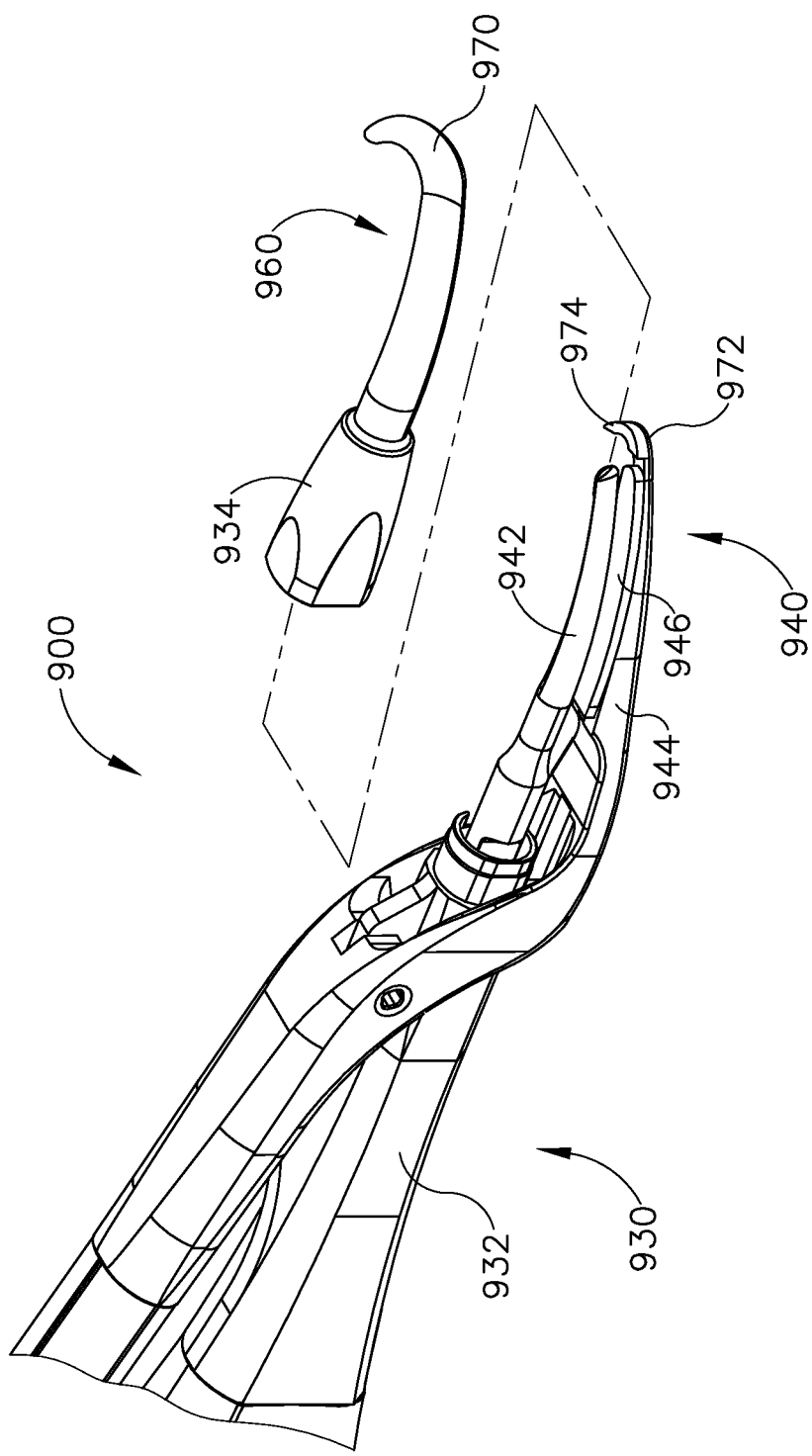
FIG. 16 depicts a detailed perspective view of an end effector of another exemplary alternative instrument that includes a blade sleeve having a dissection tip.

FIG. 16 shows an exemplary alternative instrument (900), which incorporates a blade sleeve (960) having a dissection tip (970). Instrument (900) is substantially similar to instrument (100) described above except as otherwise noted below. In particular, instrument (900) comprises a shaft assembly (930) and an end effector (940). Shaft assembly (930) comprises an outer sheath (932) and a cap (934) attached to outer sheath (932). Sleeve (960) extends distally from cap (934). End effector (940) comprises an ultrasonic blade (942) and a clamp arm (944), which is pivotable relative to blade (942) to clamp tissue between a clamp pad (946) of clamp arm (944) and blade (942).

Sleeve (960) is substantially the same as sleeves (260, 360), described above, except sleeve (960) includes a blunt dissection tip (970) extending along an axis at an angle of approximately 90° relative to the longitudinal axis of sleeve (960). In some versions, sleeve (960) is fully rigid. Clamp arm (944) includes a corresponding distal extension (972), which extends along the same axis as dissection tip (970). It should be understood that the 90° extension of dissection tip (970) and distal extension (972) is merely exemplary and in other examples the angle of extension may be varied (e.g., less than 90° or greater than 90°) as will be apparent to those of ordinary skill in the art in view of the teachings herein. Clamp arm (944) further includes a distal pad (974) that is configured to grasp tissue. Accordingly, dissection tip (970) of sleeve (960) and distal extension of (972) may be used to clamp tissue between distal pad (974) and dissection tip (970). Although not shown, it should be understood that dissection tip (970) may also include a pad similar to distal pad (974) to further enhance the grasping ability of dissection tip (970).

As can be seen, dissection tip (970) and distal extension (972) are positioned distally of blade (942) such that blade (942) does not engage tissue when only dissection tip (970) is used to grasp tissue. Dissection tip (970) of the present example is oriented for use when instrument (900) is being grasped by a right hand of a user. However, it should be understood that dissection tip (970) may be oriented in the opposite direction such that instrument may be used with a left hand of a user. It should also be understood that while dissection tip (970) and distal extension (972) are shown as being oriented along the same grasping plane as blade (942) and clamp pad (946), in other examples dissection tip (970) and distal extension (972) may be oriented along an entirely different grasping plane.

6. Exemplary Blade Sleeve with Light Emitting Feature

Figure 17:
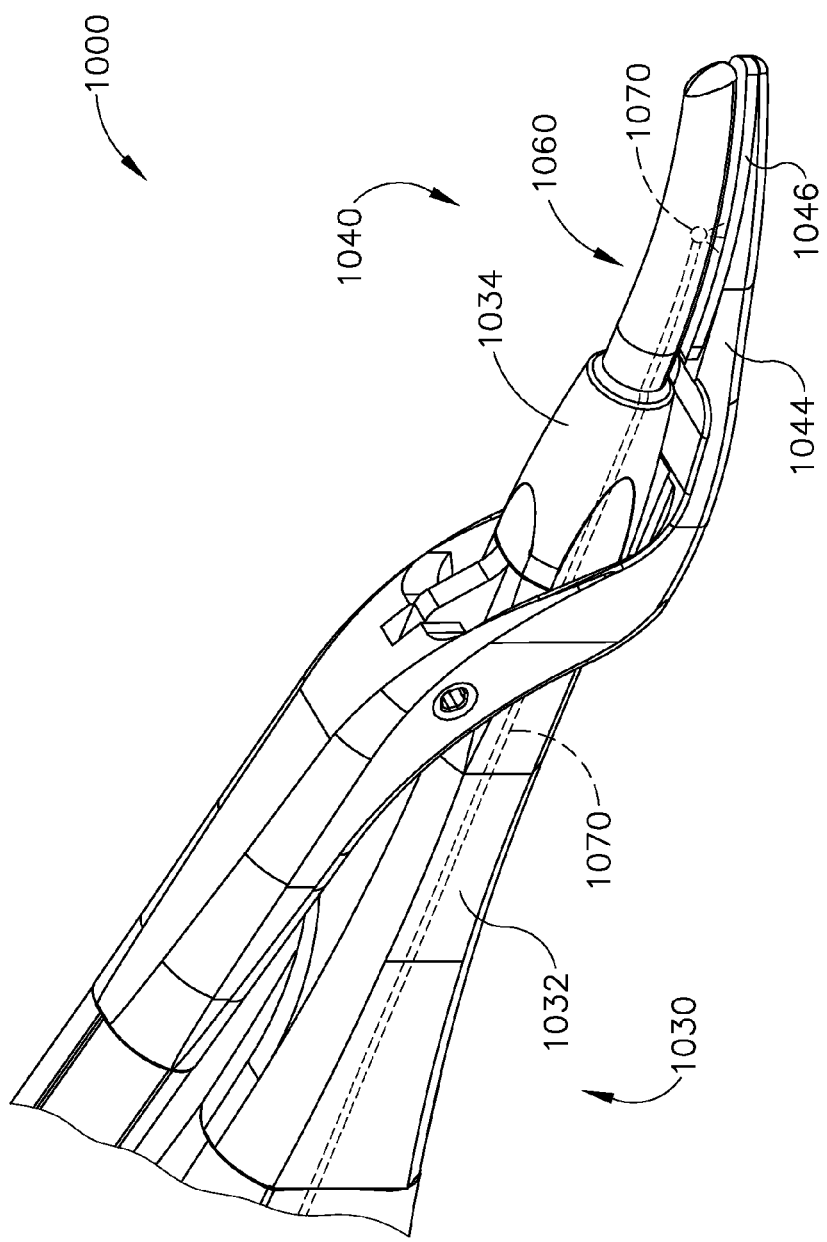
FIG. 17 depicts a detailed perspective view of an end effector of another exemplary alternative instrument that includes a blade sleeve having a light emitting feature.

FIG. 17 shows an exemplary alternative instrument (1000), which incorporates a blade sleeve (1060) having a light emitting feature (1070). Instrument (1000) is substantially similar to instrument (100) described above except as otherwise noted below. In particular, instrument (1000) comprises a shaft assembly (1030) and an end effector (1040). Shaft assembly (1030) comprises an outer sheath (1032) and a cap (1034) attached to outer sheath (1032). Sleeve (1060) extends distally from cap (1034). End effector (1040) comprises an ultrasonic blade (not shown) and a clamp arm (1044), which is pivotable relative to the blade to clamp tissue between a clamp pad (1046) of clamp arm (1044) and the blade.

Sleeve (1060) includes a light emitting feature (1070), which is shown in phantom in FIG. 17. Light emitting feature (1070) of the present example receives light via optical fiber (1072). The proximal end of optical fiber (1072) may receive light from any suitable source. Optical fiber (1072) extends within outer sheath (1032) distally through cap (1034) to sleeve (1060). Optical fiber (1072) may be comprised of a single illuminating fiber, or a bundle of several fibers. Accordingly, optical fiber (1072) communicates visible light from the light source (not shown) to light emitting feature (1070). Light emitting feature (1070) may comprise features such as lenses, mirrors, and/or reflective surfaces to direct and focus the light communicated by optical fiber (1072). In an exemplary mode of operation, light emitting feature (1070) illuminates the area surrounding end effector (1040) to thereby increase visibility.

Although light emitting feature (1070) of the present example utilizes fiber optics to deliver light to end effector (1040), it should be understood that in other examples light emitting feature (1070) comprise a light source such as a light emitting diode; and optical fiber (1072) may comprise an electrical wire. Regardless, light emitting feature (1070) may be duplicated in other examples with a plurality of light emitting features (1070) positioned in different points in sleeve (1060). Yet in other examples, light emitting feature (1070) may be in a different position than the position depicted in FIG. 17. For instance, light emitting feature (1070) may be positioned on the distal and/or proximal ends of sleeve (1060). Alternatively, light emitting feature (1070) may be positioned on another feature entirely such as on clamp arm (1044). Other suitable positions for one or more light emitting features (1070) will be apparent to those of ordinary skill in the art in view of the teachings herein.

B. Exemplary Stiffening Features for Blade Sleeve

In some instances, it may be desirable to stiffen a blade sleeve similar to blade sleeves (260, 360) described above. Such stiffening may be desirable when sleeve (260, 360) is made of a flexible material such as silicone, etc. In particular, such stiffening may be desirable to substantially maintain the position of sleeve (260, 360) so that sleeve (260, 360) will continue to serve as an effective heat shield for blade (242, 342); and/or so that sleeve (260, 360) will continue to effectively provide a channel for receiving or conveying vapor/cooling fluid/etc. for blade (242, 342). It may also be desirable to still provide some flexibility in sleeve (260, 360), to prevent blade (242, 342) from generating excess heat in the event that a non-nodal portion of blade (242, 342) engages sleeve (260, 360). Thus, it may be desirable to balance the physical properties of the sleeve between rigid and flexible. Several examples of blade sleeves (1160, 1260, 1360, 1460, 1560, 1660) are disclosed below that include features to increase stiffness yet maintain a desired level of flexibility. While blade sleeves (1160, 1260, 1360, 1460, 1560, 1660) may be described within the context of an instrument similar to instrument (10) or instrument (100), it should be understood that the various features described below may be readily incorporated into any instrument described herein as will be apparent to those of ordinary skill in the art in view of the teachings herein.

1. Exemplary Multiple Layered Blade Sleeve

Figure 18:
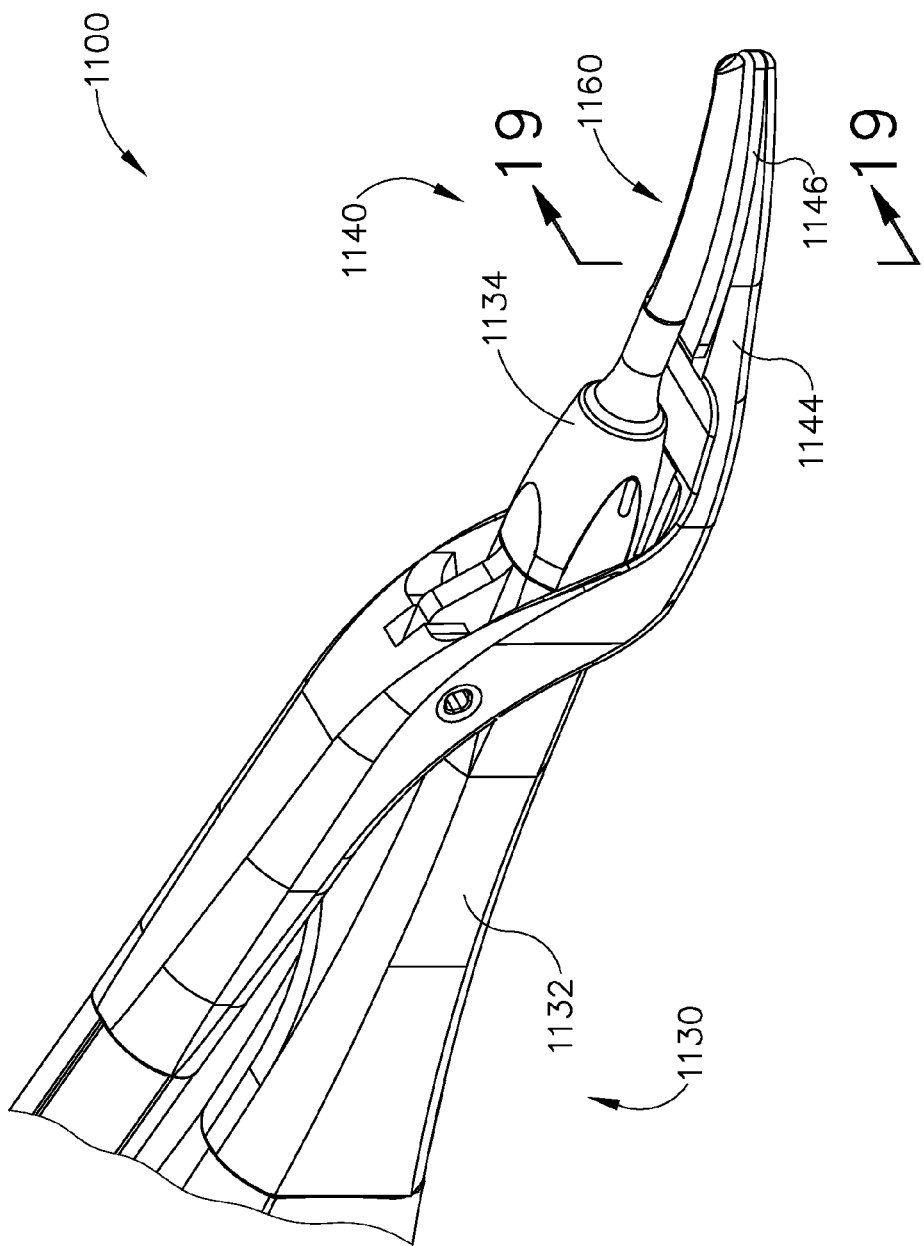
FIG. 18 depicts a detailed perspective view of an end effector of another exemplary alternative instrument that includes a multi-layered blade sleeve.
Figure 19:
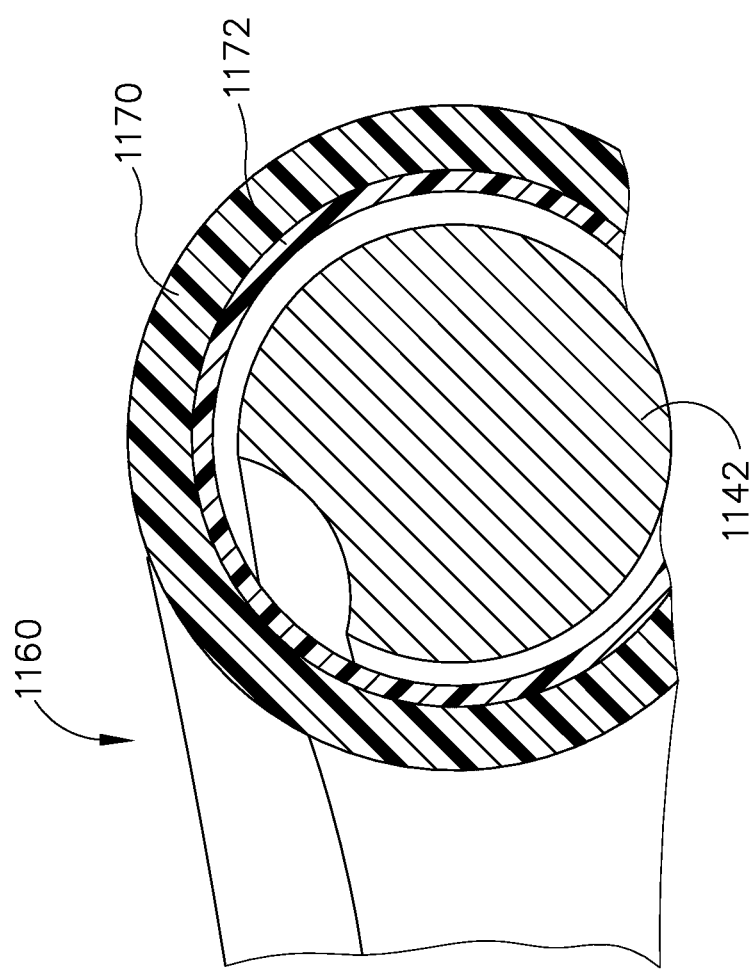
FIG. 19 depicts a cross-sectional perspective view of the end effector of FIG. 18, the cross-section taken along line 19-19 of FIG. 18.

FIGS. 18 and 19 show an exemplary alternative instrument (1100), which incorporates a blade sleeve (1160) having a stiffening layer (1170) and an inner layer (1172). Instrument (1100) is substantially similar to instrument (100) described above except as otherwise noted below. In particular, instrument (1100) comprises a shaft assembly (1130) and an end effector (1140). Shaft assembly (1130) comprises an outer sheath (1132) and a cap (1134) attached to outer sheath (1132). Sleeve (1160) extends distally from cap (1134). End effector (1140) comprises an ultrasonic blade (1142) and a clamp arm (1144), which is pivotable relative to blade (1142) to clamp tissue between a clamp pad (1146) of clamp arm (1144) and blade (1142).

Blade sleeve (1160) is substantially similar to blade sleeves (260, 360) described above such that sleeve (1160) corresponds generally to the size and shape of blade (1142) to cover the outer portion of blade (1142). As can best be seen in FIG. 19 and as noted above, sleeve (1160) comprises two layers, an outer stiffening layer (1170) and an inner layer (1172). Stiffening layer (1170) may be comprised of a rigid material such as a rigid plastic, metal, ceramic, or the like. In contrast, inner layer (1172) may be comprised of a relatively soft and thermal insulating material such as silicone, polytetrafluoroethylene, or the like. In addition, inner layer (1172) may be coated to the interior of stiffening layer (1170) to form a coating. By way of example only, stiffening layer (1170) may comprise steel while inner layer (1172) may comprise silicone, with the steel being dip-coated in the silicone. In some other examples, inner layer (1172) may be attached with an adhesive or mechanical attachment means. As yet another merely illustrative example, inner layer (1172) may be overmolded on stiffening layer (1170). In an exemplary mode of operation, stiffening layer (1170) is operable to provide structural stiffness to sleeve (1160) such that sleeve (1160) remains in position relative to blade (1142). However, in the event that inner layer (1172) contacts blade (1142) while blade (1142) is ultrasonically activated, inner layer (1172) does not damage blade (1172). Sleeve (1160) will also act as a heat shield to prevent inadvertent direct contact between tissue and blade (1142). Sleeve (1160) may also gather vapor generated when tissue is heated by blade (1142) and thus cool blade (1142) with the gathered vapor. In addition or in the alternative, sleeve (1160) may convey a cooling liquid to blade (1142) as described in one or more references cited herein.

Figure 20:
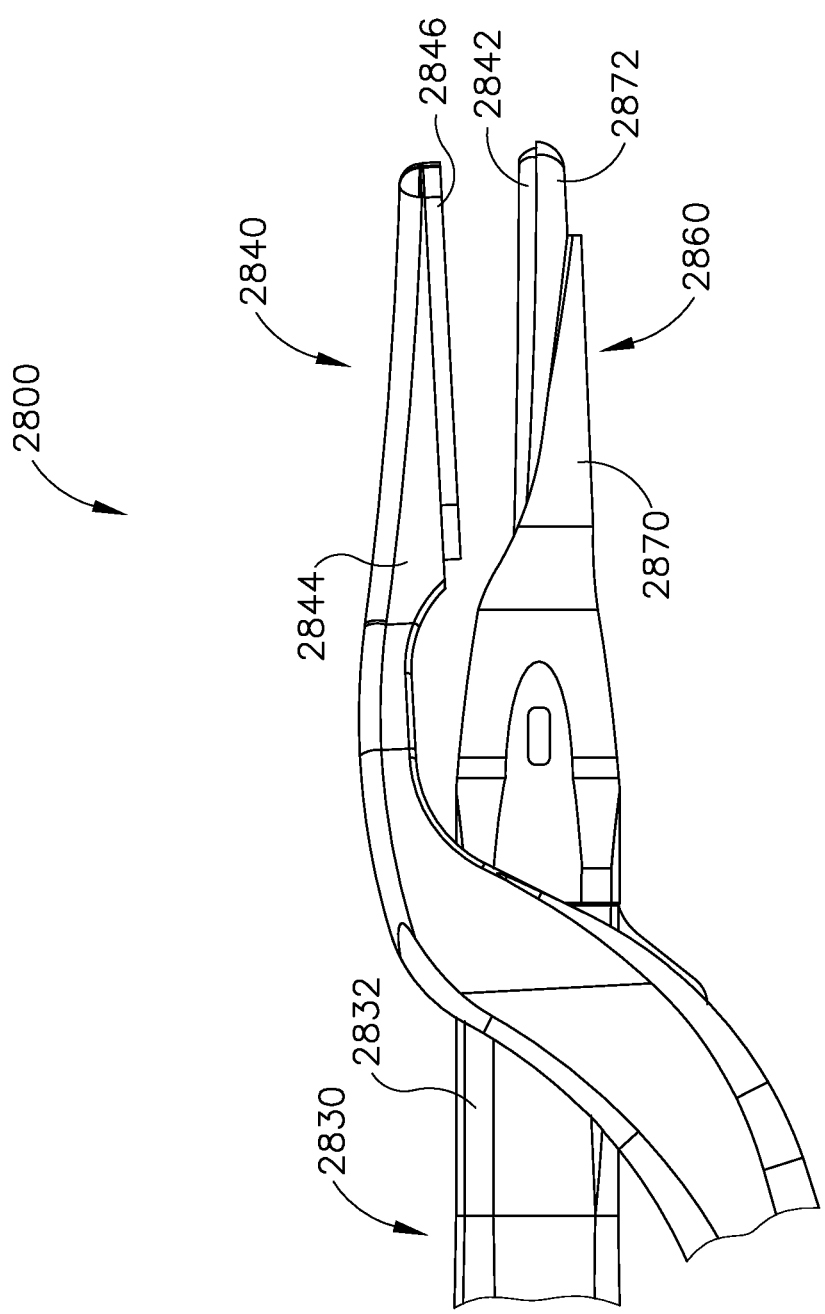
FIG. 20 depicts a side elevational view of an end effector of another exemplary alternative instrument that includes a multi-layered blade sleeve.

FIG. 20 shows another alternative instrument (2800), which incorporates a blade sleeve (2860) having a stiffening layer (2870) and an inner layer (2872). Instrument (2800) is substantially similar to instrument (1100) described above except as otherwise noted below. In particular, instrument (2800) comprises a shaft assembly (2830) and an end effector (2840). Shaft assembly (2830) comprises an outer sheath (2832) and a cap (2834) attached to outer sheath (2832). Sleeve (2860) extends distally from cap (2834). End effector (2840) comprises an ultrasonic blade (2842) and a clamp arm (2844), which is pivotable relative to blade (2842) to clamp tissue between a clamp pad (2846) of clamp arm (2844) and blade (2842).

As noted above, blade sleeve (2860) comprises stiffening layer (2870) and inner layer (2872). Like stiffening layer (1170) described above, stiffening layer (2870) comprises a rigid material such as rigid plastic, metal, ceramic, or etc. such that stiffening layer (2870) adds increased stiffness to sleeve (2860). However, unlike stiffening layer (1170), stiffening layer (2870) does not extend for the full length of blade (2842). Instead, inner layer (2872) extends distally beyond stiffening layer (2870) for the full length of blade (2842). By way of example only, stiffening layer (2870) may terminate 2 to 6 mm proximally from the distal end of blade (2842). Like inner layer (1172) described above, inner layer (2872) is comprised of a flexible material such as silicone or the like. Accordingly, the portion of inner layer (2872) not supported by stiffening layer (2870) may be moveable away from blade (2842). In an exemplary mode of operation, an operator may actuate inner layer (2872) away from blade (2842) using tissue, a feature of end effector (2840), or another instrument. With a portion of blade (2842) fully exposed, a user may use blade (2842) for procedures requiring the entire outer region of blade (2842) (e.g., backcutting). After use, an operator may release inner layer (2872) and inner layer (2872) may return to its original position adjacent to blade (2842) as shown in FIG. 20.

Figure 21:
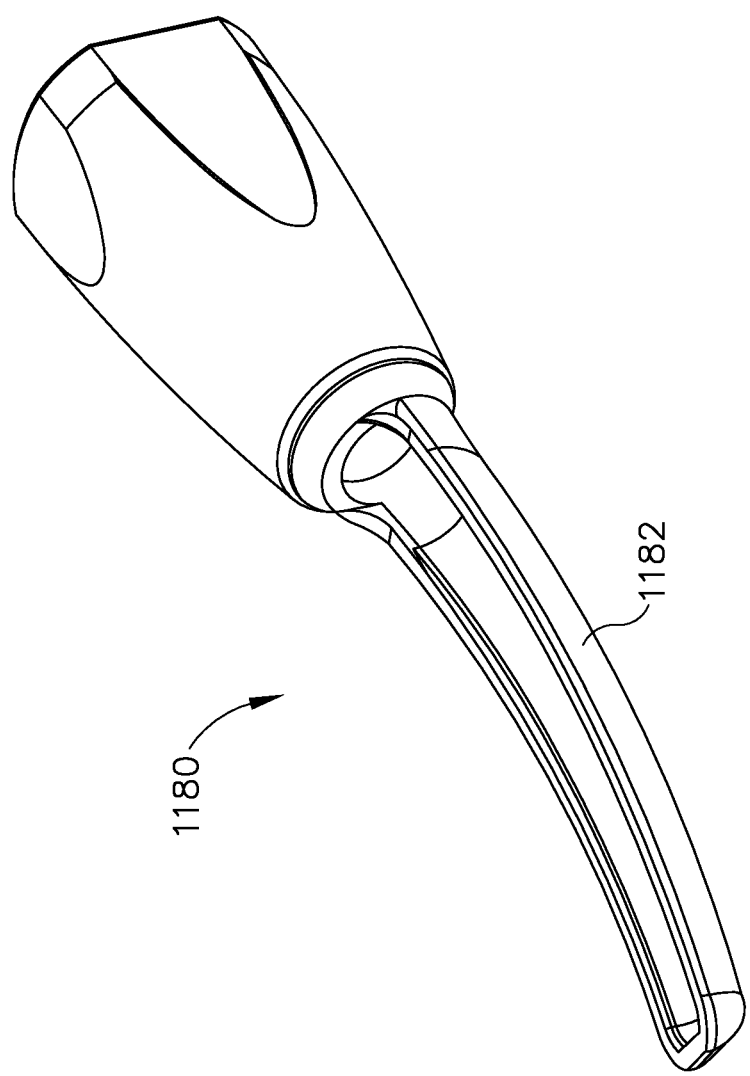
FIG. 21 depicts a perspective view of an exemplary alternative blade sleeve that may be used with the instrument of FIG. 18.

FIG. 21 shows an alternative blade sleeve (1180) that may be used with instrument (1100) as an alternative to blade sleeve (1160). Sleeve (1180) is substantially the same as sleeve (1160) except that sleeve (1180) of this example comprises a single layer (1182). Sleeve (1180) of this example may be comprised of a single material having high stiffness and high temperature properties such as ultem, PEEK, and/or any other suitable material(s). In other examples, the interior and/or exterior of sleeve (1180) may be coated with a compliant and high temperature tolerant material such as silicone to reduce wear, noise, and/or inefficiency upon contact with blade (1142).

Figure 22:
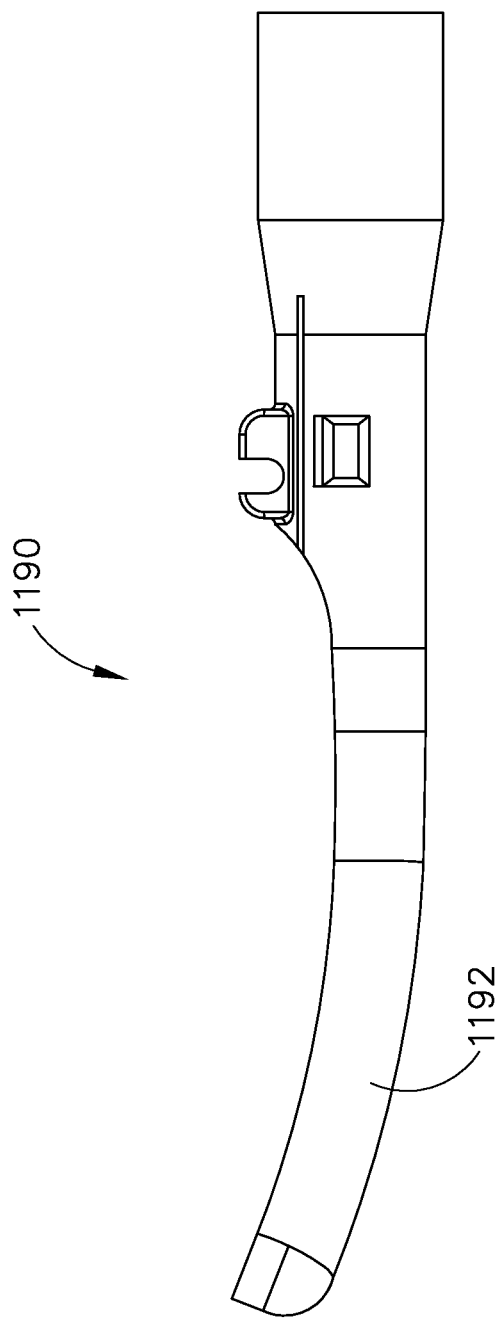
FIG. 22 depicts a side elevational view of an exemplary alternative blade sleeve that may be used with the instrument of FIG. 18.

FIG. 22 shows yet another alternative blade sleeve (1190) that may be used with instrument (1100) in alternative to blade sleeves (1160, 1180). Sleeve (1190) is similar to sleeve (1180). However, sleeve (1190) of this example is comprises resilient material and includes a blade cover (1192) with a slight preformed bend or curve such that blade cover (1192) bends toward the longitudinal axis of blade (1142). In some versions, sleeve (1190) is formed of only a single material. In some other versions, sleeve (1190) is formed of two or more layered materials. By way of example only, sleeve (1190) may comprise an inner layer of silicone (or some other relatively soft material) and an outer layer of resilient plastic (or some other resilient material). The curved shape of blade cover (1192) biases the distal end of blade sleeve (1190) toward blade (1142) when sleeve is installed on instrument (1100). With sleeve (1190) installed onto instrument (1100) blade (1142) may engage the distal end of sleeve (1190) and thereby deflect sleeve (1190), causing sleeve (1190) to assume a configuration that is nearly parallel with the longitudinal axis of blade (1142). It should be understood that the preformed bend of blade cover (1192) acts to keep sleeve (1190) relatively close to blade (1142) when sleeve (1190) is installed about blade (1142).

2. Exemplary Instrument with Integral Blade Sleeve

Figure 23:
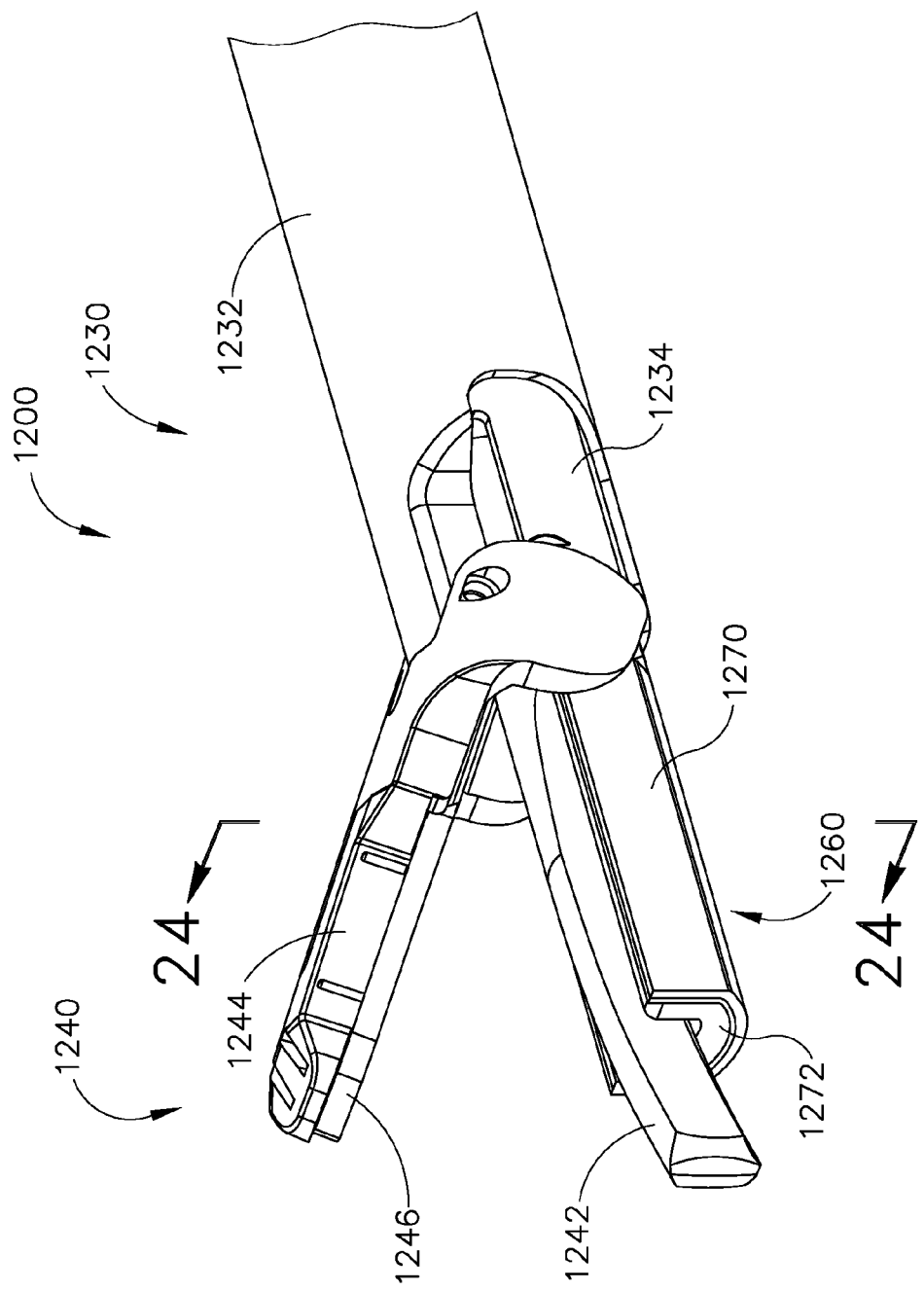
FIG. 23 depicts a detailed perspective view of an end effector of another exemplary alternative instrument that includes an integral blade sleeve.
Figure 24:
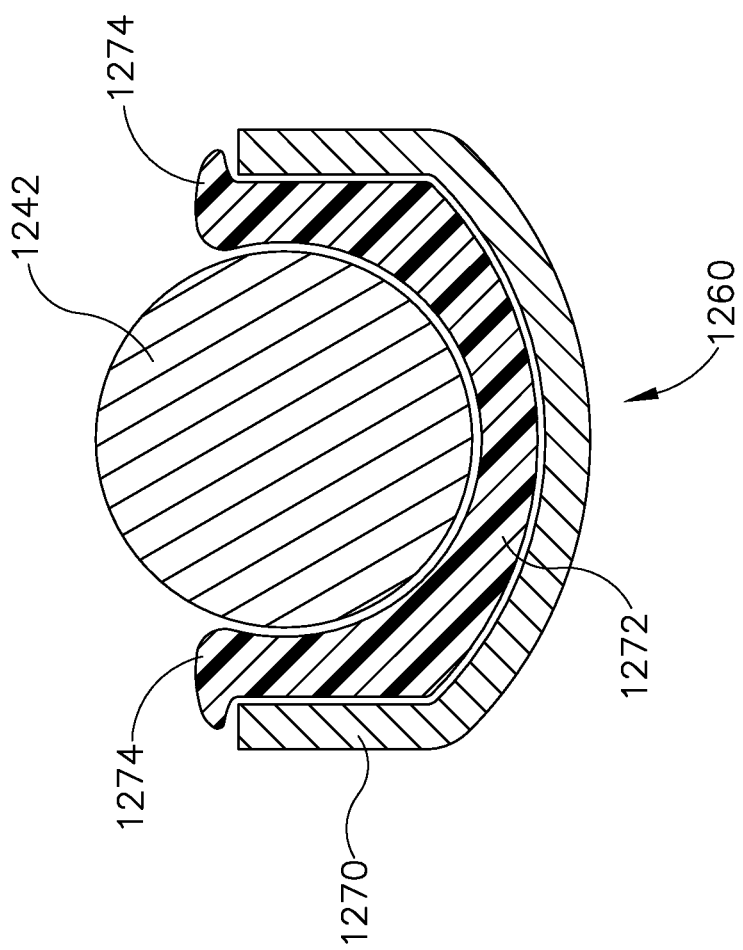
FIG. 24 depicts a side cross-sectional view of the end effector of FIG. 23, the cross-section taken along line 24-24 of FIG. 23.

FIGS. 23 and 24 show an exemplary alternative instrument (1200), which incorporates an integral blade sleeve (1260). Instrument (1200) is substantially similar to instrument (10) described above except as otherwise noted below. In particular, instrument (1200) comprises a shaft assembly (1230) and an end effector (1240). Shaft assembly (1230) comprises an outer sheath (1232) and an inner tube (1234) oriented coaxially within outer sheath (1232). Sleeve (1260) extends distally from inner tube (1234), as will be described in greater detail below. End effector (1240) comprises an ultrasonic blade (1242) and a clamp arm (1244), which is pivotable relative to blade (1242) to clamp tissue between a clamp pad (1246) of clamp arm (1244) and blade (1242).

Sleeve (1260) is similar to sleeve (1160) described above, in that sleeve (1260) comprises a supporting outer layer (1270) and an inner layer (1272). However, unlike sleeve (1160), sleeve (1260) extends for only a portion of the length of blade (1242). Moreover, sleeve (1260) is of integral construction with inner tube (1234) such that outer layer (1270) is essentially a unitary extension of inner tube (1234). Accordingly, outer layer (1270) comprises the same structural material as inner tube (1234) (e.g., metal, ceramic, etc.). Although outer layer (1270) is shown as being integral with inner tube (1234) in this example, it should be understood that in other examples outer layer (1270) may alternatively be integral with outer sheath (1232). Inner layer (1272) comprises a softer material such as silicone, polytetrafluoroethylene, and or the like. Additionally, inner layer (1272) includes outwardly extending portions (1274), which cover the edges of outer layer (1270) to further prevent contact between blade (1242) and outer layer (1270). Outwardly extending portions (1274) may also prevent tissue from contacting the edges of outer layer (1270). In an exemplary mode of operation, stiffening layer (1270) provides structural stiffness to sleeve (1260) such that sleeve (1260) remains in position relative to blade (1242). However, inner layer (1272) is operable to contact blade (1272) without damaging blade (1272), while still serving as a heat shield and/or a feature for proving cooling fluid to blade (1272).

3. Exemplary Instrument with Blade Sleeve Stiffening Member

Figure 25:
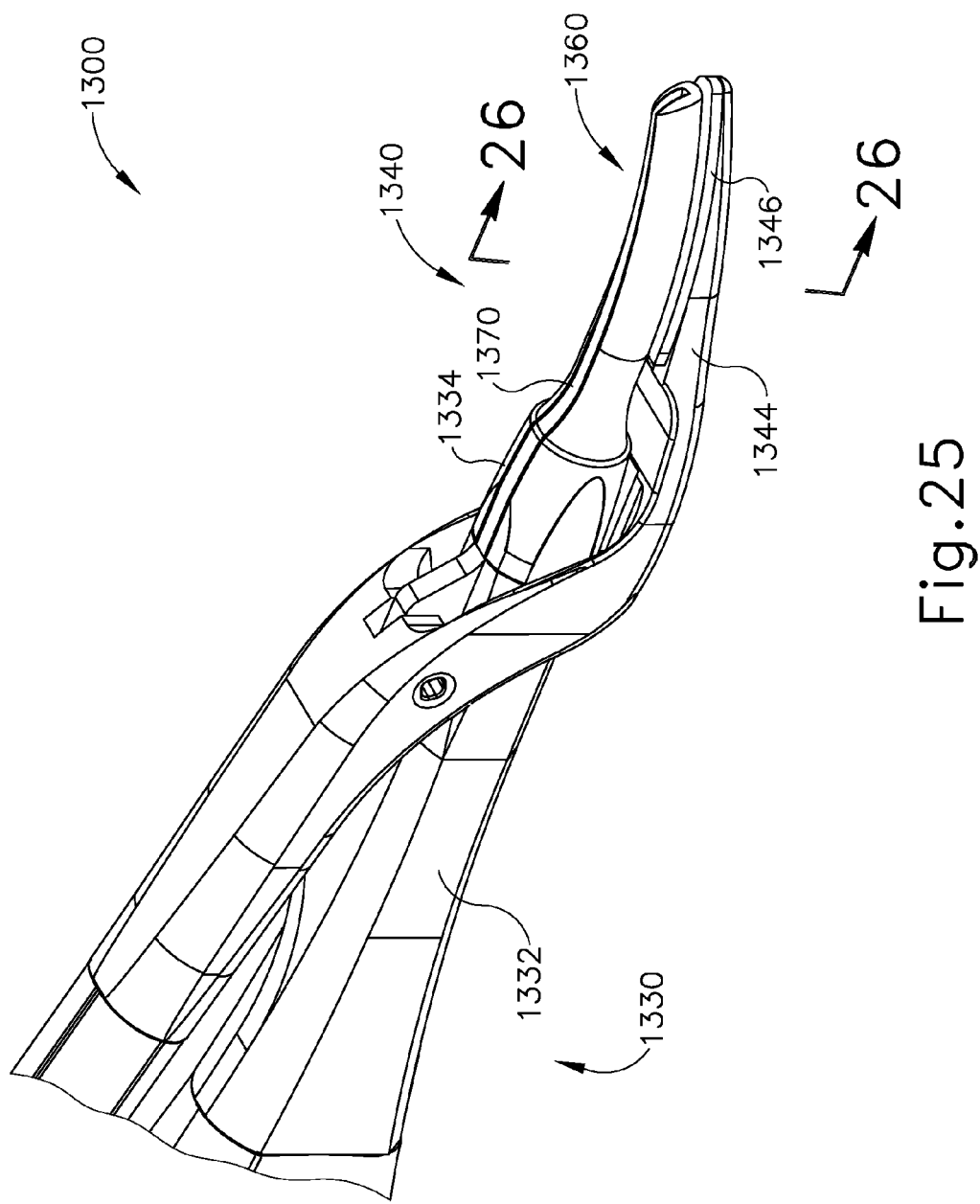
FIG. 25 depicts a detailed perspective view of an end effector of another exemplary alternative instrument that includes a blade sleeve having a stiffening member.
Figure 26:
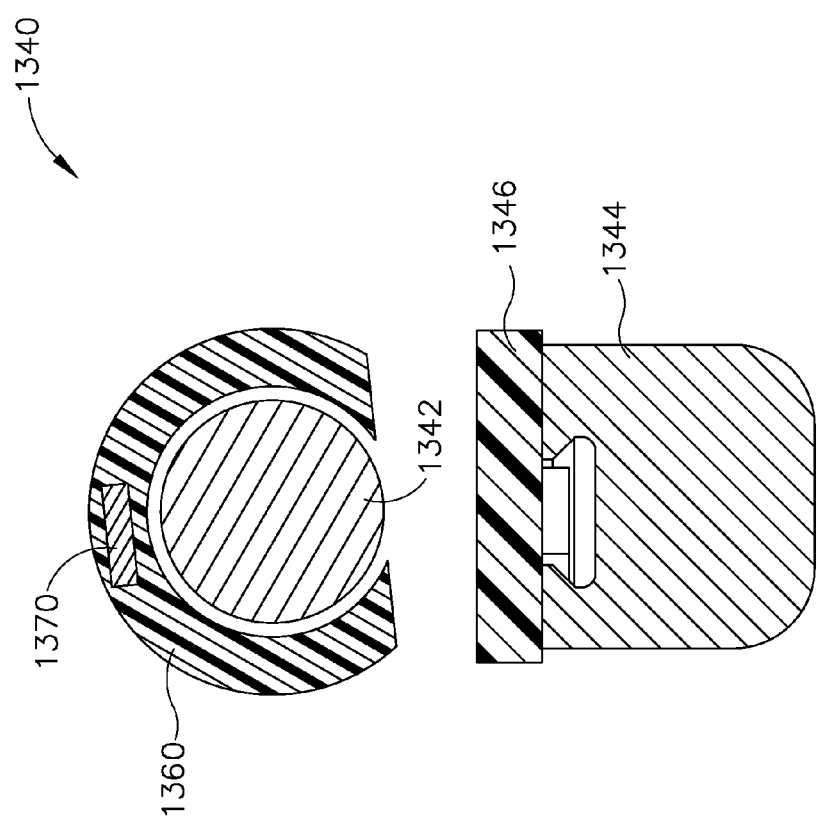
FIG. 26 depicts a cross-sectional end view of the end effector of FIG. 25, the cross-section taken along line 26-26 of FIG. 25.
Figure 27:
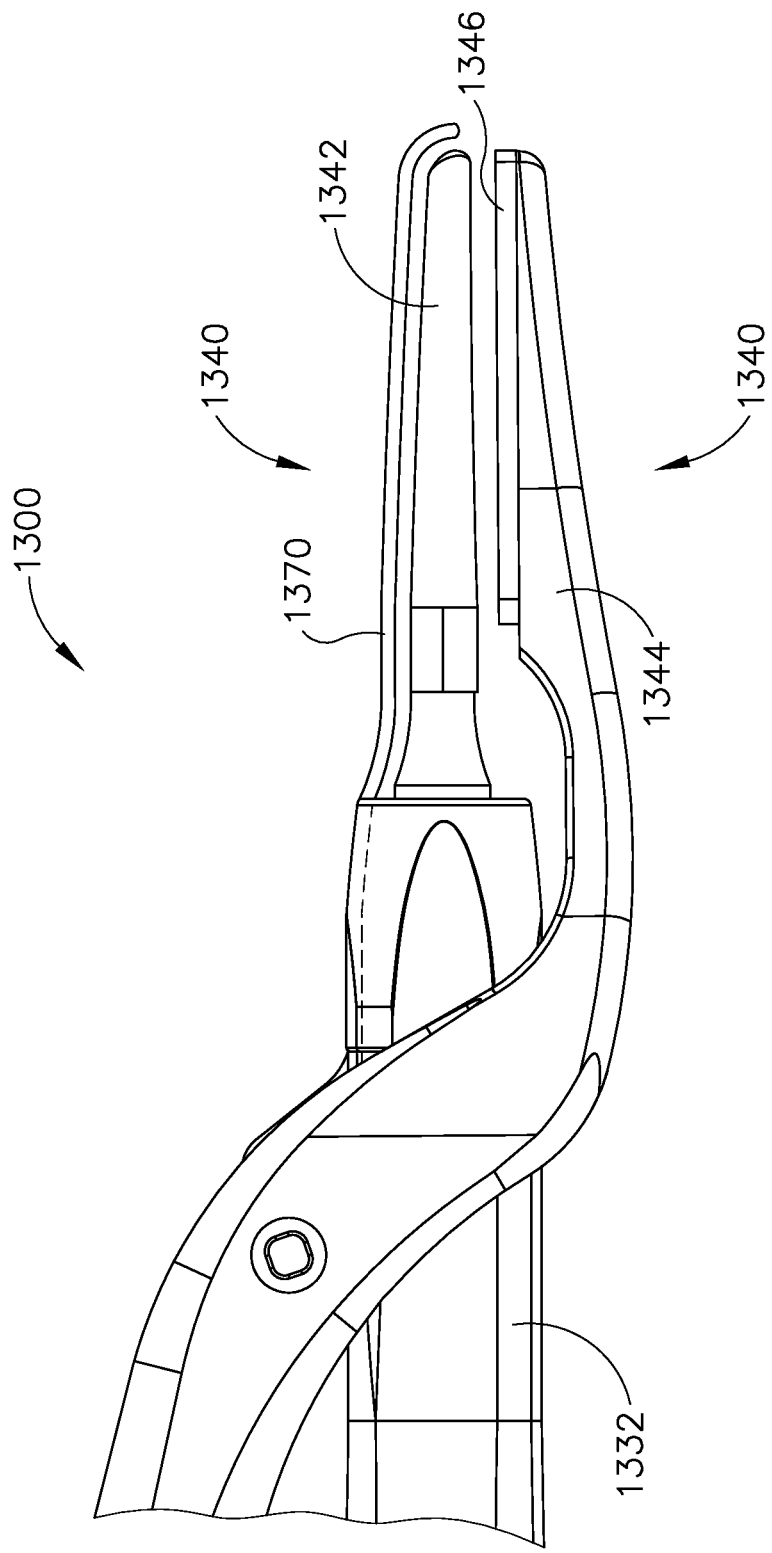
FIG. 27 depicts a side elevational view of the end effector of FIG. 25 with the blade sleeve removed.

FIGS. 25-27 show an exemplary alternative instrument (1300), which includes a stiffening member (1370) to stiffen a blade sleeve (1360). Instrument (1300) is substantially similar to instrument (100) described above except as otherwise noted below. In particular, instrument (1300) comprises a shaft assembly (1330) and an end effector (1340).

Shaft assembly (1330) comprises an outer sheath (1332) and a cap (1334) attached to outer sheath (1332). Sleeve (1360) extends distally from cap (1334). End effector (1340) comprises an ultrasonic blade (1342) and a clamp arm (1344), which is pivotable relative to blade (1342) to clamp tissue between a clamp pad (1346) of clamp arm (1344) and blade (1342).

Instrument (1300) further includes a stiffening member (1370). Stiffening member (1370) extends distally from outer sheath (1332) through cap (1334) and through sleeve (1360) opposite to blade (1342). The proximal end of stiffening member (1370) may be secured to outer sheath (1332) by welding, mechanical fastening means, adhesive boding, and/or in any other suitable fashion. In the present example, stiffening member (1370) is comprised of a relatively rigid material such as metal, rigid plastic, or the like. Stiffening member (1370) may be formed as a substantially straight rod, beam, or similar structure.

Sleeve (1360) is substantially similar to sleeves (260, 360) described above. However, as can be seen in FIG. 26, sleeve (1360) may be overmolded around stiffening member (1370) (or may be otherwise coupled with stiffening member (1370)) such that sleeve (1360) receives additional structural support from stiffening member (1370). Moreover, because sleeve (1360) is overmolded around stiffening member (1370) (or stiffening member is otherwise disposed within the sidewall of sleeve (1360)), only sleeve (1360) may contact blade (1342). Thus, sleeve (1360) protects blade (1342) from contact with stiffening member (1370).

4. Exemplary Blade Sleeve with Deflection Feature

Figure 28A:
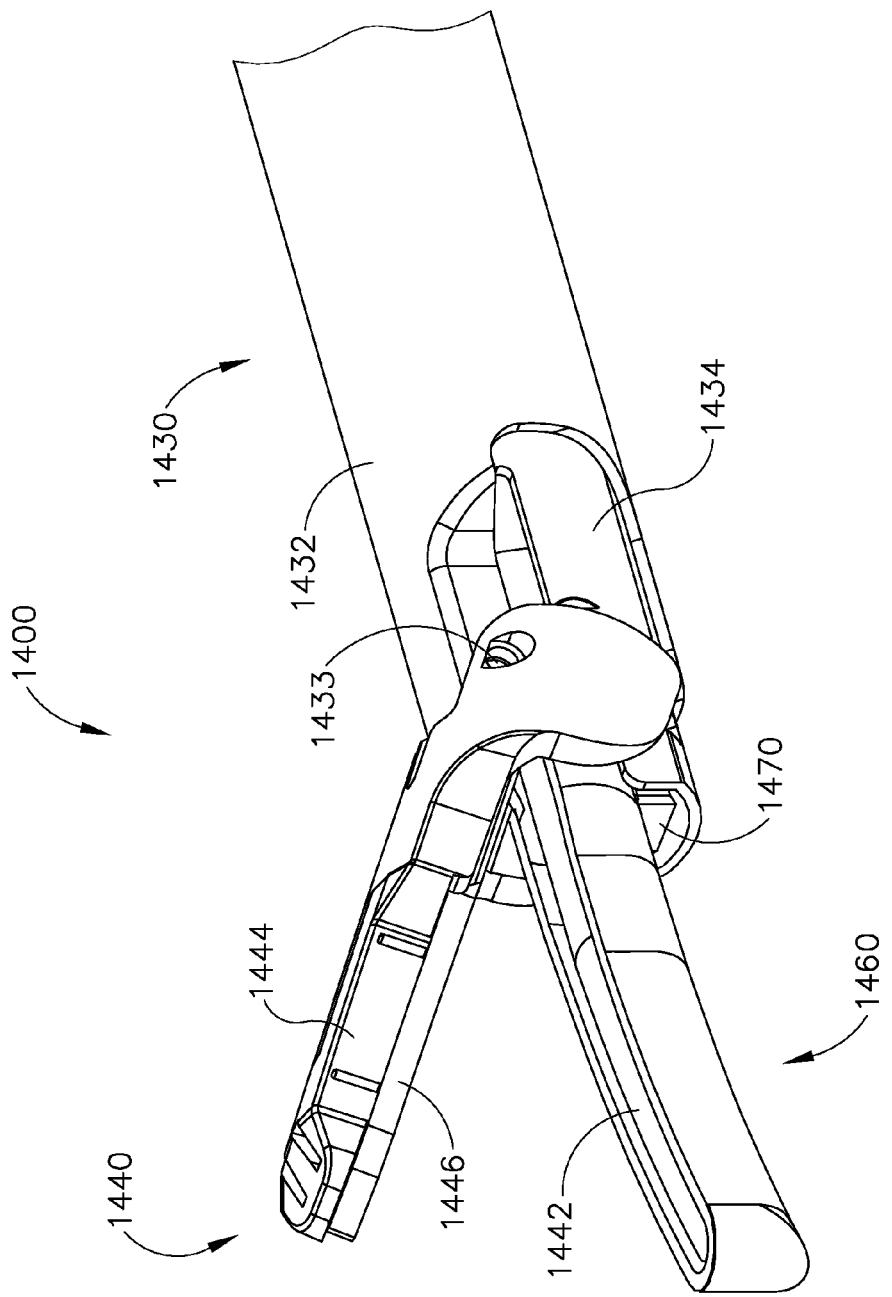
FIG. 28A depicts a detailed perspective view of an end effector of another exemplary alternative instrument that includes a blade sleeve having a deflection feature, with the blade sleeve deflected upwardly.
Figure 29:
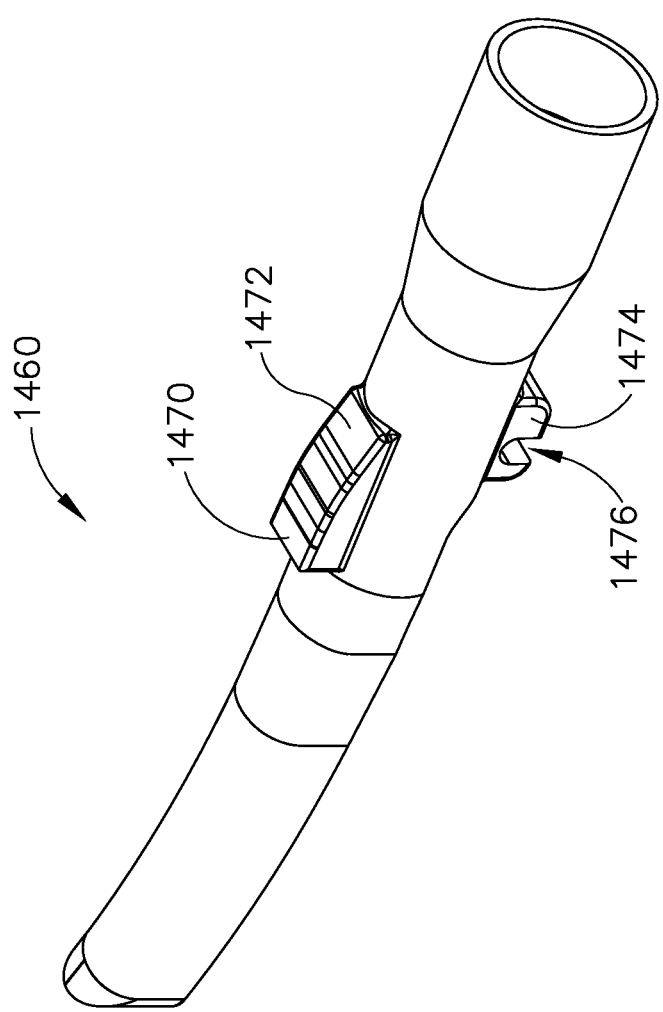
FIG. 29 depicts a detailed perspective view of the blade sleeve of FIG. 28A.

FIGS. 28A-29 show an exemplary alternative instrument (1400), which includes a blade sleeve (1460) having an integral deflection feature (1470). Instrument (1400) is substantially similar to instrument (10) described above except as otherwise noted below. In particular, instrument (1400) comprises a shaft assembly (1430) and an end effector (1440). Shaft assembly (1430) comprises an outer sheath (1432) and an inner tube (1434) oriented coaxially within outer sheath (1432). Sleeve (1460) extends distally from inner tube (1434), as will be described in greater detail below. End effector (1440) comprises an ultrasonic blade (1442) and a clamp arm (1444), which is pivotable relative to blade (1442) to clamp tissue between a clamp pad (1446) of clamp arm (1444) and blade (1442).

Sleeve (1460) includes an integral deflection feature (1470), which extends transversely from sleeve (1460). Deflection feature (1470) includes a tapered portion (1472) that tapers toward the proximal end of deflection feature (1470). Thus, deflection feature (1470) is thicker at its distal end and thinner at its proximal end. Sleeve (1460) further includes an attachment feature (1474), which is configured to maintain sleeve (1460) at a fixed longitudinal position relative to blade (1442) while permitting sleeve (1460) to move upwardly and downwardly relative to blade (1442). In particular, attachment feature (1474) comprises a recess (1476) that is configured to receive a pin (1433). Pin (1433) extends through outer sheath (1432), clamp arm (1444), and recess (1476), thus acting as a pivot point for clamp arm (1444) and a point of fixation for recess (1476). However, because recess (1476) is open, attachment feature (1474) is only prevented from moving in the longitudinal direction.

In an exemplary mode of operation (as best seen by comparing FIGS. 28A and 28B), inner tube (1434) is advanced distally to drive clamp arm (1444) away from blade (1442), placing end effector (1440) in an open configuration. When inner tube (1434) is advanced distally, inner tube (1434) acts upon deflection feature (1470) to push sleeve (1460) transversely and into contact with blade (1442). Thus, while end effector (1440) is open, sleeve (1460) is in contact with blade (1442) via deflection member (1470). This may correspond to blade (1442) being inactive such that sleeve (1460) may dissipate excess heat without being subjected to vibrational energy from blade (1442).

To drive clamp arm (1444) toward blade (1442) and thereby close end effector (1440), inner tube (1434) is retracted proximally. As inner tube (1434) is retracted proximally, inner tube (1434) moves along tapered portion (1472) of deflection member (1470). As inner tube (1434) moves along tapered portion (1472), deflection member (1470) clears the distal end of inner tube (1434) and thereby permits sleeve (1460) to move transversely away from blade (1442) in the direction indicated by the arrow (1480) in FIG. 28B. Thus, when end effector (1440) is in a closed configuration, sleeve (1460) may disengage from blade (1442). In some versions, sleeve (1460) is preformed to resiliently deflect transversely away from blade (1442) when the distal end of inner tube (1434) is not bearing against deflection member (1470). In addition or in the alternative, sleeve (1460) may be pushed to deflect transversely away from blade (1442) by tissue that is being compressed against blade (1442) by clamp arm (1444). In any of these cases, with sleeve (1460) at least partially disengaged from blade (1442), blade (1142) may be ultrasonically activated to cut and sever tissue without having an adverse impact on sleeve (1460).

It should be understood that although deflection member (1470) is shown as being a part of sleeve (1460), in other examples deflection member (1470) may comprise one or more mechanical design features generally tied to the opening and/or closing of end effector (1440). For instance, in some examples, clamp arm (1444) may incorporate a mechanical feature to drive sleeve (1460) toward and/or away from blade (1442) in response to movement of clamp arm (1444). Yet in other examples, inner tube (1434) may comprise a member similar to deflection member (1470) that may drive sleeve (1460) toward and/or away from blade (1442) in response to movement of clamp arm (1444).

C. Exemplary Ultrasonic Blades with Overmolded Blade Covers

In some instances it may be desirable to use an instrument similar to instruments (10, 100) described above without a blade sleeve similar to blade sleeves (260, 360, 460, 560, 660, 760, 860, 960, 1060, 1160, 1260, 1360, 1460) described above. Even without the blade sleeve, it may still be desirable to protect at least a portion of an ultrasonic blade from inadvertent contact with tissue and/or to efficiently dissipate heat from the ultrasonic blade. In such instances, similar desirable characteristics may be achieved using a cover that is directly overmolded onto an ultrasonic blade, thus eliminating the need for a separately secured blade sleeve. While the following examples include covers that are overmolded onto ultrasonic blades, it should be understood that other portions of an end effector may include one or more overmolded covers, in addition to or in lieu of an overmold on the ultrasonic blade. By way of example only, a clamp arm may include one or more overmolded covers. An overmolded cover on a clamp arm (and/or elsewhere on the end effector) may be provided in accordance with the teachings below and/or in any other suitable fashion. Numerous other variations of overmolded covers will be apparent to those of ordinary skill in the art in view of the teachings herein.

Figure 30:
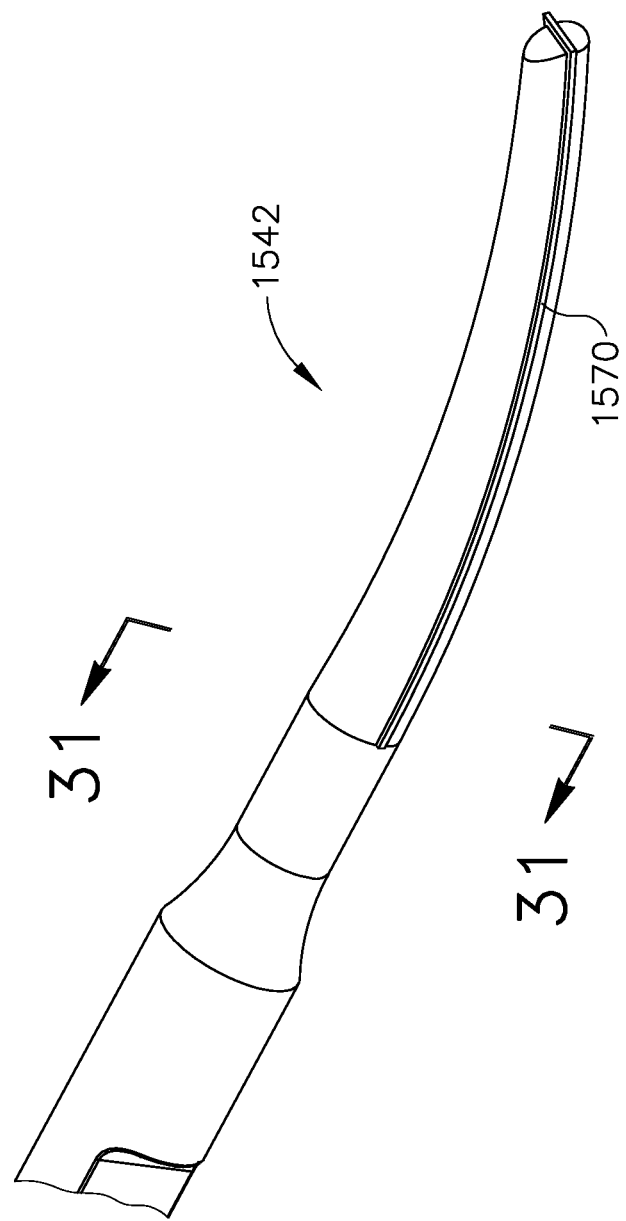
FIG. 30 depicts a detailed perspective view of an exemplary alternative ultrasonic blade having an attachment protrusion.
Figure 31:
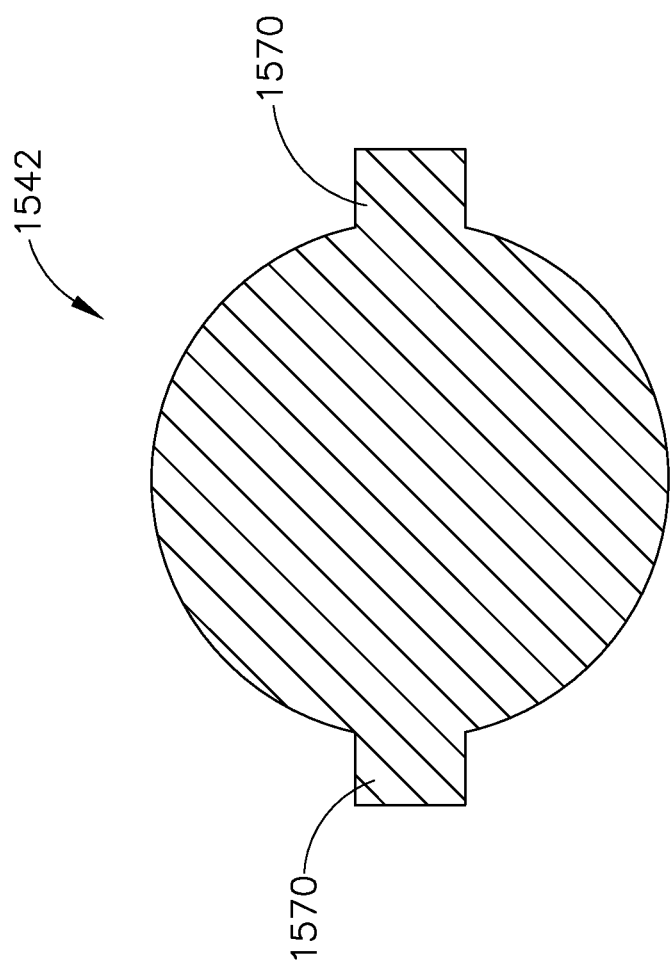
FIG. 31 depicts a cross-sectional end view of the ultrasonic blade of FIG. 30, the cross-section taken along line 31-31 of FIG. 30.
Figure 32:
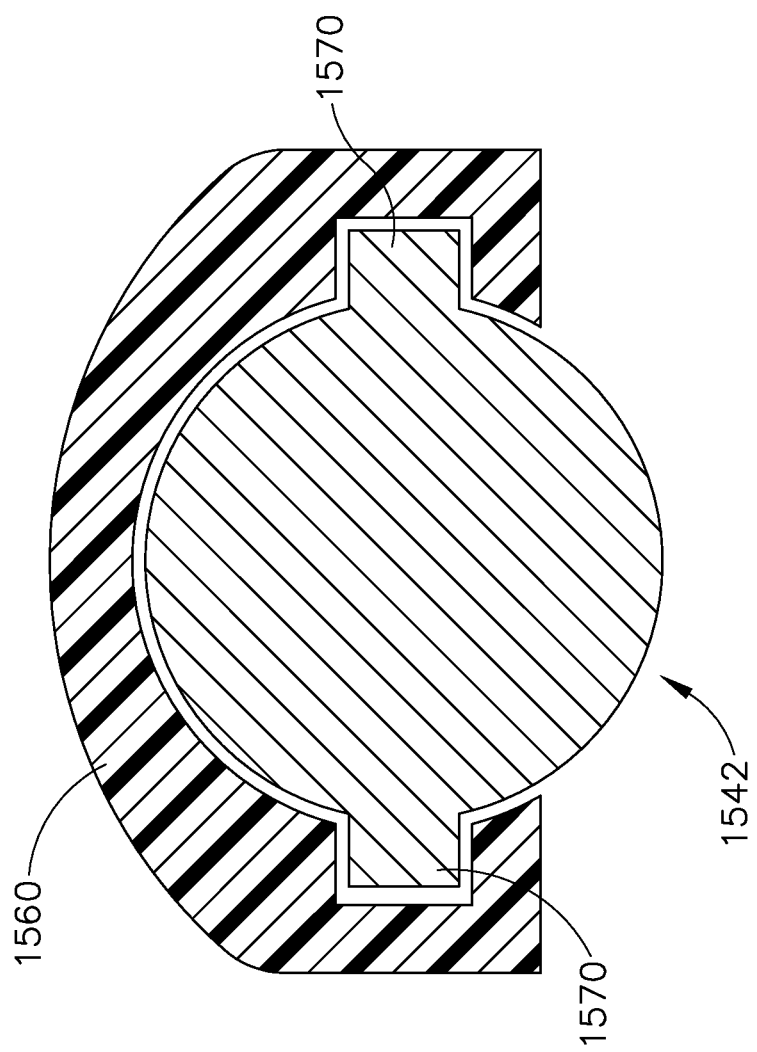
FIG. 32 depicts another cross-sectional end view of the ultrasonic blade of FIG. 30, with an overmold overmolded onto the ultrasonic blade.

FIGS. 30-32 show an exemplary alternative ultrasonic blade (1542) that may be readily incorporated into an instrument similar to instruments (10, 100) described above. Bade (1542) is substantially the same as blades (42, 142) described above, except blade (1542) of this example includes an attachment protrusion (1570) extending around the perimeter of blade (1542). Attachment protrusion (1570) of the present example extends distally along the longitudinal length of blade (1542) at the approximate top-to-bottom center of blade (1542). Alternatively, protrusion (1570) may be positioned closer to the top or bottom of blade (1542). Protrusion (1570) also wraps around the distal end of blade (1542) in this example, though this is optional.

As can best be seen in FIG. 31, attachment protrusion (1570) has a generally rectangular profile, although such a shape may be varied in other examples. In the present example, attachment protrusion (1570) is integral with blade (1542) such that blade (1542) and attachment protrusion (1570) are comprised of the same material. In some other examples, attachment protrusion (1570) may be formed separately from blade (1542) and may comprise a different material from blade (1542).

FIG. 32 shows a cross-section of blade (1542) with an overmold (1560) secured to blade (1542). Overmold (1560) is overmolded around blade (1542) and attachment protrusion (1570). A portion of blade (1542) remains uncovered by blade (1542) such that blade (1542) may be used to clamp, seal, and sever tissue. This exposed portion of blade (1542) may face a clamp arm such as clamp arm (144), such that the clamp arm may compress tissue against the exposed portion of blade (1542). Overmold (1560) may be comprised of any material suitable to protect blade (1542) from inadvertent contact with tissue and to dissipate heat. By way of example only, overmold (1560) may be formed of silicone and/or any other suitable material(s). It should be understood that although overmold (1560) is shown as having a certain shape, overmold (1560) may have any other shape suitable to cover blade (1542).

Figure 33:
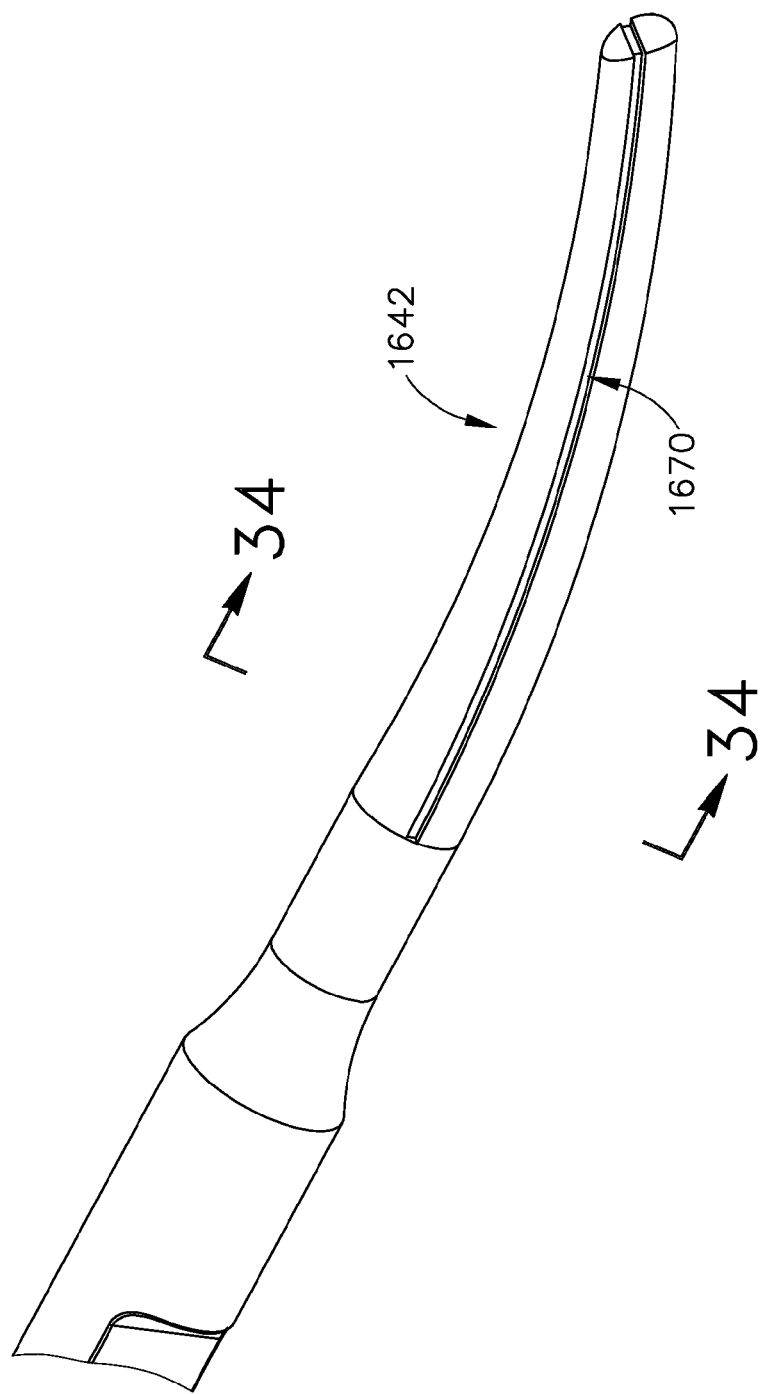
FIG. 33 depicts a detailed perspective view of an exemplary alternative ultrasonic blade having an attachment recess.
Figure 34:
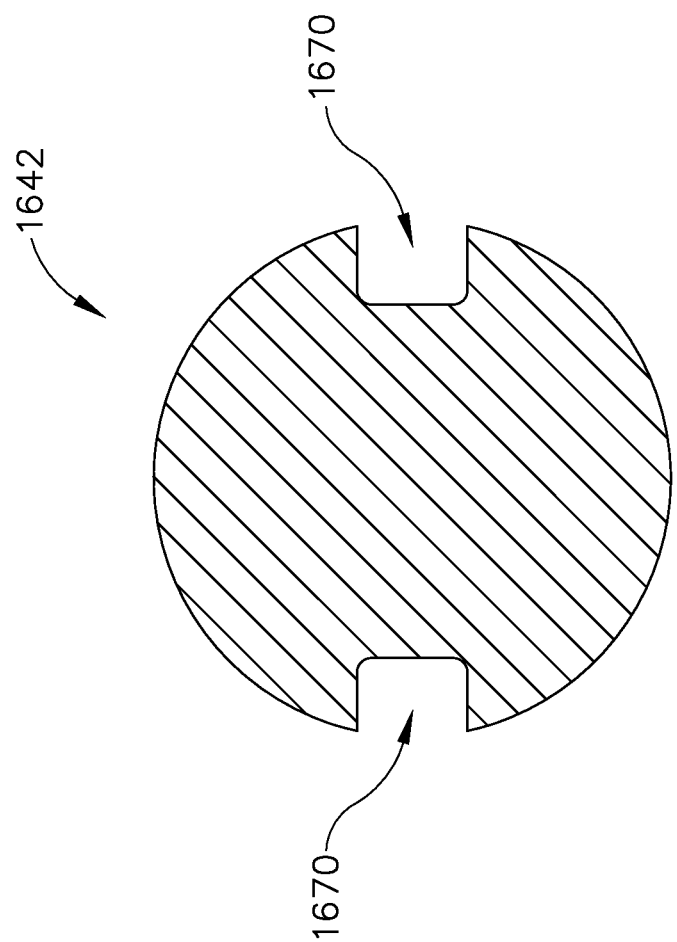
FIG. 34 depicts a cross-sectional end view of the ultrasonic blade of FIG. 33, the cross-section taken along line 34-34 of FIG. 33.
Figure 35:
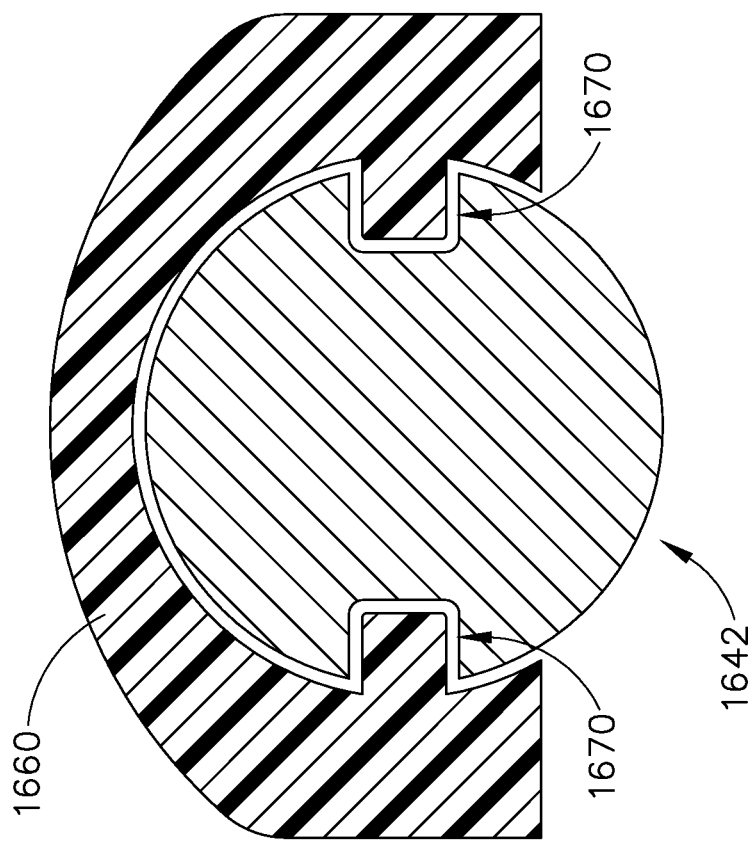
FIG. 35 depicts another cross-sectional end view of the ultrasonic blade of FIG. 33, with an overmold overmolded onto the ultrasonic blade.

FIGS. 33-35 show another alternative ultrasonic blade (1642) that may be readily incorporated into an instrument similar to instruments (10, 100) described above. Blade (1642) is substantially the same as blade (1542) described above, except blade (1642) includes an attachment recess (1670) instead of an attachment protrusion (1570). Attachment recess (1670), like attachment protrusion (1570), extends along the perimeter of blade (1642) longitudinally and wraps around the distal end of blade (1642). As can be seen in FIG. 34, attachment recess (1670) has a generally rounded rectangular profile, though it should be understood that alternative recess shapes may be used if desired.

FIG. 35 shows a cross-section of blade (1642) with an overmold (1660) secured to blade (1642). Overmold (1660) is overmolded around blade (1642) and attachment recess (1670). Like with overmold (1542) described above, a portion of blade (1642) remains uncovered by blade (1642) such that blade (1642) may be used to clamp, seal, and sever tissue. This exposed portion of blade (1642) may face a clamp arm such as clamp arm (144), such that the clamp arm may compress tissue against the exposed portion of blade (1642). Overmold (1660) may be comprised of any material suitable to protect blade from inadvertent contact with tissue and to dissipate heat. By way of example only, overmold (1660) may be formed of silicone and/or any other suitable material(s). It should be understood that although overmold (1660) is shown as having a certain shape, overmold (1660) may have any other shape suitable to cover blade (1642).

Figure 36:
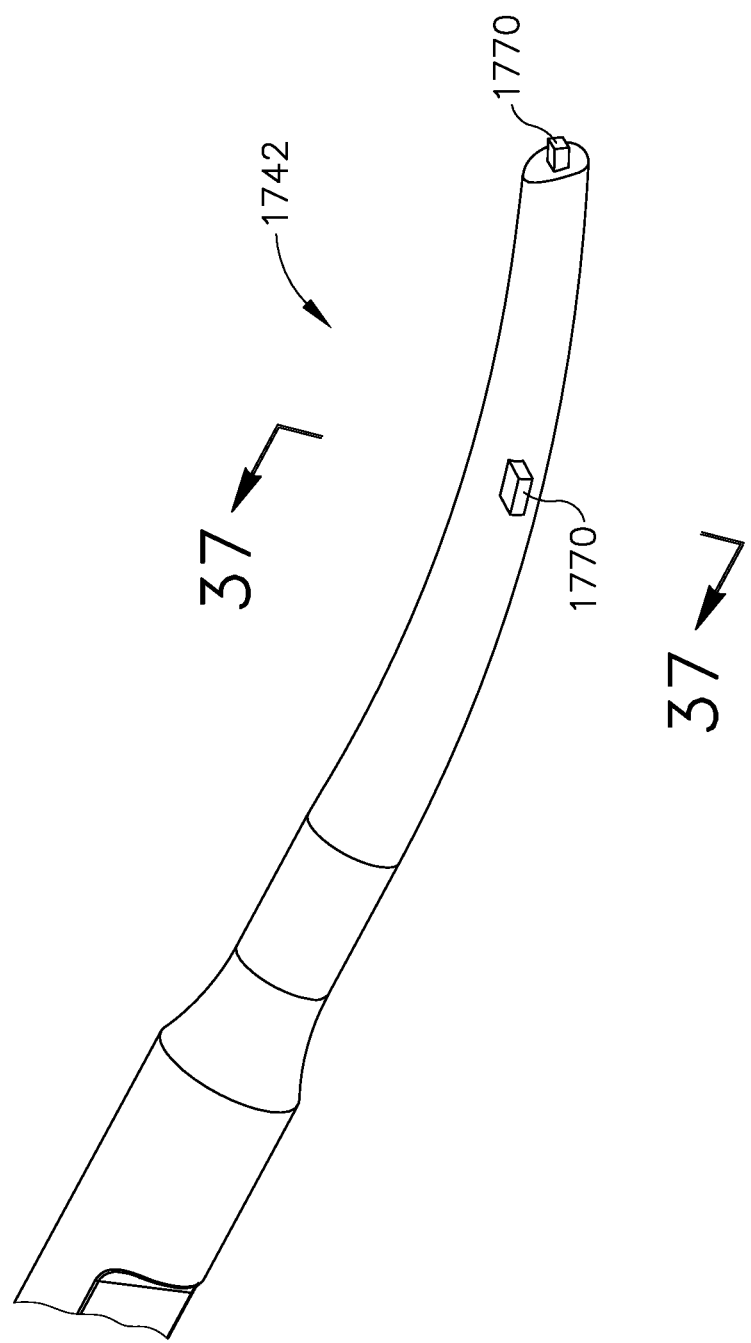
FIG. 36 depicts a detailed perspective view of an exemplary alternative ultrasonic blade having a plurality of discrete attachment protrusions.
Figure 37:
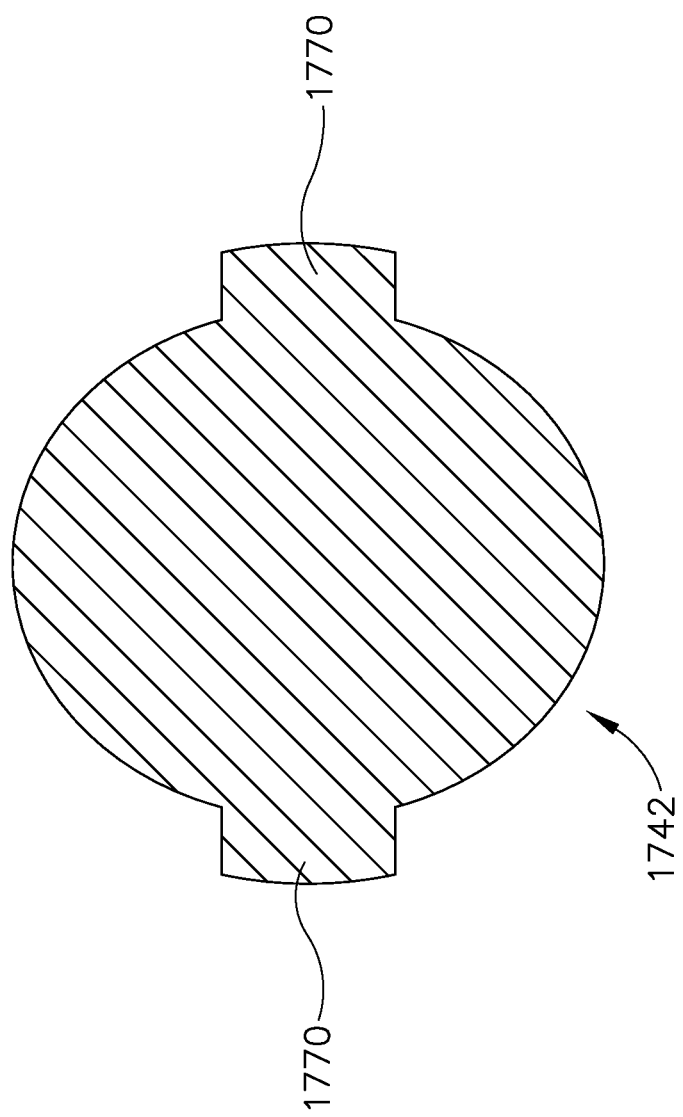
FIG. 37 depicts a cross-sectional end view of the ultrasonic blade of FIG. 36, the cross-section taken along line 37-37 of FIG. 36.
Figure 38:
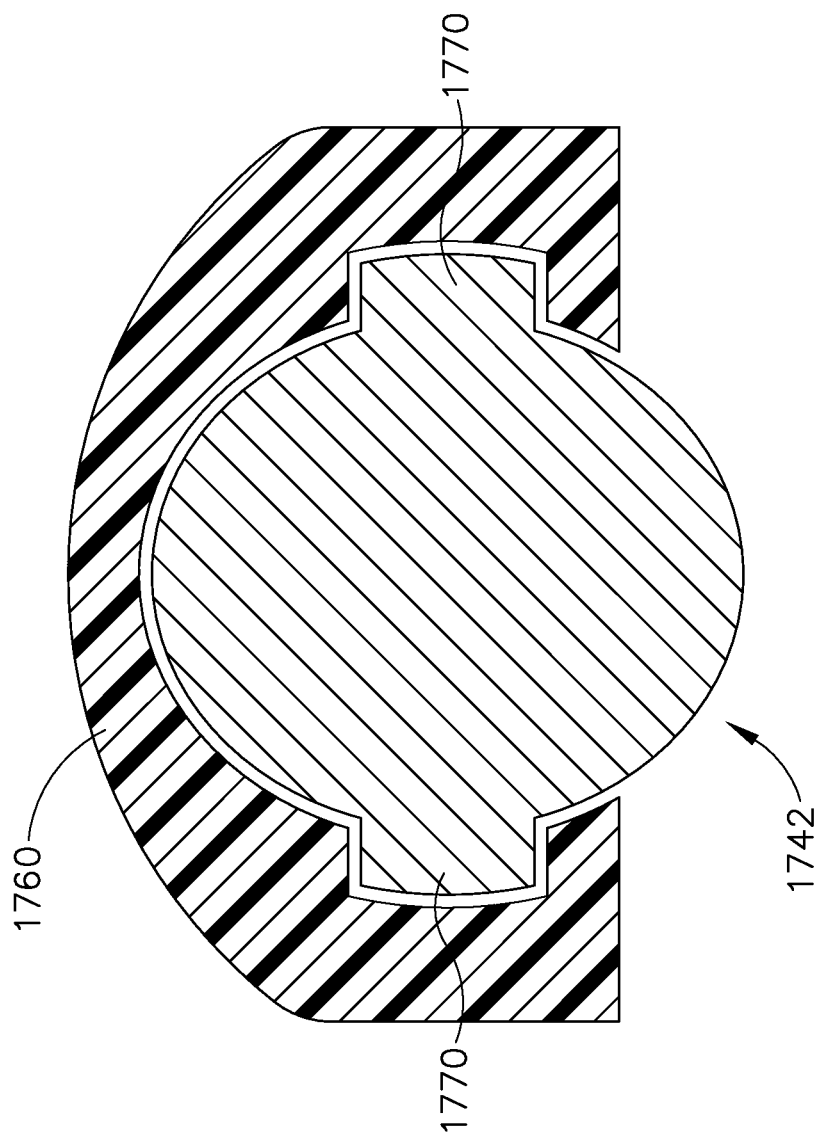
FIG. 38 depicts another cross-sectional end view of the ultrasonic blade of FIG. 36, with an overmold overmolded to the ultrasonic blade.

FIGS. 36-38 show another alternative ultrasonic blade (1742) that may be readily incorporated into an instrument similar to instruments (10, 100) described above. In particular, blade (1742) is substantially the same as blade (1542) described above, except blade (1742) includes a plurality of discrete attachment protrusions (1770) instead of a single continuous attachment protrusion (1570). Attachment protrusions (1770), unlike attachment protrusion (1570), are positioned at various positions along the perimeter of blade (1742). In particular, two attachment protrusions (1770) are positioned on either side of blade (1742) and a single attachment protrusion (1770) is positioned at the distal end of blade (1742). Of course, any other suitable arrangements may be used. As can be seen in FIG. 37, attachment protrusions (1770) have a generally rectangular shape, although alternative shapes may be used in other examples. Additionally, each attachment protrusion (1770) may have a different shape. Although blade (1742) is shown as having three attachment protrusions (1770), it should be understood that in other examples, more or less protrusions (1770) having varying shapes may be used.

FIG. 38 shows a cross-section of blade (1742) with an overmold (1760) attached. Overmold (1760) is overmolded around blade (1742) and attachment protrusions (1770). Like with overmold (1542) described above, a portion of blade (1742) remains uncovered by blade (1742) such that blade may be used to clamp, seal, and sever tissue. Overmold (1760) may be comprised of any material suitable to protect blade (1742) from inadvertent contact with tissue and to dissipate heat. By way of example only, overmold (1560) may be formed of silicone and/or any other suitable material(s). It should be understood that although overmold (1760) is shown as having a certain shape, overmold (1760) may have any other shape suitable to cover blade (1742). In some alternatives, overmold (1760) is formed separately and is then snapped onto blade (1742) instead of being overmolded about blade. Other suitable variations will be apparent to those of ordinary skill in the art in view of the teachings herein.

Figure 39:
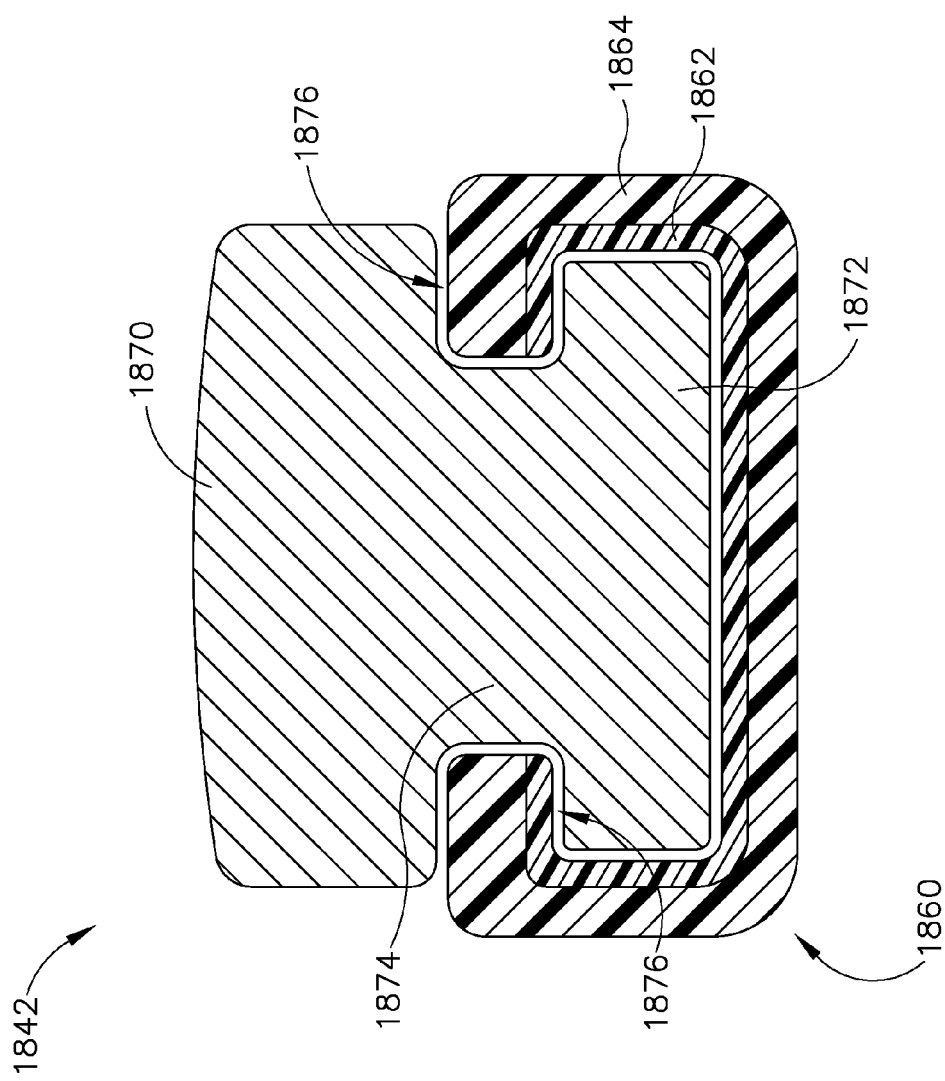
FIG. 39 depicts a cross-sectional end view of an exemplary alternative ultrasonic blade having a I-shaped cross-section for receiving an overmold.

FIG. 39 shows a cross-section of another alternative ultrasonic blade (1842) that may be readily incorporated into an instrument similar to instruments (10, 100) described above. In particular, blade (1842) is substantially similar to blade (1642) described above, except blade (1842) is configured with a different cross sectional geometry. As can be seen, blade (1842) has an I-shaped cross-sectional geometry. With such a geometry, blade (1842) includes a clamping portion (1870) and a cover portion (1872) with each portion (1870, 1872) connected by a recessed connecting portion (1874). As will be understood, clamping portion (1870) may be used for clamping, cutting, and sealing tissue. Connecting portion (1874) is narrower than both clamping portion (1870) and cover portion (1872) such that a recess (1876) is formed on both sides of blade (1842). Recess (1876) also extends along the full length of blade (1842) in this example.

Like attachment recess (1670) described above, recess (1876) of this example may permit blade (1842) to support an overmold (1860). Overmold (1860) is overmolded onto blade (1842) over cover portion (1872) and into recess (1876) over connecting portion (1874). Overmold (1860) of the present example is a two part overmold (1860) comprising a first portion (1862) and a second portion (1864). First portion (1862) and second portion (1864) may be comprised of differing materials to take advantage of differing mechanical properties between first portion (1862) and second portion (1864). For instance, first portion (1862) may comprise a coating on blade (1842) that prevents adhesion of second portion (1864) to blade, while second portion (1864) may comprise a plastic overmold or cap. Yet in other examples, first portion (1862) may comprise a layer of polytetrafluoroethylene or silicone adhered to blade (1842), while second portion (1862) may comprise a ceramic spray coating. Still in other examples, first portion (1862) and second portion (1864) may be substituted with a unitary plastic cap that is shaped to removably fasten to the geometry of blade (1842) (e.g. through a snap fit, etc.).

Figure 40:
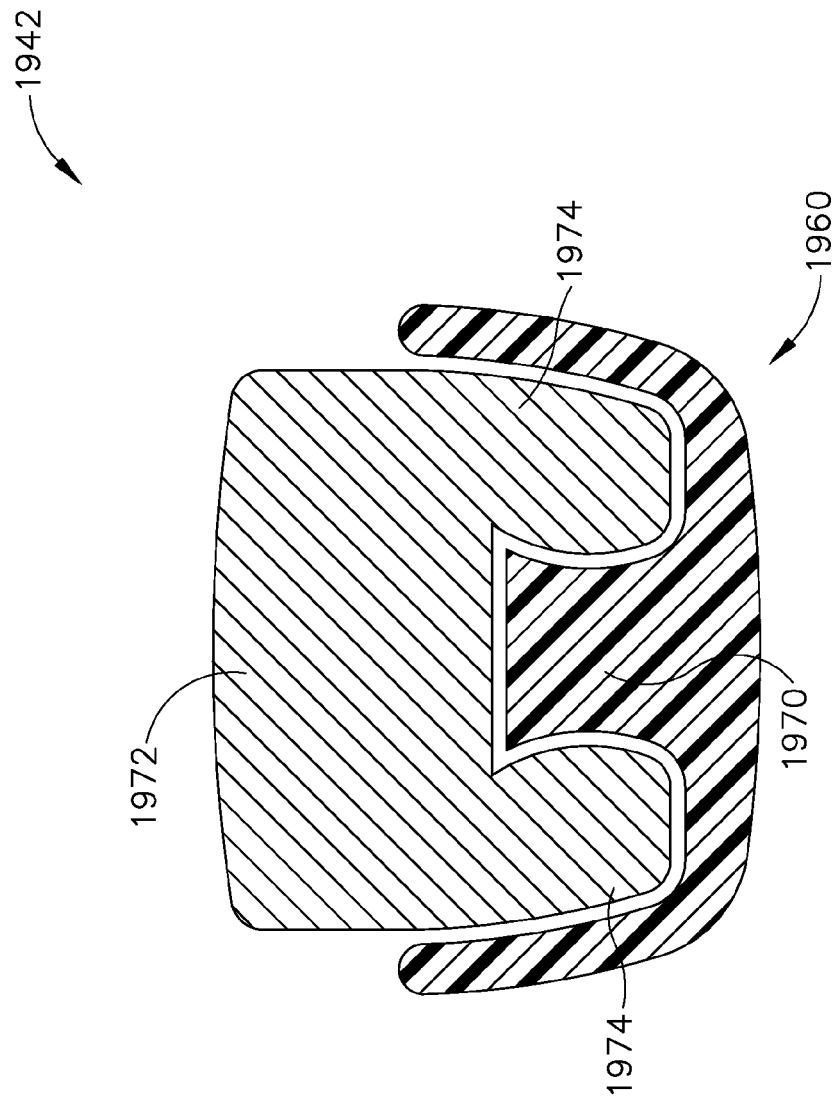
FIG. 40 depicts a cross-sectional end view of an exemplary alternative ultrasonic blade having two gripping portions for receiving an overmold.

FIG. 40 shows a cross-section of another alternative ultrasonic blade (1942) that may be readily incorporated into an instrument similar to instruments (10, 100) described above. In particular, blade (1942) is substantially similar to blade (1842) described above, except blade (1942) is configured with a different cross-sectional geometry. As can be seen, blade (1942) has a generally rectangular geometry with a channel (1970) formed therein. With such a geometry, blade (1942) includes a clamping portion (1972) and two gripping portions (1974) that define channel (1972).

Channel (1970) may permit blade (1942) to support an overmold (1960). Overmold (1960) is overmolded onto blade (1942) over both gripping portions (1974) and into channel (1970). Unlike overmold (1860) described above, overmold (1960) of the present example comprises a single material such as silicone or the like. Of course, overmold (1960) may instead comprise a plurality of materials similar to overmold (1860) described above. Yet in other examples, overmold (1960) may comprise a plastic cap that may be selectively removable from blade (1942) (e.g., in a snap fit fashion).

D. Exemplary Clamp Arms with Features for Heat Dissipation

Although instruments similar to instruments (10, 100), described above, may be equipped with blade sleeves or other blade covers to prevent tissue from inadvertently coming into direct contact with a hot blade, to effectively quench a hot blade with gathered vapor or a dispensed cooling fluid, or to otherwise dissipate heat from an end effector, it may also be desirable to provide shielding or dissipation of heat from a clamp arm. The examples described below include various features for the dissipation of heat from the clamp arm. While these features may be described within the context of an instrument similar to instrument (10) or instrument (100), it should be understood that the various features described below may be readily incorporated into any instrument described herein as will be apparent to those of ordinary skill in the art in view of the teachings herein.

Figure 41:
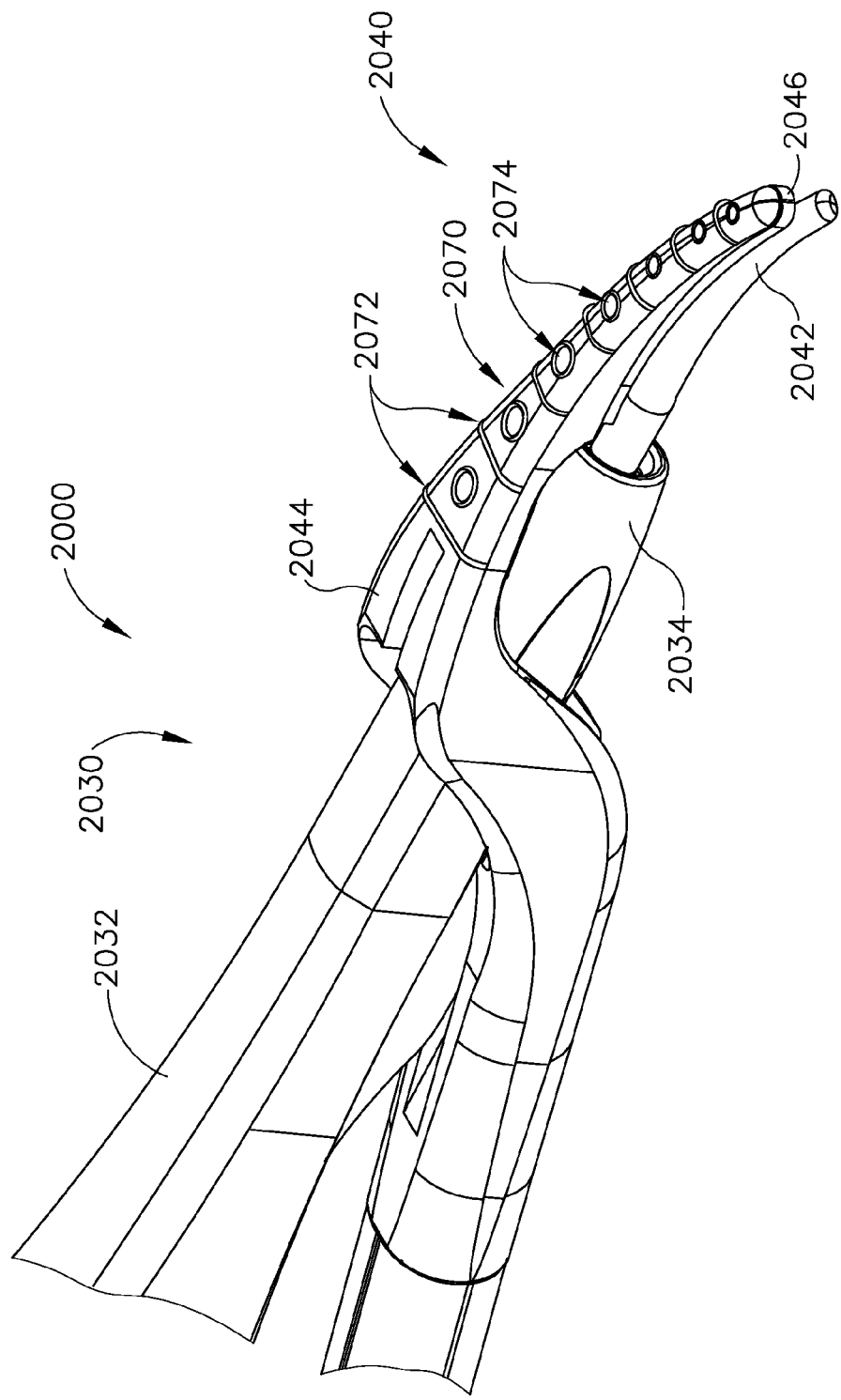
FIG. 41 depicts a detailed perspective view of an end effector of another exemplary alternative instrument having a clamp arm equipped with a heat dissipation feature.

FIG. 41 shows an exemplary alternative instrument (2000), which includes a clamp arm (2044) having a heat dissipation feature (2070). Instrument (2000) is substantially similar to instrument (100) described above except as otherwise noted below. In particular, instrument (2000) comprises a shaft assembly (2030) and an end effector (2040). Shaft assembly (2030) comprises an outer sheath (2032) and a cap (2034) attached to outer sheath (2032). Sleeve (2060) extends distally from cap (2034). End effector (2040) comprises an ultrasonic blade (2042) and a clamp arm (2044), which is pivotable relative to blade (2042) to clamp tissue between a clamp pad (2046) of clamp arm (2044) and blade (2042).

The portion of clamp arm (2044) opposite clamp pad (2046) includes a heat dissipation feature (2070). Heat dissipation feature (2070) of this example comprises a plurality of overmolded laterally extending recesses (2072) alternating with a plurality of circular protrusions (2074). Each recess (2072) gets progressively smaller from one recess (2072) to the next from the proximal end of clamp arm (2044) to the distal end of clamp arm (2044). However, recesses (2072) maintain a generally similar shape from one recess (2072) to the next. Similarly, each protrusion (2074) gets progressively smaller from one protrusion (2074) to the next from the proximal end of clamp arm (2044) to the distal end of clamp arm (2044), though protrusions (2074) maintain a generally similar shape from one protrusion (2074) to the next.

Heat dissipation feature (2070) is overmolded directly onto the surface of clamp arm (2044) and may be comprised of a material such as silicone, plastic, or the like. The shape of each protrusion (2074) is configured to provide separation between tissue and clamp arm (2044) to prevent the tissue from being adversely effected by direct contact with clamp arm (2044) when clamp arm (2044) is hot. Recesses (2072) and protrusions (2074) are further configured to increase the surface area of clamp arm (2044), thus providing greater heat dissipation. Although recesses (2072) and protrusions (2074) are shown as having certain respective shapes in this example, it should be understood that recesses (2072) and protrusions (2074) may have any other suitable shapes. Moreover, although recesses (2072) and protrusions (2074) are shown as being arranged in an alternating fashion, in other examples recesses (2072) and protrusions (2074) may be grouped together in different alternating patterns. Of course, recesses (2072) and protrusions (2074) may have any other suitable configurations as will be apparent to those of ordinary skill in the art in view of the teachings herein.

Figure 42:
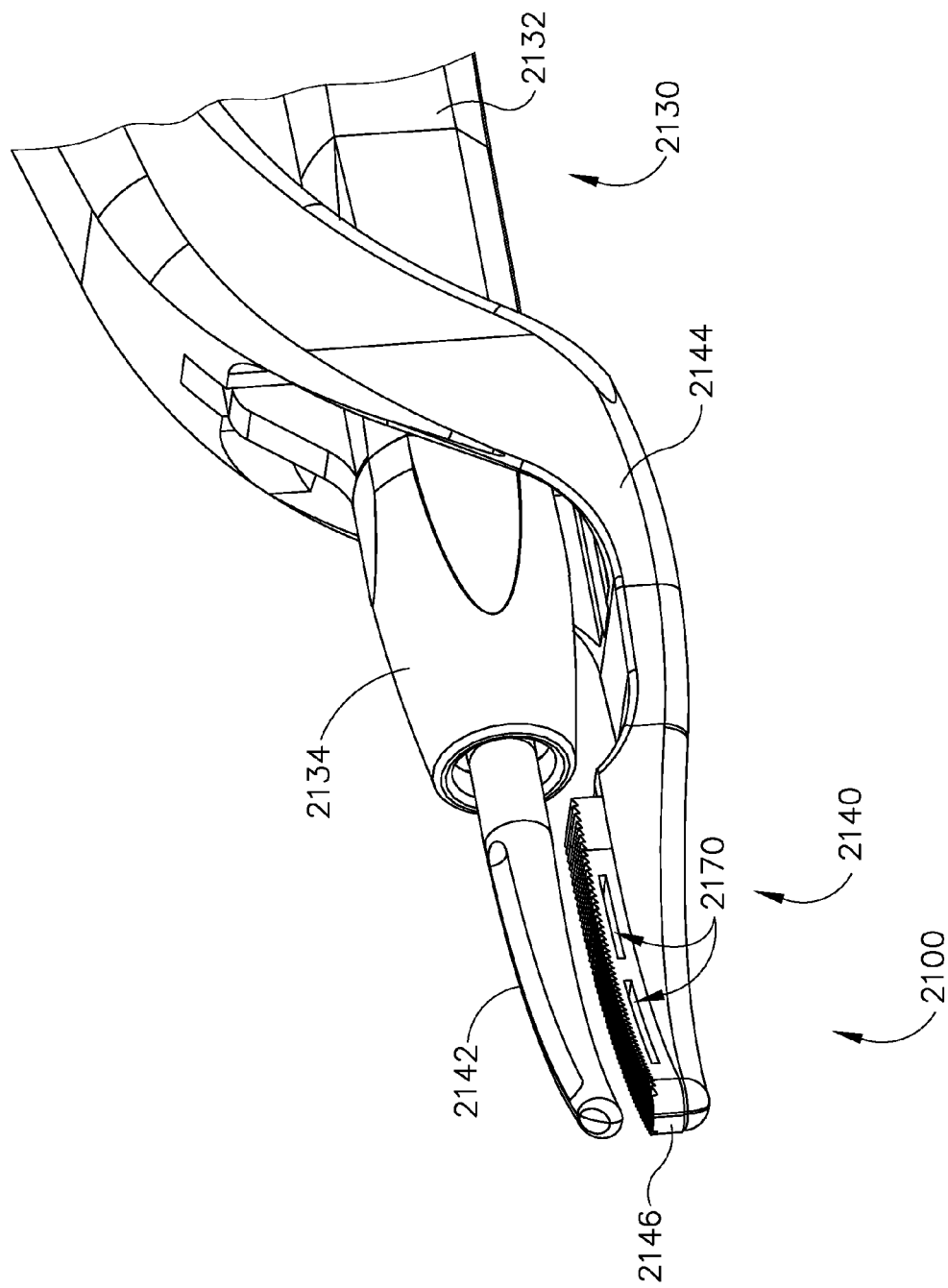
FIG. 42 depicts a perspective view of an end effector of another exemplary alternative instrument having a clamp pad equipped with a plurality of heat dissipation slots.

FIG. 42 shows another alternative instrument (2100), which includes a clamp pad (2146) having a plurality of heat dissipation slots (2170). Instrument (2100) is substantially similar to instrument (100) described above except as otherwise noted below. In particular, instrument (2100) comprises a shaft assembly (2130) and an end effector (2140). Shaft assembly (2130) comprises an outer sheath (2132) and a cap (2134) attached to outer sheath (2132). Sleeve (2160) extends distally from cap (2134). End effector (2140) comprises an ultrasonic blade (2142) and a clamp arm (2144), which is pivotable relative to blade (2142) to clamp tissue between clamp pad (2146) of clamp arm (2144) and blade (2142).

As noted above, clamp pad (2146) includes a plurality of heat dissipation slots (2170). In the present example, slots (2170) have rectangular shapes and extend transversely through clamp pad (2146) from one lateral side of clamp pad (2146) to the other lateral side of clamp pad (2146). It should be understood that while slots (2170) are shown as being rectangular in shape, they may be any other suitable shape and/or size. Clamp pad (2146) of the present example is shown as including two slots (2170), though it should be understood that clamp pad (2146) may instead include a single slot (2170) or more than two slots (2170). In the present example, slots (2170) are configured to dissipate heat by increasing the amount of surface area of clamp pad (2146). Accordingly, excess heat communicated to clamp pad (2146) from blade (2142) may be more readily dissipated via slots (2170). While slots (2170) are formed in clamp pad (2146) in this example, it should be understood that slots (2170) may be formed in clamp arm (2144) in addition to or in lieu of being formed in clamp pad (2146). Similarly, clamp arm (2144) and clamp pad (2146) may have differently configured heat dissipation slots.

Figure 43:
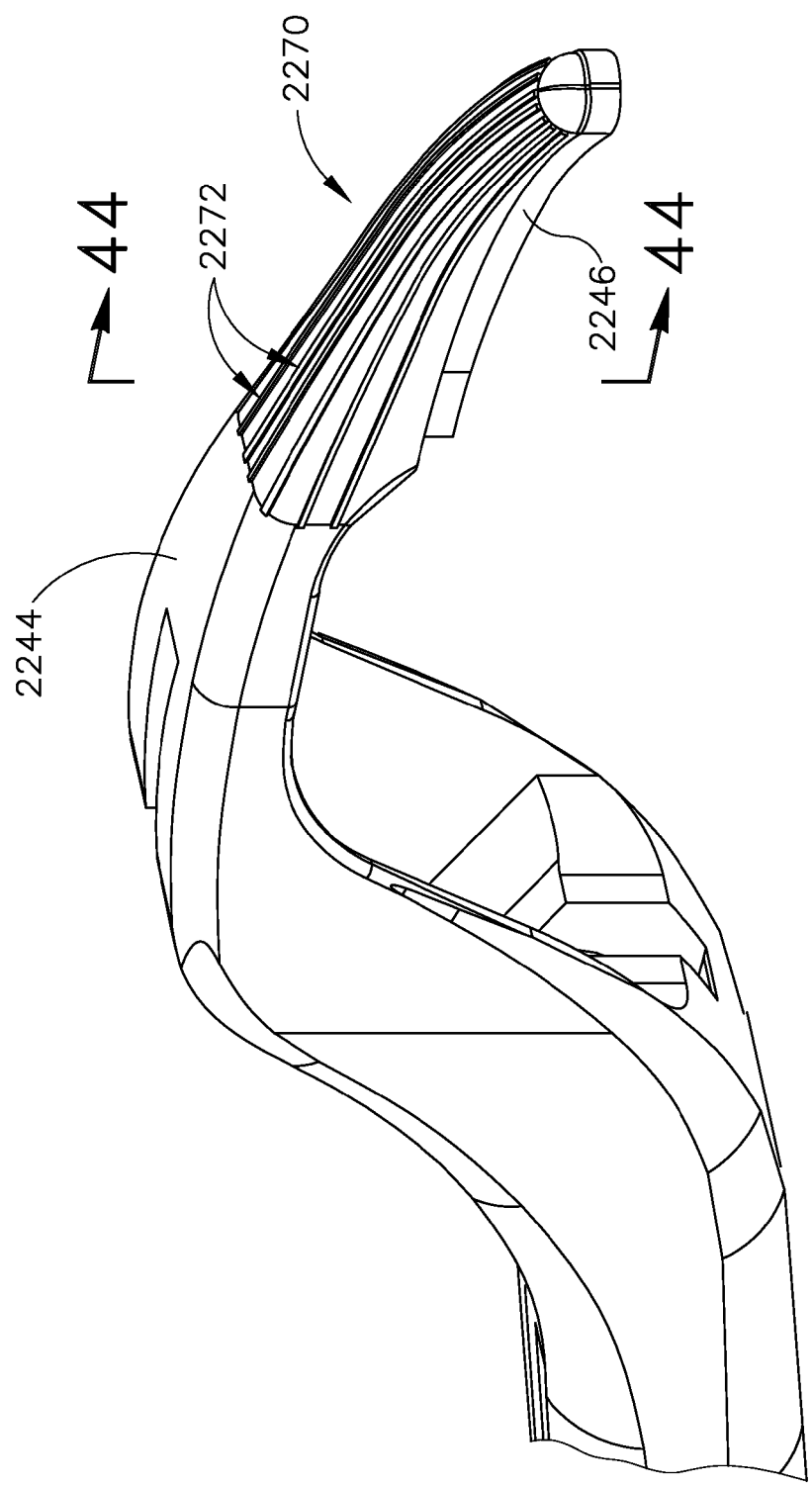
FIG. 43 depicts a detailed perspective view of an exemplary alternative clamp arm having a sheath equipped with a plurality of longitudinally extending heat dissipation features.
Figure 44:
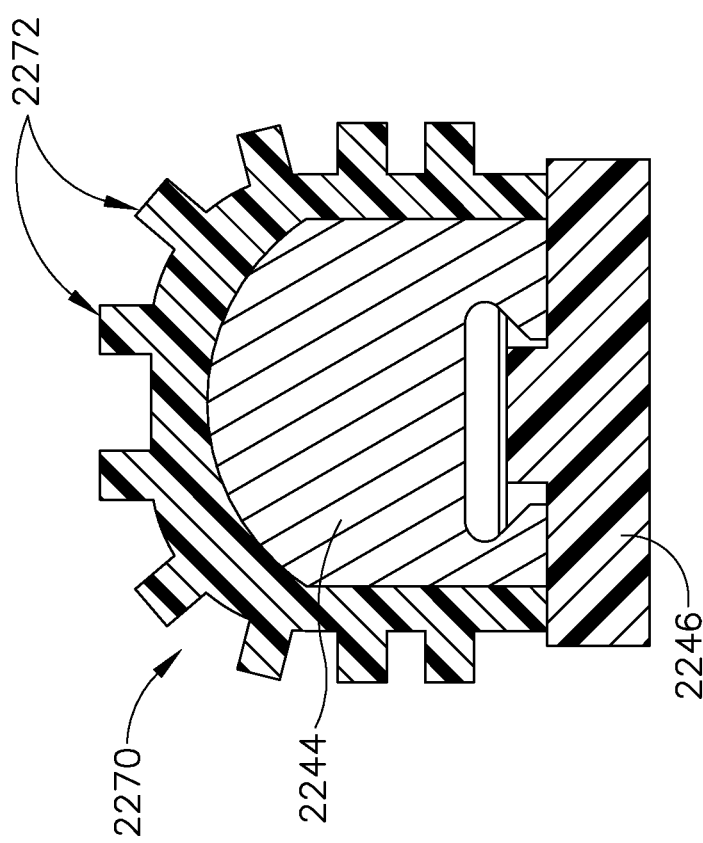
FIG. 44 depicts a cross-sectional end view of the clamp arm of FIG. 43, with the cross-section taken along line 44-44 of FIG. 43.

FIGS. 43 and 44 show an exemplary alternative clamp arm (2244) with a sheath (2270) having a plurality of longitudinally extending heat dissipation features (2272). Clamp arm (2244) is substantially the same as clamp arm (144) described above, except as otherwise noted herein. Additionally, clamp arm (2244) may be incorporated into an instrument that may be substantially the same as instrument (100) described above. Clamp arm (2244) comprises a clamp pad (2246) and sheath (2270) that is positioned adjacent to clamp pad (2246). In the present example, heat dissipation features (2272) extend distally for a length approximately equivalent to the length of clamp pad (2246). As heat dissipation features (2272) extend distally along the length of clamp arm (2244), the cross-sectional size of heat dissipation features (2272) shrinks, such that heat dissipation features (2272) are tapered along their length. Moreover, heat dissipation features (2272) converge toward each other at the distal end of clamp arm (2244). It should be understood that this shrinkage and convergence is a function of the shape of clamp arm (2244). In other words, clamp arm (2244) tapers as it extends distally such that heat dissipation features (2272) may shrink and converge to complement the taper of clamp arm (2244).

As can best be seen in FIG. 44, sheath (2270) is wrapped around the exterior of clamp arm (2244). In other examples, sheath (2270) may be overmolded to the exterior of clamp arm (2244). Regardless, sheath (2270) may be comprised of any suitable material such as silicone, polytetrafluoroethylene, or the like. Heat dissipation features (2272) are generally shaped as protrusions with square cross-sectional profiles, protruding outwardly from clamp arm (2244). Although the present example is shown as having ten heat dissipation features (2272), it should be understood that sheath (2270) may instead include any other suitable number of heat dissipation features (2272). The square profile shape of heat dissipation features (2272) increase the surface area of sheath (2270) to increase heat dissipation from clamp arm (2244). Additionally, the square profile shape provides a small standoff area to create separation between tissue and clamp arm (2244). Of course, heat dissipation features (2272) may comprise any other suitable cross-sectional profile shape.

Figure 45:
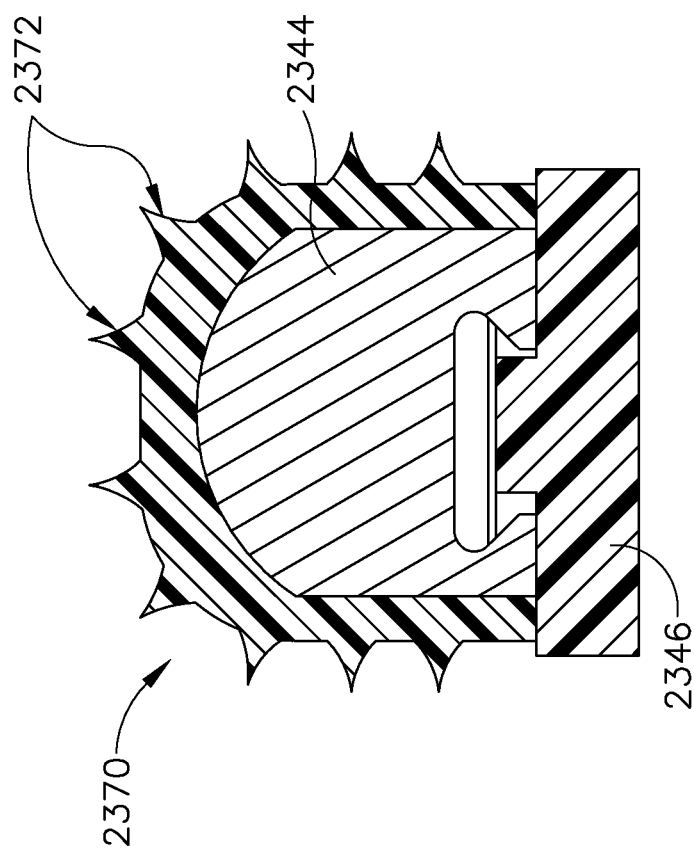
FIG. 45 depicts a cross-sectional end view of an exemplary alternative clamp arm having a sheath equipped with a plurality of longitudinally extending heat dissipation features.

FIG. 45 shows another exemplary clamp arm (2344), which is substantially the same as clamp arm (2244) described above. For instance, clamp arm (2344) comprises a sheath (2370) positioned adjacent to a clamp pad (2346). Further, sheath (2370) includes a plurality of heat dissipation features (2372). However, unlike heat dissipation features (2272) described above, heat dissipation features (2372) of the present example have a generally triangular cross-sectional profile. It should be understood that the triangular cross-sectional profile shape of heat dissipation features (2372) and the square cross-sectional profile shape of heat dissipation features (2272) are merely exemplary and in other examples heat dissipation features (2272, 2372) may comprise any other suitable cross-sectional profile shape as will be apparent to those of ordinary skill in the art in view of the teachings herein.

III. Exemplary Instruments with Tissue Locating Features

As described above, instruments (10, 100) are configured to clamp tissue between blade (42, 142) and clamp pad (46, 146) and further to cut through and seal tissue. Where tissue such as a blood vessel is disposed between the proximal and distal ends of clamp pad (46, 146), the tissue may be fully compressed against blade (42, 142) and may thus be fully cut and severed. This may sometimes be referred to as a "full bite." In some instances, tissue may extend proximally or distally past clamp pad (46, 146). In such instances, tissue that is not in contact with clamp pad (46, 146) might not be cut or sealed due to lack of compressive force between clamp pad (46, 146) and blade (42, 142). This may be desirable such as, for instance, when tissue extends distally of clamp pad (46, 146) to take a "partial bite." In other instances, such as when tissue extends proximally of clamp pad (46, 146), it may be undesirable to partially cut and/or seal such tissue because such an action may lead to an incomplete seal or cut. Thus, it may be desirable to incorporate features into instruments (10, 100) to ensure that tissue is aligned as intended between clamp pad (46, 146) and blade (42, 142). In particular, it may be desirable to ensure that tissue is not positioned proximal to clamp pad (46, 146). It should be understood that while the examples below are described within the context of instrument (10) or instrument (100), such examples may be readily applied to either instrument (10, 100) as will be understood by those of ordinary skill in the art in view of the teachings herein.

A. Exemplary Instrument with Tissue Locating Band

Figure 46:
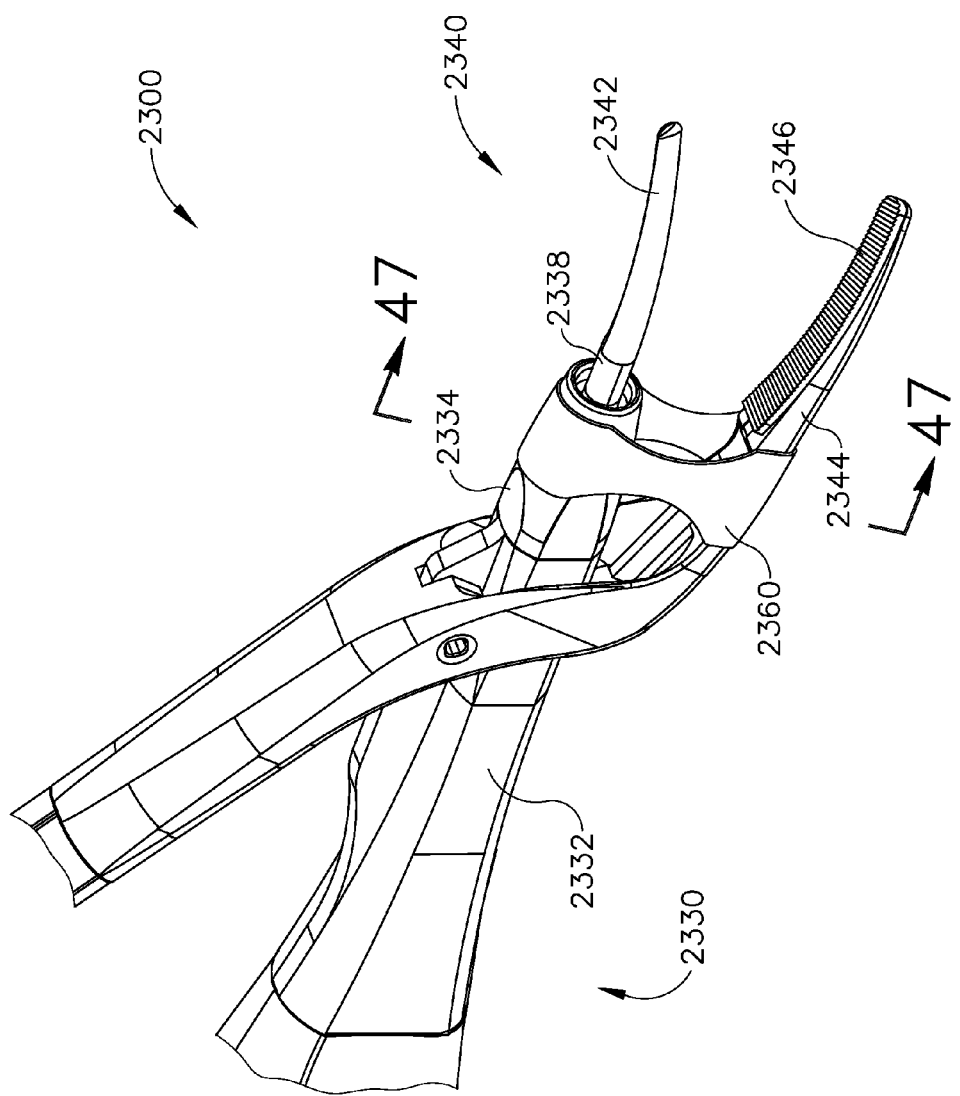
FIG. 46 depicts a detailed perspective view of an end effector of another exemplary alternative instrument having a tissue locating strap.
Figures 47A, 47B:
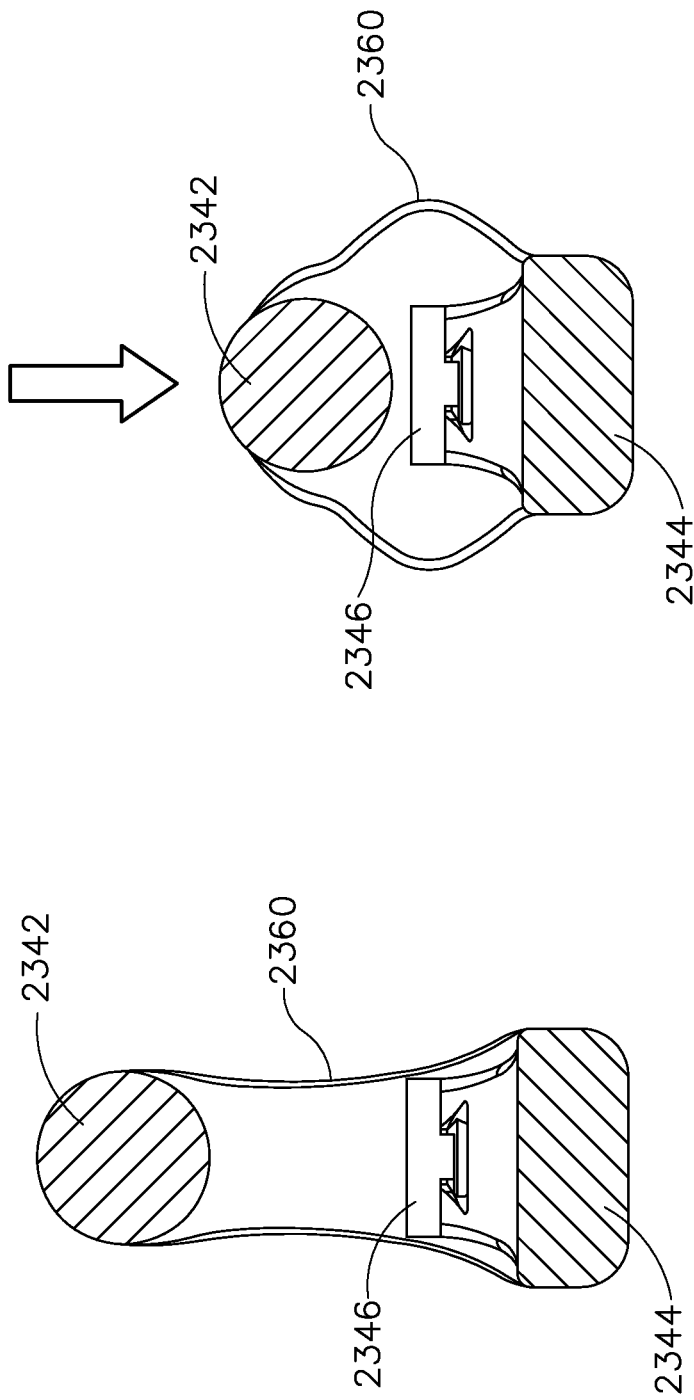
FIG. 47A depicts a cross-sectional end view of the end effector of FIG. 46 with the end effector in an open position, the cross-section taken along line 47-47 of FIG. 46.
FIG. 47B depicts a cross-sectional end view of the end effector of FIG. 46 with the end effector in a closed position, the cross-section taken along line 47-47 of FIG. 46.

FIGS. 46-47B show an exemplary alternative instrument (2300) that is equipped with a tissue locating band (2360). Instrument (2300) is substantially the same as instrument (100) described above, except as otherwise noted herein. In particular, instrument (2300) comprises a shaft assembly (2330) and an end effector (2340). Shaft assembly (2330) comprises an outer sheath (2332) and a cap (2334) attached to outer sheath (2332). Sleeve (2360) extends distally from cap (2334). End effector (2340) comprises an ultrasonic blade (2342) and a clamp arm (2344), which is pivotable relative to blade (2342) to clamp tissue between clamp pad (2346) of clamp arm (2344) and blade (2342).

End effector (2340) further comprises tissue locating band (2360) oriented proximally of clamp pad (2346) and blade (2342). As can be seen, band (2360) wraps around cap (2334) and clamp arm (2344) and may be fixedly secured to at least a portion to cap (2334) and/or clamp arm (2344). In the present example, band (2360) comprises an extensible material, such that band (2360) is operable to stretch as end effector (2340) transitions from a closed configuration (FIG. 47B) to an open configuration (FIG. 47A). Because band (2360) is configured to stretch, it should be understood that band (2360) may neck while stretched such that at least a portion of band (2360) narrows as band (2360) is expanded. To account for such necking, in other examples band (2360) may be positioned slightly distally of the proximal end of clamp pad (2346). In some versions, band (2360) is extensible and is resiliently biased to assume a configuration whereby band (2360) fits snugly about end effector (2340) when end effector (2340) is in a closed configuration. In such versions, band (2360) may be stretched to allow end effector (2340) to achieve an open configuration. In some other versions, band (2360) is flexible yet not extensible. In some such versions, band (2360) is not stretched when end effector (2340) is in the open configuration. Other suitable properties that band (2360) may have will be apparent to those of ordinary skill in the art in view of the teachings herein. It should also be understood that band (2360) may be an integral feature of a sleeve that encompasses a portion of blade (2342) like the various sleeves described above.

In an exemplary mode of operation, tissue may be inserted into end effector (2340) while end effector (2340) is in the open position. Band (2360) may prevent tissue from being over inserted into end effector (2340), thus ensuring that tissue does not extend proximally of clamp pad (2346). Band (2360) may further provide the operator with tactile feedback, such that the operator may feel tissue engaging band (2360) and thereby know that tissue is fully disposed in end effector (2340). Once tissue is properly positioned in end effector (2340), end effector (2340) may be transitioned to the closed position and blade (2342) may be activated to cut and/or seal tissue as clamp pad (2346) compresses the tissue against blade (2342).

B. Exemplary Instrument with Tissue Locating Pad

Figure 48A:
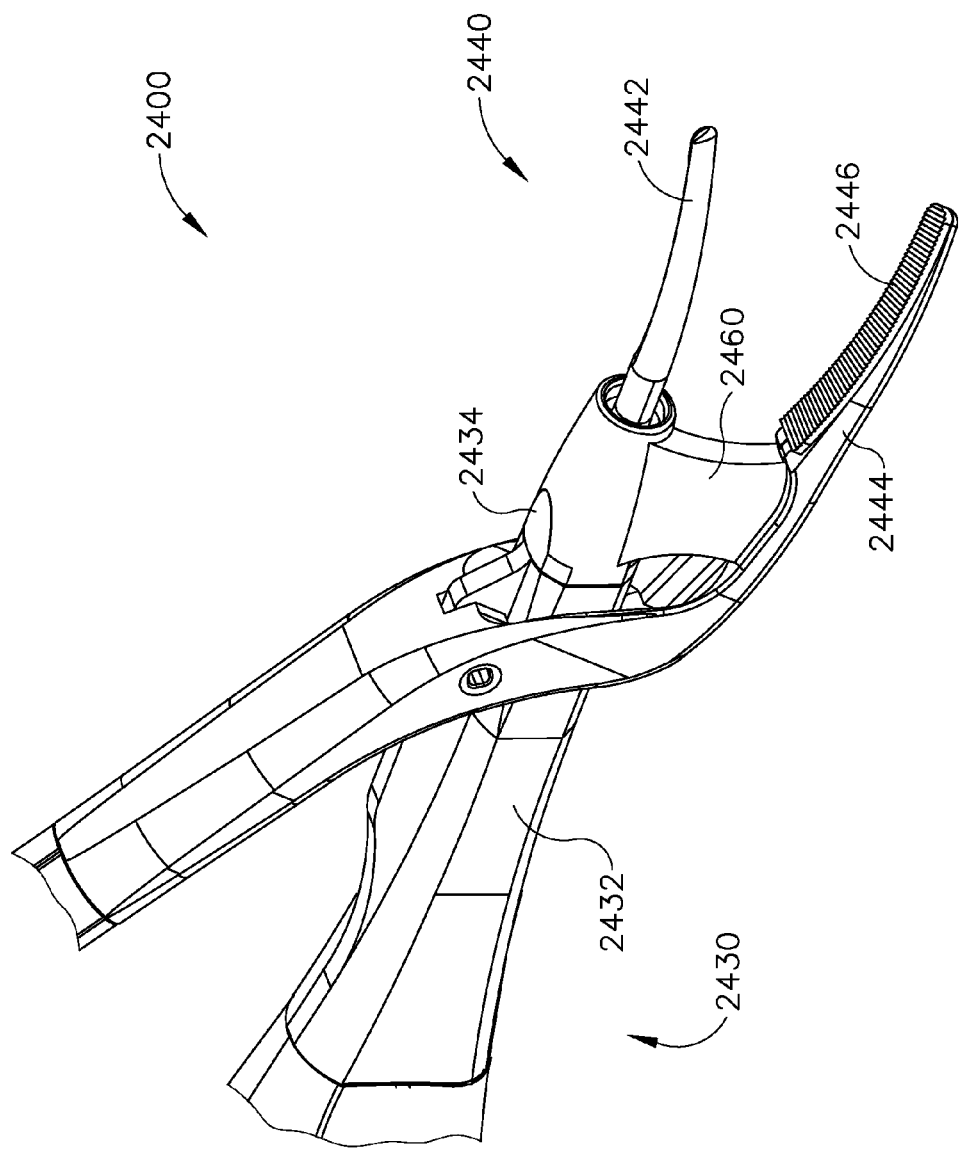
FIG. 48A depicts a detailed perspective view of an end effector of another exemplary alternative instrument having an end effector equipped with a tissue locating pad, the end effector in an open position.
Figure 48B:
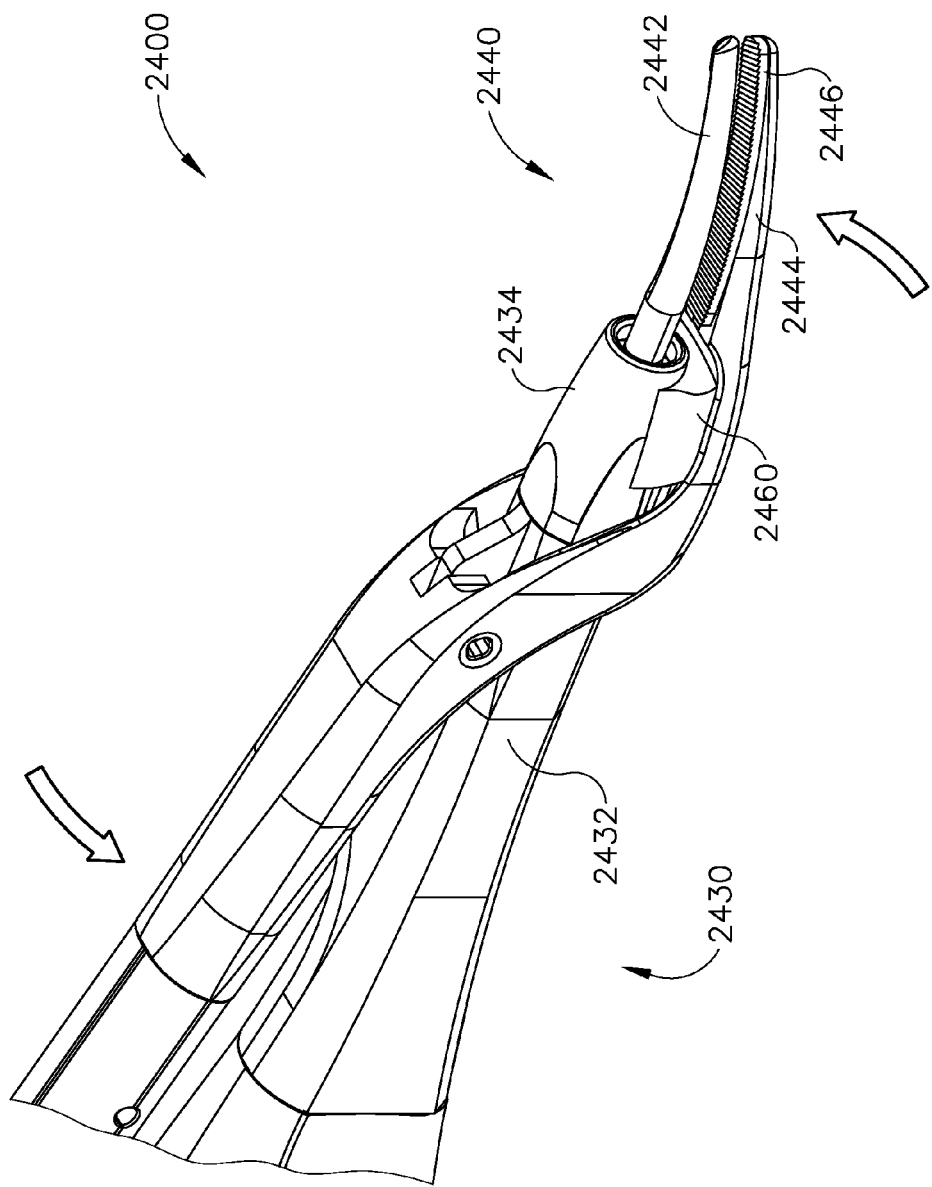
FIG. 48B depicts another detailed perspective view of the end effector of FIG. 48A, the end effector in a closed position.

FIGS. 48A and 48B show another alternative instrument (2400) that is equipped with a tissue locating pad (2460). Instrument (2400) is substantially the same as instrument (2300) described above, except tissue locating band (2360) is replaced with tissue locating pad (2460), as will be described in greater detail below. Instrument (2400) comprises a shaft assembly (2430) and an end effector (2440). Shaft assembly (2430) comprises an outer sheath (2432) and a cap (2434) attached to outer sheath (2432). Sleeve (2460) extends distally from cap (2434). End effector (2440) comprises an ultrasonic blade (2442) and a clamp arm (2444), which is pivotable relative to blade (2442) to clamp tissue between clamp pad (2446) of clamp arm (2444) and blade (2442).

End effector (2440) further comprises tissue locating pad (2460) positioned proximally of clamp pad (2446) and blade (2442). As can be seen, locating pad (2460) is fixedly secured to cap (2434) and clamp arm (2444) through adhesive bonding, welding, or the like. In the present example, locating pad (2460) comprises an elastomeric foam material, such that locating pad (2460) is operable to compress and stretch as end effector (2440) transitions between an open position (FIG. 48A) and a closed position (FIG. 48B). Because locating pad (2460) is configured to compress and stretch, it should be understood that the cross-section of locating pad (2460) may expand or contract as locating pad (2460) compressed and/or stretched. To account for this phenomenon, in other examples locating pad (2460) may be positioned slightly distally or slightly proximally of the proximal end of clamp pad (2446).

In an exemplary mode of operation, tissue may be inserted into end effector (2440) while end effector (2440) is in the open position. Locating pad (2460) may prevent tissue from being over inserted into end effector (2440), thus ensuring that tissue does not extend proximally of clamp pad (2446). Locating pad (2460) may further provide the operator with tactile feedback, such that the operator may feel tissue engaging band (2360) and thereby know that tissue is fully disposed in end effector (2440). Once tissue is properly positioned, end effector (2440) may be transitioned to the closed position and blade (2442) may be activated to cut and/or seal tissue as clamp pad (2446) compresses the tissue against blade (2442).

C. Exemplary Instrument with Visual Tissue Locating Features

Figure 49:
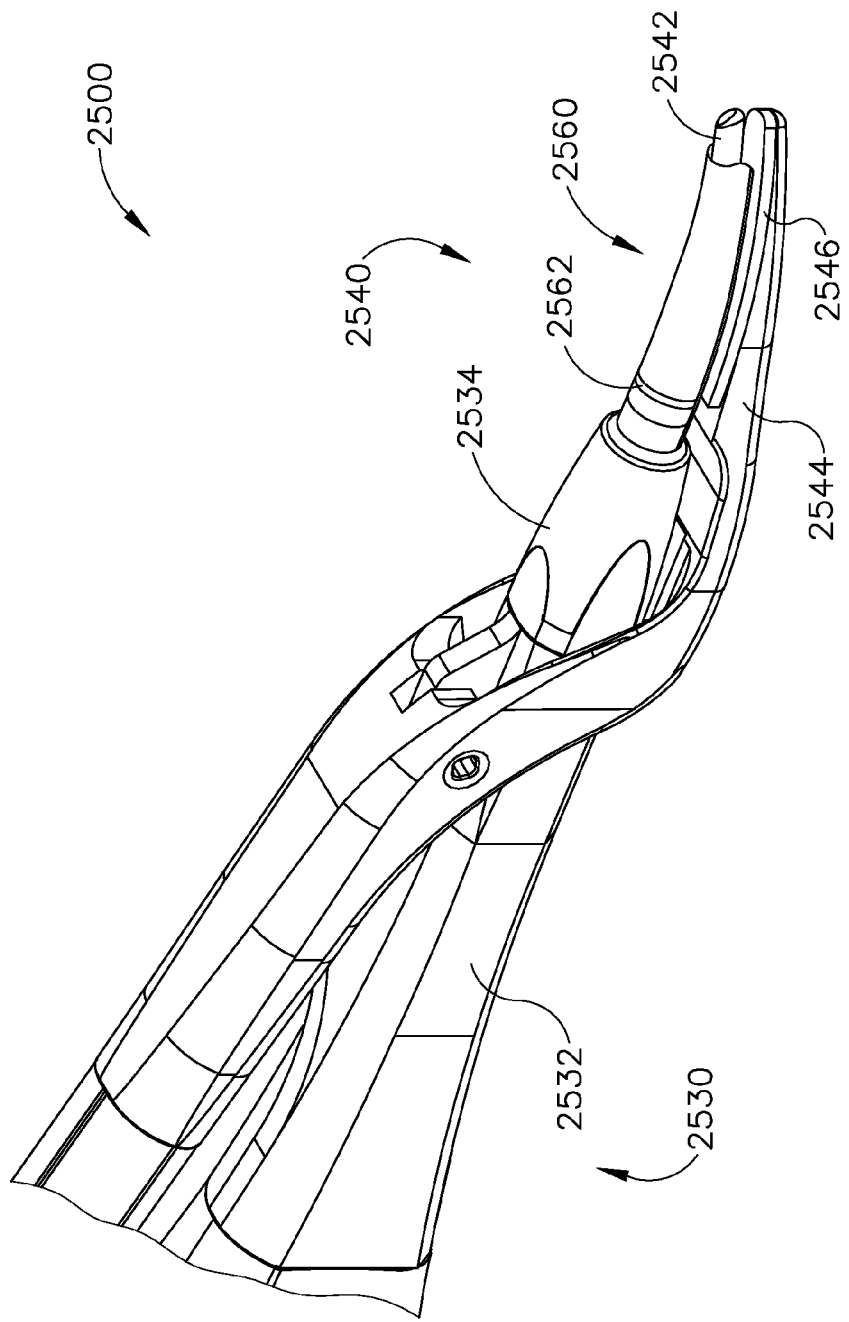
FIG. 49 depicts a detailed perspective view of an end effector of another exemplary alternative instrument having a blade sleeve equipped with a visual tissue locating feature.

FIG. 49 shows an exemplary alternative instrument (2500) that is equipped with a blade sleeve (2560) having a visual tissue locating feature (2562). Instrument (2500) is substantially the same as instrument (100) described above, except as otherwise noted herein. In particular, instrument (2500) comprises a shaft assembly (2530) and an end effector (2540). Shaft assembly (2530) comprises an outer sheath (2532) and a cap (2534) attached to outer sheath (2532). Sleeve (2560) extends distally from cap (2534). End effector (2540) comprises an ultrasonic blade (2542) and a clamp arm (2544), which is pivotable relative to blade (2542) to clamp tissue between clamp pad (2546) of clamp arm (2544) and blade (2542).

Instrument further comprises blade sleeve (2560) extending distally from cap (2534). Blade sleeve (2560) is substantially the same as blade sleeve (760) described above, except blade sleeve (2560) includes visual tissue locating feature (2562). Tissue locating feature (2562) comprises a visible line extending laterally across sleeve (2560), which is aligned with the proximal end of clamp pad (2546). Thus, tissue locating feature (2562) is configured to provide an operator with additional visual feedback indicating the location where clamp pad (2546) proximally terminates. It should be understood that, in other examples, sleeve (2560)

may include other tissue locating features (2562) in addition to the one shown. For instance, sleeve (2560) may include two tissue locating features (2562) with one corresponding to tissue placement for a "partial bite" and another corresponding to tissue placement for a "full bite." Additionally, where multiple tissue locating features (2562) are used, tissue locating features (2562) may be color coded to more readily identify a particular tissues locating feature (2562). In some other examples, such as where blade (2542) is coated with parylene, sleeve (2560) may be omitted entirely. In such examples, it should be understood that tissue locating feature(s) (2562) may be located directly on blade (2542).

Figure 50:
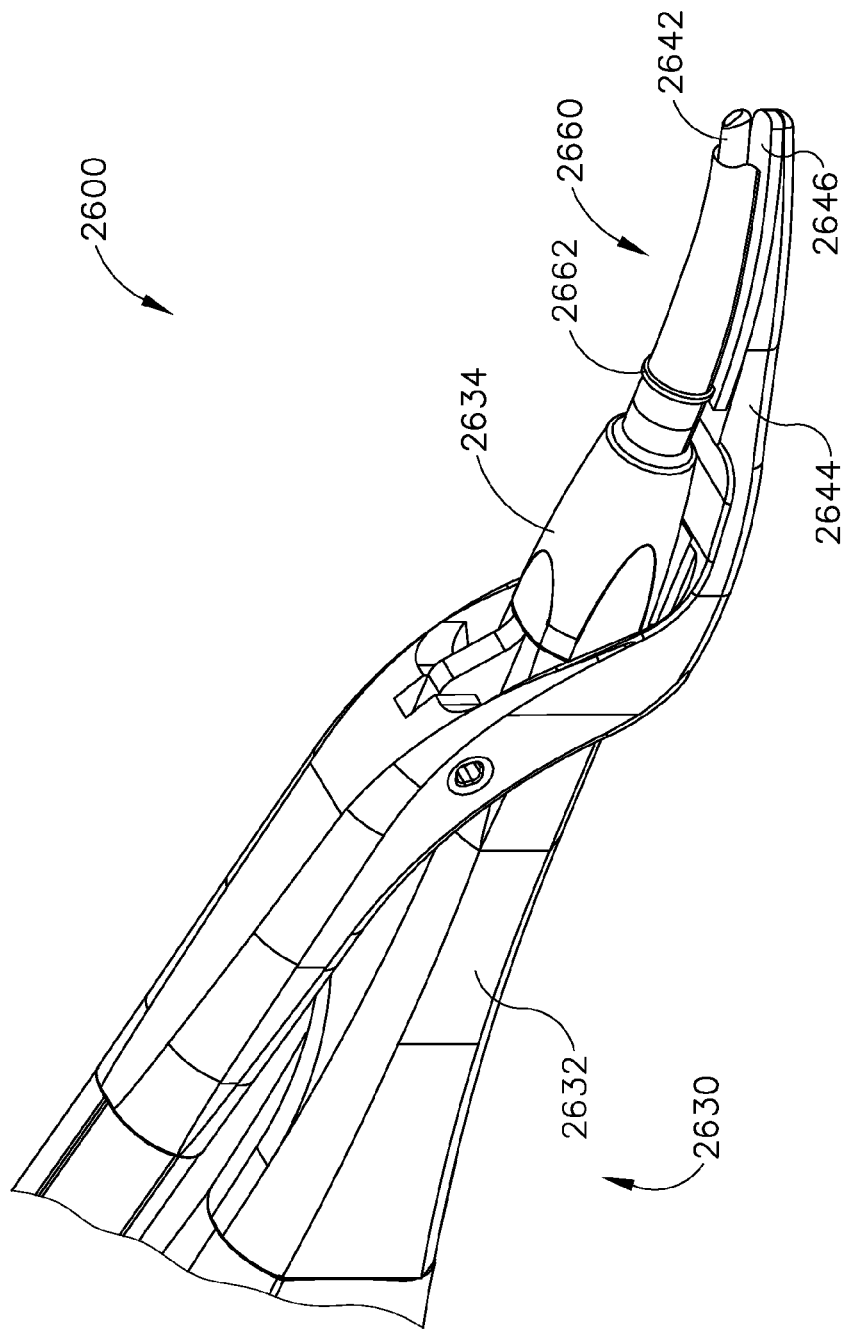
FIG. 50 depicts a detailed perspective view of an end effector of another exemplary alternative instrument having a blade sleeve equipped with a visual tissue locating feature.

FIG. 50 shows another alternative instrument (2600) that is equipped with a blade sleeve (2660) having a visual tissue locating feature (2662). Instrument (2600) is substantially the same as instrument (2500) described above, except tissue locating feature (2662) of this example comprises an outwardly extending protrusion instead of a line. Instrument (2600) comprises a shaft assembly (2630) and an end effector (2640). Shaft assembly (2630) comprises an outer sheath (2632) and a cap (2634) attached to outer sheath (2632). Sleeve (2660) extends distally from cap (2634). End effector (2640) comprises an ultrasonic blade (2642) and a clamp arm (2644), which is pivotable relative to blade (2642) to clamp tissue between clamp pad (2646) of clamp arm (2644) and blade (2642).

Instrument further comprises blade sleeve (2660) extending distally from cap (2634). Blade sleeve (2660) is substantially the same as blade sleeve (2560) described above, except blade sleeve (2660) includes visual tissue locating feature (2662) that incorporates a protrusion instead of just a line. As was noted above, tissue locating feature (2662) is a protrusion extending laterally across sleeve (2660), which is aligned with the proximal end of clamp pad (2646). Tissue locating feature (2662) may be integral to sleeve (2660) or fixedly secured to the exterior of sleeve (2660). Additionally, tissue locating feature (2662) may have any suitable cross-sectional profile such as square, triangular, rounded, or etc. Like tissue locating feature (2562), tissue locating feature (2662) is configured to provide a user with additional visual feedback indicating the location where clamp pad (2546) proximally terminates. It should be understood that in other examples, sleeve (2660) may include other tissue locating features (2662) in addition to the one shown. For instance, sleeve (2660) may include two tissue locating features (2662) with one corresponding to tissue placement for a "partial bite" and another corresponding to tissue placement for a "full bite." Additionally, where multiple tissue locating features (2662) are used, tissue locating features (2662) may be color coded or shaped differently to more readily identify a particular tissues locating feature (2662). Of course, even where a single tissue locating feature (2662) is used, that tissue locating feature (2662) may be colored to further promote visualization of tissue locating feature (2662).

As another merely illustrative variation, in versions where a blade sleeve comprises a relatively soft inner layer and a relatively rigid outer layer, the distal end of the outer layer may terminate at a longitudinal position corresponding to the proximal end of the clamp pad. The distal end of the outer layer may thus provide a visual indication of where the proximal end of the clamp pad is located. Other suitable variations will be apparent to those of ordinary skill in the art in view of the teachings herein.

Figure 51:
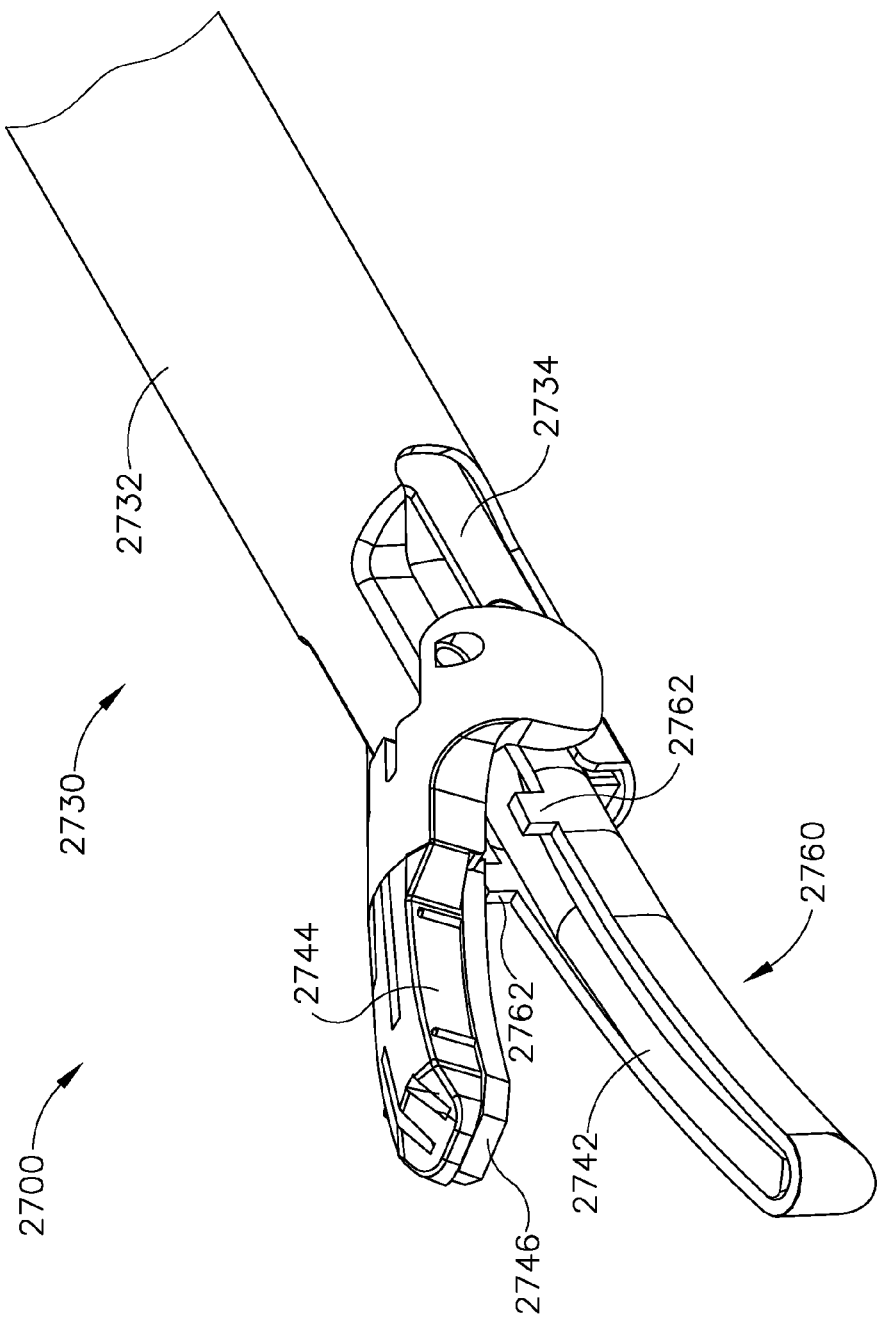
FIG. 51 depicts a detailed perspective view of an end effector of another exemplary alternative instrument having a blade sleeve equipped with two physical tissue locating features.
Figure 52:
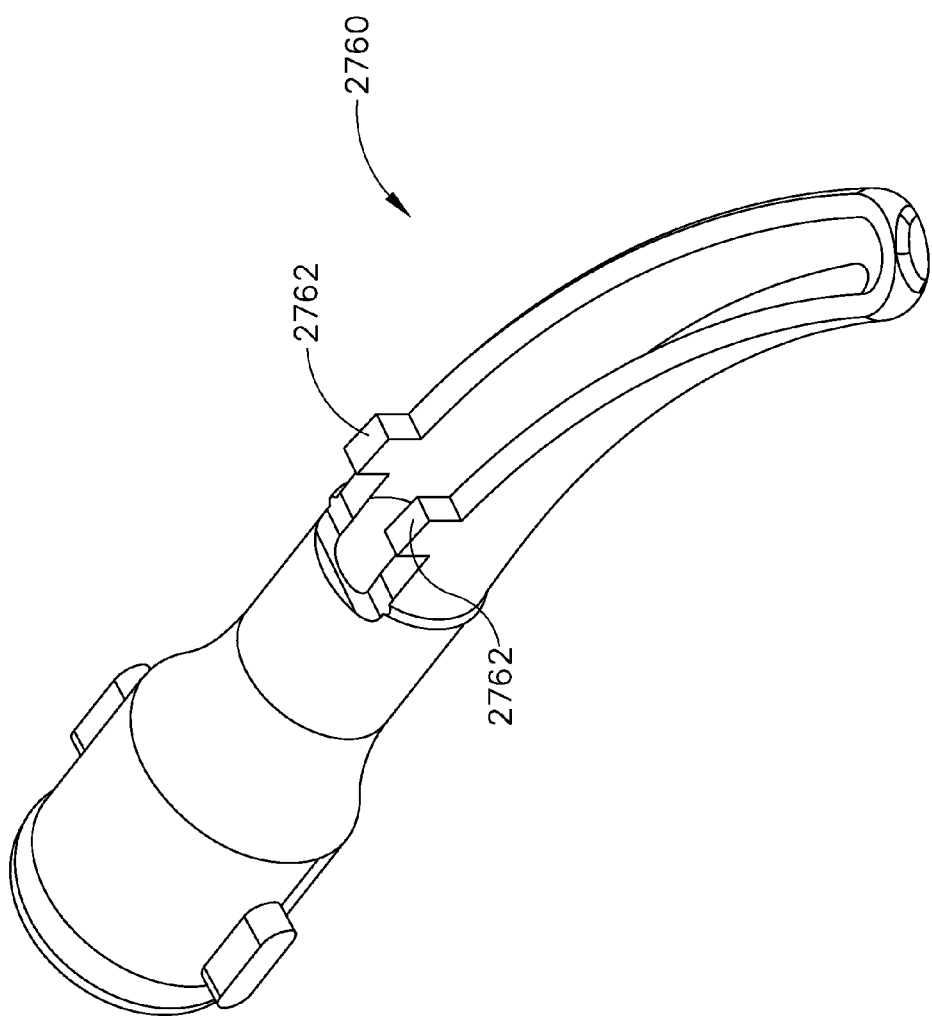
FIG. 52 depicts a perspective view of the blade sleeve of FIG. 51.

D. Exemplary Instrument with Blade Sleeve having Physical Tissue Locating Features FIGS. 51 and 52 show an exemplary alternative instrument (2700), which incorporates a blade sleeve (2760) having two tissue locating prongs (2762). Instrument (2700) is substantially similar to instrument (10) described above except as otherwise noted below. In particular, instrument (2700) comprises a shaft assembly (2730) and an end effector (2740). Shaft assembly (2730) comprises an outer sheath (2732) and an inner tube (2734) oriented coaxially within outer sheath (2732). Sleeve (2760) extends distally from inner tube (2734), as will be described in greater detail below. End effector (2740) comprises an ultrasonic blade (2742) and a clamp arm (2744), which is pivotable relative to blade (2742) to clamp tissue between a clamp pad (2746) of clamp arm (2744) and blade (2742).

As noted above, blade sleeve (2760) comprises two physical tissue locating prongs (2762). Tissue locating prongs (2762) comprise a pair of square protrusions extending upwardly from the top of sleeve (2760) in this example. However, it should be understood that tissue locating prongs (2762) may instead have any other suitable configurations. Tissue locating prongs (2762) are positioned to correspond with the proximal end of clamp pad (2746). Thus, tissue locating prongs (2762) act as a physical stop for tissue when tissue is inserted into end effector (2740), thereby preventing over insertion of tissue. Tissue locating prongs (2762) may further provide the operator with tactile feedback, such that the operator may feel tissue engaging tissue locating prongs (2762) and thereby know that tissue is fully disposed in end effector (2760). While tissue locating prongs (2762) are shown as being integral with sleeve (2760), in other examples tissue locating prongs (2762) may be separately formed and fixedly secured to sleeve (2760).

In some versions, blade sleeve (2760) is resiliently biased to closely encompass the outer region of blade (2742). In some such versions, blade sleeve (2760) may be resiliently biased to contact blade (2742). In versions where blade sleeve (2760) is resiliently biased to closely encompass (and perhaps contact) the outer region of blade (2742), clamp arm (2744) may be configured to engage tissue locating prongs (2762) and thereby drive blade sleeve (2760) away from blade (2742) when clamp arm (2744) is pivoted to the closed position. In some such versions, sleeve (2760) may generally pivot or flex away from blade (2742) when clamp arm (2744) pushes prongs (2762) as clamp arm (2744) is pivoted to the closed position. Thus, when clamp arm (2744) is in the open position, sleeve (2760) may closely encompass (and perhaps contact) the outer region of blade (2742); then deform to deflect away from blade (2742) when clamp arm (2744) is in the closed position. Alternatively, tissue locating prongs (2762) may be configured and positioned such that clamp arm (2744) does not engage prongs (2762) when clamp arm (2744) is pivoted to the closed position. It should also be understood that one or more features other than clamp arm (2744) may be configured to drive sleeve (2760) away from blade (2742) when clamp arm (2744) is pivoted to the closed position and/or at any other suitable stage of operation. Moreover, some versions of sleeve (2760) may comprise a non-resilient material. By way of example only, a leaf spring, torsion spring, or some other resilient member may provide a resilient bias to a sleeve (2760) that comprises a non-resilient material. Alternatively, sleeve (2760) may be non-biased in some versions. Other suitable variations will be apparent to those of ordinary skill in the art in view of the teachings herein.

IV. Miscellaneous

It should be understood that the teachings herein may be readily combined with the teachings of any of the references that are cited herein. It should also be understood that the teachings herein may be readily combined with the teachings of U.S. Pub. No. 2015/0148833, entitled "Shielding Features for Ultrasonic Blade of a Surgical Instrument," published May 28, 2015, the disclosure of which is incorporated by reference herein. Various suitable ways in which the teachings may be combined will be apparent to those of ordinary skill in the art.

In addition to or as an alternative to using shielding to reduce heat in a version of instrument (10, 100), a fluid may be used to cool blade (42, 142). For instance, a cooling liquid (e.g., saline, etc.) may be applied to the proximal end of blade (42, 142). The cooling fluid may then be communicated distally along the rest of the length of blade (42, 142) to thereby cool blade. The ultrasonic vibration of blade (42, 142) may provide such distal communication of the fluid. In some such versions, a particular vibrational scheme may be used to drive liquid distally along blade (42, 142). Such a particular, vibrational scheme may have no meaningful effect on tissue that is in contact with blade (42, 142) while blade is being driven in such a fashion. For instance, blade (42, 142) may be vibrated in short pulses (e.g., of approximately 10 to 20 millisecond duration) of low amplitude motion to drive the liquid distally along blade (42, 142). In some such instances, generator (16, 116) is programmed to provide such liquid driving ultrasonic activation of blade (42, 142) when the operator is not pressing any buttons (26, 126). In addition or in the alternative, generator (16, 116) may be programmed to provide liquid driving ultrasonic activation of blade (42, 142) when generator (16, 116) detects that blade (42, 142) is not contacting tissue. As yet another merely illustrative example, instrument (10, 100) may include a separate user input feature that is operable to manually trigger a liquid driving vibrational scheme. Other suitable ways in which a liquid driving vibrational scheme may be triggered will be apparent to those of ordinary skill in the art in view of the teachings herein.

In some other versions, the same vibrational movement that is used to drive blade during tissue cutting/sealing may drive liquid distally along blade (42, 142). As yet another merely illustrative example, fluid may be communicated to and/or along blade in accordance with at least some of the teachings of U.S. Pub. No. 2011/0152759, entitled "Use of Biomarkers and Therapeutic Agents with Surgical Devices," published Jun. 23, 2011, now U.S. Pat. No. 8,591,459, issued Nov. 26, 2013, the disclosure of which is incorporated by reference herein. It should be understood that the teachings in U.S. Pub. No. 2011/0152759, now U.S. Pat. No. 8,591,459, relating to dispensation of medical fluids may be readily adapted to provide communication of cooling fluid. Additional examples of ways in which fluid may be used to cool blade (42, 142) are described in U.S. Pub. No. 2015/0148832, entitled "Features to Apply Fluid to an Ultrasonic Blade of a Surgical Instrument," published May 28, 2015, the disclosure of which is incorporated by reference herein; U.S. Pub. No. 2016/0143658, entitled "Features to Drive Fluid toward an Ultrasonic Blade of a Surgical Instrument," published May 26, 2016, the disclosure of which is incorporated by reference herein; U.S. Pub. No. 2016/0143657, entitled "Features for Communication of Fluid through Shaft Assembly of Ultrasonic Surgical Instrument," published May 26, 2016, the disclosure of which is incorporated by reference herein; and U.S. Pub. No. 2016/0143659, entitled "Ultrasonic Surgical Instrument with Blade Cooling through Retraction," published May 26, 2016, the disclosure of which is incorporated by reference herein. It should be understood that the teachings herein may be readily combined with the teachings of those references and the various other references cited herein. Other examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement are described in U.S. Provisional Patent App. No. 61/908,920, the disclosure of which is incorporated by reference herein; and also in U.S. Pub. No. 2015/0148834, entitled "Ultrasonic Surgical Instrument with Staged Clamping," published May 28, 2015, the disclosure of which is incorporated by reference herein. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a shaft assembly defining a longitudinal axis; and
(b) an end effector located at a distal end of the shaft assembly, wherein the end effector comprises:
(i) an ultrasonic blade, wherein the ultrasonic blade is configured to vibrate at an ultrasonic frequency,
(ii) a clamp arm having a clamping surface, wherein the clamp arm is configured to move toward and away from a first side of the ultrasonic blade for clamping tissue against the ultrasonic blade with the clamping surface, and
(iii) a sleeve, wherein the sleeve extends longitudinally along and covers at least a portion of a second side of the ultrasonic blade, wherein the sleeve is configured to prevent tissue from contacting the portion of the second side of the ultrasonic blade covered by the sleeve,
wherein the sleeve is movably coupled to the end effector via a movable coupling having a recess, wherein the recess is configured to guide movement of the sleeve transversely relative to the longitudinal axis in directions toward and away from the ultrasonic blade and the clamping surface of the clamp arm in a plane extending perpendicularly to the clamping surface, wherein the sleeve is fixed longitudinally relative to the ultrasonic blade.

2. The apparatus of claim 1, wherein the sleeve extends distally from the distal end of the shaft assembly.

3. The apparatus of claim 1, wherein the movable coupling further includes a longitudinally fixed element, wherein the recess is configured to slidably receive the longitudinally fixed element therein to enable transverse movement of the sleeve relative to the longitudinal axis while restricting longitudinal movement of the sleeve relative to the ultrasonic blade.

4. The apparatus of claim 3, wherein the movable coupling includes an attachment feature rigidly coupled to the sleeve, wherein the recess is arranged on the attachment feature.

5. The apparatus of claim 3, wherein the clamp arm is pivotally coupled to the shaft assembly with a pivot pin, wherein the longitudinally fixed element comprises the pivot pin.

6. The apparatus of claim 1, wherein the clamp arm is configured to pivot relative to the ultrasonic blade between open and closed positions, wherein the end effector further comprises a deflection feature operatively associated with the sleeve, wherein the deflection feature is configured to urge the sleeve transversely toward the ultrasonic blade when the clamp arm is in the open position.

7. The apparatus of claim 6, wherein the deflection feature is coupled to and projects transversely from the sleeve.

8. The apparatus of claim 1, wherein the sleeve includes a tapered protrusion arranged opposite of the movable coupling, wherein the shaft assembly is operable to selectively engage the tapered protrusion to drive the sleeve transversely toward and away from the ultrasonic blade.

9. An apparatus comprising:
(a) a body;
(b) a shaft assembly extending distally from the body and defining a longitudinal axis, wherein the shaft assembly comprises a translating member, wherein the translating member is operable to translate longitudinally relative to the body between first and second positions; and
(c) an end effector located at a distal end of the shaft assembly, wherein the end effector comprises:
(i) an ultrasonic blade, wherein the ultrasonic blade is configured to vibrate at an ultrasonic frequency, (ii) a clamp arm coupled with the translating member, wherein the clamp arm is configured to move toward a first side of the ultrasonic blade in response to movement of the translating member from the first position to the second position, and (iii) a sleeve extending along at least part of the length of a second side of the ultrasonic blade, wherein the translating member is movably coupled with the clamp arm and the sleeve, wherein the translating member is configured to drive at least a portion of the sleeve transversely toward the ultrasonic blade and simultaneously drive the clamp arm away from the ultrasonic blade when the translating member moves from the second position to the first position.

10. The apparatus of claim 9, wherein at least one of the sleeve or the translating member includes a sloped surface configured to engage a portion of the other of the sleeve or the translating member to effect transverse movement of the sleeve relative to the longitudinal axis.

11. The apparatus of claim 9, wherein the sleeve is resiliently biased away from the ultrasonic blade.

12. An apparatus comprising:
(a) a shaft assembly defining a longitudinal axis; and
(b) an end effector located at a distal end of the shaft assembly, wherein the end effector comprises:
   (i) an ultrasonic blade configured to vibrate at an ultrasonic frequency,
   (ii) a clamp arm, wherein the clamp arm is movable to clamp tissue against a first side of the ultrasonic blade, and
   (iii) a sleeve confronting a second side of the ultrasonic blade, wherein the sleeve is configured to translate transversely relative to the longitudinal axis between first and second positions, wherein the ultrasonic blade is positioned within an interior of the sleeve in each of the first and second positions, wherein the sleeve is configured to extend around at least a portion of a distal-most end of the ultrasonic blade in each of the first and second positions.

13. The apparatus of claim 12, wherein the sleeve is movable between the first and second positions such that an interior surface of the sleeve moves transversely toward and away from the second side of the ultrasonic blade.

* * * * *